US012799484B2

(12) United States Patent
Rigo

(10) Patent No.: US 12,799,484 B2
(45) Date of Patent: Nov. 17, 2026

(54) COMPOSITIONS FOR MODULATING C9ORF72 EXPRESSION

(71) Applicant: Ionis Pharmaceuticals, Inc., Carlsbad, CA (US)

(72) Inventor: Frank Rigo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 1104 days.

(21) Appl. No.: 16/948,435

(22) Filed: Sep. 18, 2020

(65) Prior Publication Data

US 2021/0230589 A1 Jul. 29, 2021

Related U.S. Application Data

(63) Continuation of application No. 16/163,402, filed on Oct. 17, 2018, now Pat. No. 10,815,483, which is a continuation of application No. 15/404,979, filed on Jan. 12, 2017, now Pat. No. 10,138,482, which is a continuation of application No. 15/130,818, filed on Apr. 15, 2016, now Pat. No. 9,605,263.

(60) Provisional application No. 62/239,400, filed on Oct. 9, 2015, provisional application No. 62/232,941, filed on Sep. 25, 2015, provisional application No. 62/148,691, filed on Apr. 16, 2015.

(51) Int. Cl.

*C12N 15/113* (2010.01)
*C07H 21/04* (2006.01)

(52) U.S. Cl.

CPC ........... *C12N 15/113* (2013.01); *C07H 21/04* (2013.01); *C12N 2310/11* (2013.01); *C12N 2310/315* (2013.01); *C12N 2310/322* (2013.01); *C12N 2310/3231* (2013.01); *C12N 2310/3341* (2013.01); *C12N 2310/341* (2013.01); *C12N 2310/346* (2013.01); *C12N 2320/30* (2013.01)

(58) Field of Classification Search

CPC ............. C12N 15/113; C12N 2310/11; C12N 2310/315; C12N 2310/322; C12N 2310/3231; C12N 2310/3341; C12N 2310/341; C12N 2310/346; C12N 2320/30; C07H 21/04

See application file for complete search history.

(56) References Cited

U.S. PATENT DOCUMENTS

| | | | |
|---|---|---|---|
| 5,801,154 | A | 9/1998 | Baracchini et al. |
| 5,998,148 | A | 12/1999 | Bennett et al. |
| 6,268,490 | B1 | 7/2001 | Imanishi et al. |
| 6,525,191 | B1 | 2/2003 | Ramasamy |
| 6,582,908 | B2 | 6/2003 | Fodor et al. |
| 6,670,461 | B1 | 12/2003 | Wengel et al. |
| 6,770,748 | B2 | 8/2004 | Imanishi et al. |
| 6,794,499 | B2 | 9/2004 | Wengel et al. |
| 7,034,133 | B2 | 4/2006 | Wengel et al. |
| 7,053,207 | B2 | 5/2006 | Wengel et al. |
| 7,399,845 | B2 | 7/2008 | Seth et al. |
| 7,427,672 | B2 | 9/2008 | Imanishi et al. |
| 7,547,684 | B2 | 6/2009 | Seth et al. |
| 7,696,345 | B2 | 4/2010 | Allerson et al. |
| 7,759,478 | B1 | 7/2010 | Bentwich et al. |
| 8,501,805 | B2 | 8/2013 | Seth et al. |
| 8,530,640 | B2 | 9/2013 | Seth et al. |
| 8,546,556 | B2 | 10/2013 | Seth et al. |
| 8,927,513 | B2 | 1/2015 | Manoharan et al. |
| 9,012,421 | B2 | 4/2015 | Migawa et al. |
| 9,605,263 | B2 | 3/2017 | Rigo |
| 9,963,699 | B2 | 5/2018 | Bennett et al. |
| 10,066,288 | B2 | 9/2018 | Hsiao |
| 10,138,482 | B2 | 11/2018 | Rigo |
| 10,221,414 | B2 | 3/2019 | Freier et al. |
| 10,443,052 | B2 | 10/2019 | Freier |
| 10,577,604 | B2 | 3/2020 | Bennett et al. |
| 10,815,483 | B2 | 10/2020 | Rigo |
| 11,339,393 | B2 | 5/2022 | Freier et al. |
| 2001/0053519 | A1 | 12/2001 | Fodor et al. |
| 2003/0228597 | A1 | 12/2003 | Cowsert et al. |
| 2004/0038274 | A1 | 2/2004 | Cook et al. |
| 2004/0171570 | A1 | 9/2004 | Allerson et al. |
| 2004/0181048 | A1 | 9/2004 | Wang |
| 2005/0130923 | A1 | 6/2005 | Bhat et al. |
| 2005/0255487 | A1 | 11/2005 | Khvorova et al. |
| 2006/0003322 | A1 | 1/2006 | Bentwich et al. |
| 2006/0270623 | A1 | 11/2006 | McSwiggen |
| 2007/0031844 | A1 | 2/2007 | Khvorova et al. |
| 2008/0039618 | A1 | 2/2008 | Allerson et al. |

(Continued)

FOREIGN PATENT DOCUMENTS

| | | |
|---|---|---|
| EP | 1752536 | 2/2007 |
| WO | WO 1996/014329 | 5/1996 |

(Continued)

OTHER PUBLICATIONS

"The ALS Association and the Packard Center Partner to Develop Animal Model Systems for Most Common Cause of Familial ALS", http://www.alsa.org/news/archive/new-animal-model-systems.html Mar. 1, 2012 (printed Oct. 23, 2015).

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

(Continued)

*Primary Examiner* — J. E. Angell
(74) *Attorney, Agent, or Firm* — McNeill PLLC

(57) ABSTRACT

Disclosed herein are compositions and methods for reducing expression of C9ORF72 mRNA and protein in an animal. Such methods are useful to treat, prevent, ameliorate, or slow progression of neurodegenerative diseases in an individual in need thereof.

19 Claims, No Drawings

Specification includes a Sequence Listing.

(56) References Cited

U.S. PATENT DOCUMENTS

| | | | |
|---|---|---|---|
| 2009/0012281 A1 | 1/2009 | Swayze et al. | |
| 2010/0216864 A1 | 8/2010 | Staarup et al. | |
| 2012/0083522 A1* | 4/2012 | Monia | A61P 35/00 514/44 R |
| 2012/0149757 A1 | 6/2012 | Krainer et al. | |
| 2012/0214865 A1 | 8/2012 | Bennett et al. | |
| 2013/0035366 A1 | 2/2013 | Swayze et al. | |
| 2014/0255936 A1 | 9/2014 | Rademakers | |
| 2014/0303238 A1 | 10/2014 | Linsley et al. | |
| 2015/0148404 A1 | 5/2015 | de Visser et al. | |
| 2016/0108396 A1 | 4/2016 | Jensen et al. | |
| 2016/0251655 A1 | 9/2016 | Freier et al. | |
| 2016/0304871 A1 | 10/2016 | Rigo | |
| 2017/0349897 A1 | 12/2017 | Rigo | |
| 2018/0318330 A1 | 11/2018 | Prakash et al. | |
| 2019/0142856 A1 | 5/2019 | Bennett et al. | |
| 2019/0264204 A1 | 8/2019 | Rigo | |
| 2019/0367916 A1 | 12/2019 | Freier et al. | |
| 2023/0112920 A1 | 4/2023 | Freier et al. | |

FOREIGN PATENT DOCUMENTS

| | | |
|---|---|---|
| WO | WO 1998/039352 | 9/1998 |
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2005/040180 | 5/2005 |
| WO | WO 2005/113016 | 12/2005 |
| WO | WO 2005/121368 | 12/2005 |
| WO | WO 2007/089584 | 8/2007 |
| WO | WO 2007/131237 | 11/2007 |
| WO | WO 2007/134181 | 11/2007 |
| WO | 2007146511 A2 | 12/2007 |
| WO | WO 2008/076324 | 6/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/007855 | 1/2009 |
| WO | WO 2009/049166 | 4/2009 |
| WO | WO 2010/019270 | 2/2010 |
| WO | WO 2010/148013 | 12/2010 |
| WO | WO 2011/005793 | 1/2011 |
| WO | WO 2011/135396 | 11/2011 |
| WO | 2011156673 A2 | 12/2011 |
| WO | WO 2012/005898 | 1/2012 |
| WO | WO 2012/012443 | 1/2012 |
| WO | WO 2012/087983 | 6/2012 |
| WO | WO 2012/092367 | 7/2012 |
| WO | WO 2012/135736 | 10/2012 |
| WO | WO 2013/030588 | 3/2013 |
| WO | WO 2013/036833 | 3/2013 |
| WO | WO 2013/086207 | 6/2013 |
| WO | 2014062736 A1 | 4/2014 |
| WO | WO 2014/062691 | 4/2014 |
| WO | WO 2015/054676 | 4/2015 |
| WO | WO 2016/024205 | 2/2016 |
| WO | WO 2016/060919 | 4/2016 |
| WO | WO 2016/168592 | 10/2016 |
| WO | WO 2017/079291 | 5/2017 |
| WO | WO 2017/180835 | 10/2017 |

OTHER PUBLICATIONS

Altmann et al., "Second Generation Antisense Oligonucleotides-Inhibition of PKC-60 and c-raf Kinase Expression by Chimeric Oligonucleotides Incorporating 6"-Substituted Carbocyclic Nucleosides and 2"-O-Ethylene Glycol Substituted Ribonucleosides" Nucleosides & Nucleotides. (1997) 16:917-926.

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure-activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Al-Sarraj et al., "p62 positive, TDP-43 negative, neuronal cytoplasmic and intranuclear inclusions in the cerebellum and hippocampus define the pathology of C9orf72-linked FTLD and MND/ALS" Acta Neuropathol (2011) 122:691-702.

Ash et al., "Unconventional Translation of C9ORF72 GGGGCC Expansion Generates Insoluble Ploypeptides Specific to c9FTD/ALS" Neuron (2013) 77(4): 639-646.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Baloh, R.H, "Generation of Non-Integrating iPS Cells and Motor Neurons from C9orf72 Repeat Expansion ALS Patients" 65th AAN Annual Meeting, San Diego, CA, Mar. 16-23, 2013.

Baloh, R.H., "Targeting RNA foci shows a therapeutic effect in iPSC-derived motor neurons from C9orf72 repeat patients" ALSMND meeting, Milan, Dec. 6, 2013.

Baloh, R.H., "Induced Pluripotent stem cell models from C9orf72 patients." Oral presentation, California ALS PAC10 Research Summit, Los Angeles, CA, Nov. 11, 2012.

Baughn et al., "Antisense Oligonucleotide as a Potential Therapy for Amyotrophic Lateral Sclerosis with C9orf72 Expansion" Poster Presentation, Keystone Symposia, New Frontiers in Neurodegenerative Disease Research, Santa Fe, NM, Feb. 3-8, 2013.

Bennett et al., "Antisense oligonucleotides as a tool for gene functionalization and target validation," Biochimica et Biophysica Acta (1999) 1489: 19-30.

Bieniek et al., "Tau pathology in frontotemporal lobar degeneration with C9ORF72 hexanucleotide repeat expansion" Acta Neuropathol (2013) 125(2):289-302.

Boxer et al. "Clinical, neuroimaging and neuropathological features of a new chromosome 9p-linked FTD-ALS family" J. Neurol. Neurosurg. Psychiatry (2011) 82:196-203.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Brettschneider et al., "Microglial activation correlates with disease progression and upper motor neuron clinical symptoms in Amyotrophic Lateral Sclerosis", PLOS One (2012) 7:e39216.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chio et al., "Prevalence of SOD1 mutations in the Italian ALS population" Neurology (2008) 70:533-537.

Ciura et al., "Loss of function of C9orf72 causes motor deficits in a zebrafish model of amyotrophic lateral sclerosis" Ann Neurol (2013) 74(2): 180-187.

Crooke et al., "Basic Principles of Antisense Therapeutics" Antisense Research and Application (1998) Chapter 1:1-50.

Dejesus-Hernandez et al., "Expanded GGGGCC Hexanucleotide Repeat in Noncoding Region of C9ORF72 Causes Chromosome 9p-Linked FTD and ALS" Neuron (2011) 72:245-256.

Donnelly et al., "Development of a C9ORF72 ALS antisense therapy and a therapeutic biomarker" Abstracts of the Society for Neuroscience, Washington, DC, US, Oct. 17, 2012, Retrieved from the Internet Aug. 15, 2016: http://www.abstractsonline.com/Plan/ViewAbstract.aspx?sKey=c4cccfd5-5e4c-4dle-9569-9albleb21d80&cKey=c5c69155-5d2b-467c-8dlf-87299c514c7f&mKey=%7b70007181-01C9-4DE9-A0A2-EEBFA14CD9F1%7d.

Donnelly et al., "Development of C9ORF72 ALS Biomarkers and Therapeutics" American Neurological Association 2012 Annual Meeting, Poster Presentation, Boston, MA Oct. 10, 2012.

Donnelly et al., "Development of C9orf72 ALS Biomarkers and Therapeutics" Annals of Neurology (Oct. 10, 2012) 72(16):S67-S68.

(56) References Cited

OTHER PUBLICATIONS

Donnelly et al., “Limited availability of ZBP1 restricts axonal mRNA localization and nerve regeneration capacity” EMBO J. (2011) 30:4665-4677.
Donnelly et al., “RNA toxicity from the ALS/FTD C9ORF72 expansion is mitigated by antisense intervention” Neuron (2013) 80(2):415-428 [with Supplemental Information].
Donnelly et al., “Transcriptome analysis of C9orf72 ALS patient derived CNS iPS cells and autopsy tissue reveals a unique expression and splicing profile.” Abstracts of the Society for Neuroscience, Washington, DC, US, Oct. 16, 2012, Retrieved from the Internet Aug. 19, 2016: http://www.abstractsonline.com/Plan/ViewAbstract.aspx?sKey=99bd542e-9dff-4338-9756-dfbeb1839aa6&cKey=63d1b086-9f01-43d4-ab3f-d258faa86d9e&mKey=%7b70007181-01C9-4DE9-A0A2-EEBFA14CD9F1%7d.
Donnelly et al., “Transcriptome analysis of C9orf72 ALS patient derived CNS iPS cells and autopsy tissue reveals a unique expression and splicing profile.” Oral Presentation, Neuroscience 2012, Washington, DC, US, Oct. 17, 2012.
Elayadi et al., “Application of PNA and LNA oligomers to chemotherapy” Curr. Opinion Invens. Drugs (2001) 2:558-561.
European Search Report for application No. 13847957.1 dated Jul. 13, 2016.
European Search Report for application No. 13846313.8 dated May 11, 2016.
European Search Report for application No. 13847099.2 dated May 25, 2016.
Extended European Search Report for application No. 14852924.1 dated Jun. 20, 2017.
Extended European Search Report for application No. 16780833.6 dated Nov. 15, 2018.
Fernandes et al., “Oligonucleotide-Based Therapy for FTD/ALS Caused by the C9orf72 Repeat Expansion: A Perspective” Journal of Nucleic Acids (2013) :1-11.
Freier et al., “The ups and downs of nucleic acid duplex stability: structure-stability studies on chemically-modified DNA:RNA duplexes” Nucleic Acids Research (1997) 25(22):4429-4443.
Frieden et al., “Expanding the design horizon of antisense oligonucleotides with alpha-L-LNA” Nucleic Acids Research (2003) 31(21):6365-6372.
Ganesalingam et al., “Combination of neurofiliment heavy chain and complement C3 as CSF biomarkers for ALS” Journal of Neurochemistry (2011) 117: 528-537.
Gautschi et al., “Activity of a novel bcl-2/bcl-xLbispecific antisense oligonucleotide against tumors of diverse histologic origins” J. Natl. Cancer Inst. (2001) 93:463-471.
GenBank: Accession No. NT 008413 Jul. 24, 2012.
GenBank: JU333328.1 TSA: Macaca mulatta Mamu_527777 mRNA sequence. Mar. 26, 2012 (Retrieved from the internet Sep. 12, 2016: http://www.ncbi.nlm.nih.gov/nuccore/380810415?sat=18&satkey=24474174).
Gendron et al., “Poly(GP) proteins are a useful pharmacodynamic marker for C9ORF72-associated amyotrophic lateral sclerosis” Sci Tran Med (2017) 9(383):1-12.
Hirtz et al., “How common are the “common” neurologic disorders?” Neurology (2007) 68:326-337.
Ince et al., “Molecular pathology and genetic advances in amyotrophic lateral sclerosis: an emerging molecular pathway and the significance of glial pathology,” Acta Neuro. (2011) 122:657-671.
International Search Report for application No. PCT/US2013/065073 dated Apr. 22, 2014.
International Search Report for application No. PCT/US2013/065067 dated Jan. 24, 2014.
International Search Report for application No. PCT/US2013/065131 dated Feb. 14, 2014.
International Search Report for application on. PCT/US2014/060194 dated Apr. 14, 2015.
International Search Report for application No. PCT/US17/27355 dated Jul. 26, 2017.
International Search Report for application No. PCT/US2016/060106 dated Feb. 1, 2017.
Jiang et al., “Antisense oligonucleotide therapy for ALS/FTD caused by a gain of toxicity from C9orf72 hexanucleotide expansions.” Poster Presentation, 10th Brain Research Conference, RNA Metabolism in Neurological Disease, Oct. 16, 2015.
Jiang et al. “Gain of Toxicity from ALS/FTG-Linked Repeat Expansions in C9ORF72 Is Alleviated by Antisense Oligonucleotides Targeting GGGCC-Containing RNAs.” Neuron (2016) 90:535-550.
Jeong et al., “Rapid Identification of Monospecific Monoclonal Antibodies Using a Human Proteome Microarray.” Mol. Cell. Proteomics (2012) 11(6): O111.016253-1 to O111.016253-10.
Johnson et al., “Exome sequencing reveals VCP mutations as a cause of familial ALS” Neuron (2010) 68:857-864.
Jones et al., “RNA quantitation by fluorescence-based solution assay: RiboGreen reagent characterization” Analytical Biochemistry (1998) 265(2):368-374.
Klein et al., “Gain of RNA function in pathological cases: Focus on myotonic dystrophy” Biochimie (2011) 93(11):2006-2012.
Koshkin et al., “LNA (locked nucleic acids): Synthesis of the adenine, cytosine, guanine, 5-methylcytosine, thymine and uracil bicyclonucleoside monomers, oligomerisation, and unprecedented nucleic acid recognition” Tetrahedron (1998) 54:3607-3630.
Kumar et al., “The first analogues of LNA (locked nucleic acids): phosphorothioate-LNA and 2'-thio-LNA” Bioorg Med Chem Lett. (1998) 8:2219-2222.
Kurreck “Antisense technologies. Improvement through novel chemical modifications” Eur J Biochem (2003) 270: 1628-1644.
Kwiatkowski et al., “Mutations in the FUS/TLS gene on chromosome 16 cause familial amyotrophic lateral sclerosis” Science (2009) 323:1205-1208.
Laaksovirta et al, “Chromosome 9p21 in amyotrophic lateral sclerosis in Finland: a genome-wide association study” Lancet Neurol. (2010) 9:978-985.
Lagier-Tourenne, et al., “Sense and Antisense RNA Foci in C9-ALS/FTD: More Light in a House of Mirrors.” Poster Presentation, American Neurological Association 2013 Annual Meeting; Oct. 14, 2013.
Lagier-Tourenne, C., “Targeted degradation of sense and antisense C9orf72 nuclear foci as therapy for ALS and FTD” Oral Presentation, 24th International Symposium on ALS/MND, Milan, Dec. 6, 2013.
Lagier-Tourenne, C., “Identifying mechanisms and therapy for ALS/FTD from C9orf72 expansion”, Oral Presentation, ALSA and AFTD Symposium, Society for Neuroscience Annual Meeting, New Orleans; Oct. 15, 2012.
Lagier-Tourenne, C. “Therapy Development for ALS/MND and Frontotemporal Dementia with C9orf72 Expansion: Antisense Oligonucleotide Mediated Reduction in Nuclear RNA Foci.” ALS FD (Nov. 4, 2013) 14(sup2): p. 17.
Lagier-Tourenne et al., “Targeted Degradation of Sense and Antisense C9ORF72 RNA Foci as Therapy for ALS and Frontotemporal Degeneration” PNAS (2013) 110(47):E4530-E4539.
Lee et al., “Antisense Therapy in Neurology” Journal of Personalized Medicine (2013) 3(3): 144-176.
Leumann et al., “DNA Analogues: From Supramolecular Principles to Biological Properties” Bioorganic & Medicinal Chemistry (2002) 10:841-854.
Lillo et al., “Frontotemporal dementia and motor neurone disease: overlapping clinic-pathological disorders” J. Clin. Neurosci. (2009) 16:1131-1135.
Lindquist et al, “Corticobasal and ataxia syndromes widen the spectrum of C9ORF72 hexanucleotide expansion disease.” Clin Genet (2013) 83:279-283.
Madson, “Antisense Against C9ORF72”, http://alsn.mda.org/article/antisense-against-c90rf72 Jul. 1, 2012 (printed Oct. 28, 2015).
Maher et al., “Comparative hybrid arrest by tandem antisense oligodeoxyribonucleotides or oligodeoxyribonucleoside methylphosphonates in a cell-free system” Nucl. Acid. Res. (1998) 16(8):3341-3358.

(56) References Cited

OTHER PUBLICATIONS

Mahoney et al., "Frontotemporal dementia with the C9ORF72 hexanucleotide repeat expansion: clinical, neuroanatomical and neuropathological features" Brain (2012) 135: 736-750.
Margolis et al., "DM2 intronic expansions: evidence for CCUG accumulation without flanking sequence or effects on ZNF9 mRNA processing or protein expression" Hum. Mol. Genet. (2006) 15:1808-1815.
Martin, "New acces to 2'-O-alkylated ribonucleosides and properties of 2'-O-alkylated oligoribonucleotides" Helv. Chim. Acta. (1995) 78:486-504.
Maruyama et al., "Mutations of optineurin in amyotrophic lateral sclerosis" Nature (2010) 465:223-226.
Morita et al., "A locus on chromosome 9p confers susceptibility to ALS and frontotemporal dementia" Neurology (2006) 66:839-844.
Mulders et al., "Triplet-repeat oligonucleotide-mediated reversal of RNA toxicity in myotonic dystrophy" PNAS (2009) 106(33):13915-13920.
Nelson et al., "The unstable repeats—three evolving faces of neurological disease." Neuron (2013) 77(5):825-43.
Neumann et al., "Ubiquitinated TDP-43 in frontotemporal lobar degeneration and amyotrophic lateral sclerosis" Science (2006) 314:130-133.
New England Biolabs 1998/1999 Catalog (cover page and pp. 121 and 284).
O'Rourke et al., "C9orf72 BAC Transgenic Mice Display Typical Pathologic Features of ALS/FTD." Neuron (2015) 88(5):892-901.
Orum et al., "Locked nucleic acids: A promising molecular family for gene-function analysis and antisense drug development" Curr. Opinion Mol. Ther. (2001) 3:239-243.
Ostrow et al., "The C9orf72 ALS mutation causes both increased expression and aberrant splicing og the endothelin-B receptor, and its ligand endothelin-1 is increased in CNS tissue from ALS patients and mutant mice," Abstracts of the Society for Neuroscience (Oct. 17, 2012) 42: p. 1.
Pearson et al., "Familial frontotemporal dementia with amyotrophic lateral sclerosis and a shared haplotype on chromosome 9p" J. Nerol. (2011) 258:647-655.
Rabin et al., "Sporadic ALS has compartment-specific aberrant exon splicing and altered cell-matrix adhesion biology" Hum Mol Genet. (2010) 19(2):313-328.
Ravits, J., "Expanding Neurodegenerations: C9orf72-ALS/FTD" Oral Presentation, ANA Meeting, New Orleans, LA, (Oct. 15, 2013).
Ravits. J., "Regional Spread in ALS: Mechanisms and Pathogenesis." Oral Presentation, 2nd Annual Neuromuscular Colloquium, UC Irvine, Newport Beach, CA, May 4, 2012.
Renton et al., "A Hexanucleotide Repeat Expansion in C9ORF72 Is the Cause of Chromosome 9p21-Linked ALS-FTD" Neuron (2011) 72:257-268.
Reynolds et al., "Rational siRNA design for RNA interference" Nature Biotechnology (2004) 22(3):326-330.
Riboldi et al., "Antisense Oligonucleotide Therapy for the Treatment of C9ORF72 ALS/FTD Diseases." Mol Neurobiol (2014) 50:721-732.
Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 14, 2015.
Rosen et al., "Mutations in Cu/Zn superoxide dismutase gene are associated with familial amyotrophic lateral sclerosis" Nature (1993) 362:59-62.
Rowland et al., "Amyotrophic lateral sclerosis" N. Engl. J. Med. (2001) 344(22):1688-1700.
Sareen et al., "Targeting RNA foci shows a therapeutic effect in iPSC-derived motor neurons from C9orf72 repeat patients." ALS FD (Nov. 4, 2013) 14(sup2): pp. 16-17.
Sareen et al., "Targeting RNA foci in iPSC-derived motor neurons from ALS patients with a C9ORF72 repeat expansion." Sci Tran Med (2013) 5(208): 1-13.
Sanghvi et al., "Heterocyclic Base Modifications in Nucleic Acids and Their Applications in Antisense Oligonucleotides" Antisense Research and Applications (1993) pp. 273-288.
Sha et al., "Treatment implications of C9ORF72" Alzheimers Res Ther (2012) 4(6): 46.
Shao et al., "Rational design and rapid screening of antisense oligonucleotides for prokaryotic gene modulation" Nucleic Acids Res (2006) 34: 5660-5669.
Singh et al., "LNA (locked nucleic acids): synthesis and high-affinity nucleic acid recognition" Chem. Commun. (1998) 4:455-456.
Singh et al., "Synthesis of 2'-amino-LNA: A novel conformationally restricted high-affinity oligonucleotide analogue with a handle" J. Org. Chem. (1998) 63: 10035-10039.
Simon-Sanchez et al., "The clinical and pathological phenotype of C9OFR72 hexanucleotide repeat expansions", Brain: Journal of Neurology (2012) 135:723-735.
Smith et al., "Comparison of biosequences" Adv. Appl. Math. (1981) 2(4):482-489.
Sohail et al., "Selecting optimal antisense reagents" Ady Drug Deliv Rev (2000) 44: 23-34.
Sreedharan et al., "TDP-43 mutations in familial and sporadic amyotrophic lateral sclerosis" Science (2008) 319:1668-1672.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Thomsen, "Dramatically improved RNA in 1-15 situ hybridization signals using LNA-modified probes" RNA (2005) 11(11): 1745-1748.
Todd et al. "RNA mediated neurodegeneration in repeat expansion disorders," Annals of Neurology (2009) 67(3):291-300.
Vance et al., "Familial amyotrophic lateral sclerosis with frontotemporal dementia is linked to a locus on chromosome 9p13.2-21.3" Brain (2006) 129:868-876.
Wahlestedt et al., "Potent and nontoxic antisense oligonucleotide containing locked nucleic acids" Proc. Natl. Acad. Sci. USA (2000) 97: 5633-5638.
Watts et al., "Silencing disease genes in the laboratory and the clinic" J Pathol (2012) 226(2): 365-379.
Wojciechowska et al., "Cellular toxicity of expanded RNA repeats: focus on RNA foci" Human Molecular Genetics (2011) 1-11.
Woolf et al., "Specificity of antisense oligonucleotides in vivo" PNAS (1992) 89: 7305-7309.
Zhang et al., "PowerBLAST: A New Network BLAST Application for Interactive or Automated Sequence Analysis and Annotation" Genome Res. (1997) 7:649-656.
Zhang et al., "The C9orf72 repeat expansion disrupts nucleocytoplasmic transport." Nature (2015) 525(7567):56-61.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Wheeler et al., "Targeting nuclear RNA for in vivo correction of myotonic dystrophy" Nature (2012) 488: 111-117.
Lee et al., "Rnase H-mediated degradation of toxic RNA in myotonic dystrophy type 1" PNAS (2012) 109: 4221-4226.
Cook "Medicinal Chemistry of Antisense Oligonucleotides" Chapter 2—Medicinal Chemistry of Antisense Oligonucleotides, Antisense Drug Technology, 1st Edition (2001).
Boeve et al., "Characterization of frontotemporal dementia and/or amyotrophic lateral sclerosis associated with the GGGGCC repeat expansion in C9ORF72" Brain (2012) 135: 765-783.
Extended European Search Report for EP 22197003.1 dated Jun. 30, 2023, 19 pages.
Partial European Search Report for EP 22197003.1 dated Mar. 2, 2023, 19 pages.
Mori et al., "Bidirectional transcripts of the expanded C9orf72 hexanucleotide repeat are translated into aggregating dipeptide repeat proteins" Acata Neuropathol (2013) 126: 881-893.
GenBank Accession No. NG_031977.1, *Homo sapiens* chromosome 9 open reading frame 72 (C9orf72), RefSeqGene on chromosome 9 (available Mar. 28, 2013), 10 pages.

(56) References Cited

OTHER PUBLICATIONS

Gendron et al., "c9RAN translation: a potential therapeutic target for the treatment of amyotrophic lateral sclerosis and frontotemporal dementia," Expert Opinion on Therapeutic Targets (2013) 17: 991-995.
GeneToolsLLC "Morpholino Antisense Oligos" p. 1-2 available Jan. 7, 2012, according to Wayback Machine (2012).
Ho et al., "Modification of phosphorothioate oligonucleotides yields potent analogs with minimal toxicity for antisense experiments in the CNS," Molecular Brain Res (1998) 62: 1-11.
Kole et al., "RNA therapeutics: beyond RNA interference and antisense oligonucleotides," Nature Reviews Drug Discovery (2012) 11: 125-140.
Ostergaard et al., "Rational design of antisense oligonucleotides targeting single nucleotide polymorphisms for potent and allele selective suppression of mutant Huntingtin in the CNS," Nucl Acids Res (2013) 41: 9634-9650.

* cited by examiner

COMPOSITIONS FOR MODULATING C9ORF72 EXPRESSION

SEQUENCE LISTING

The present application is being filed along with a Sequence Listing in electronic format. The Sequence Listing is provided as a file entitled BIOL0269USC2SEQ_ST25.txt created Oct. 16, 2018, which is 104 Kb in size. The information in the electronic format of the sequence listing is incorporated herein by reference in its entirety.

FIELD

Provided are compositions and methods for modulating expression of C9ORF72 mRNA and protein in cells and animals. Such compositions and methods are useful to treat, prevent, ameliorate, or slow progression of neurodegenerative diseases, including amyotrophic lateral sclerosis (ALS), frontotemporal dementia (FTD), corticobasal degeneration syndrome (CBD), atypical Parkinsonian syndrome, and olivopontocerebellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). The mutation in the C9ORF72 gene is the most common genetic cause of ALS and FTD. The ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C90RF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

A founder haplotype, covering the C9ORF72 gene, is present in the majority of cases linked to this region.

There are currently no effective therapies to treat such neurodegenerative diseases. Therefore, it is an object to provide compositions and methods for the treatment of such neurodegenerative diseases.

SUMMARY

Certain embodiments provide methods, compounds, and compositions for inhibiting expression of C9ORF72 mRNA and protein in cells, tissues, and animals. Certain embodiments provide methods, compounds, and compositions for reducing C9ORF72 mRNA and protein levels in cells, tissues, and animals. Certain embodiments provide antisense compounds targeted to a C9ORF72 nucleic acid. In certain embodiments, the antisense compounds are modified oligonucleotides. In certain embodiments, the modified oligonucleotides are single-stranded.

In certain embodiments, C9ORF72 associated Repeat Associated Non-ATG Translation (RAN translation) products are reduced. In certain embodiments, the C9ORF72 associated RAN translation products are poly-(glycine-proline), poly-(glycine-alanine), and poly-(glycine-arginine). In certain embodiments, certain C9ORF72 mRNA variants are preferentially reduced. In certain embodiments, the C9ORF72 mRNA variants preferentially reduced are variants processed from a pre-mRNA containing intron 1. In certain embodiments, intron 1 contains a hexanucleotide repeat expansion. In certain embodiments, the C9ORF72 mRNA variant preferentially reduced is a C9ORF72 pathogenic associated mRNA variant. In certain embodiments, the C9ORF72 pathogenic associated mRNA variant is NM_001256054.1 (SEQ ID NO: 1). In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 30 GGGGCC repeats, more than 30 GGGGCC repeats, more than 100 GGGGCC repeats, more than 500 GGGGCC repeats, or more than 1000 GGGGCC repeats. In certain embodiments, the hexanucleotide repeat expansion is associated with nuclear foci. In certain embodiments, C9ORF72 associated RAN translation products are associated with nuclear foci. In certain embodiments, the C9ORF72 associated RAN translation products are are poly-(glycine-proline), poly-(glycine-alanine), and poly-(glycine-arginine). In certain embodiments, the compositions and methods described herein are useful for reducing C9ORF72 mRNA levels, C9ORF72 protein levels, C9ORF72 RAN translation products, and nuclear foci. In certain embodiments, the compositions and methods described herein are useful for selectively reducing C9ORF72 pathogenic associated mRNA variants. Such reduction can occur in a time-dependent manner or in a dose-dependent manner.

Also provided are methods useful for preventing, treating, ameliorating, and slowing progression of diseases associated with C9ORF72. In certain embodiments, such C9ORF72 associated diseases are neurodegenerative diseases. In certain embodiments, the neurodegenerative disease is amyotrophic lateral sclerosis (ALS), frontotemporal dementia (FTD), corticobasal degeneration syndrome (CBD), atypical Parkinsonian syndrome, and olivopontocerebellar degeneration (OPCD).

Such diseases can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 antisense compound to an individual in need thereof. In certain embodiments, the antisense compound is a single-stranded modified oligonucleotide. In certain embodiments, the single-stranded modified oligonucleotide is complementary to a C9ORF72 nucleic acid.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise. Compounds of the invention include variations of the disclosed compounds in which one or more hydrogen, carbon, nitrogen, oxygen, or sulfur atoms is replaced with a stable isotope of the same element.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings: "2'—O—methoxyethyl" (also 2'-MOE and 2'—$OCH_2CH_2$—$OCH_3$ and MOE) refers to an O-methoxy-ethyl modification of the 2' position of a furanose ring. A 2'—O—methoxyethyl modified sugar is a modified sugar.

"2'-MOE nucleoside" (also 2'—O—methoxyethyl nucleoside) means a nucleoside comprising a MOE modified sugar moiety.

"2'-substituted nucleoside" means a nucleoside comprising a substituent at the 2'-position of the furanose ring other than H or OH. In certain embodiments, 2'-substituted nucleosides include nucleosides with bicyclic sugar modifications.

"5-methylcytosine" means a cytosine modified with a methyl group attached to the 5' position. A 5-methylcytosine is a modified nucleobase.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the severity of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson- Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 antisense transcript" means transcripts produced from the non-coding strand (also antisense strand and template strand) of the C9ORF72 gene. The C9ORF72 antisense transcript differs from the canonically transcribed "C9ORF72 sense transcript", which is produced from the coding strand (also sense strand) of the C9ORF72 gene. In certain embodiments, a C9ORF72 antisense transcript is SEQ ID NO: 18.

"C9ORF72 antisense transcript specific inhibitor" refers to any agent capable of specifically inhibiting the expression of C9ORF72 antisense transcript and/or its expression products at the molecular level. As used herein, "specific" means reducing or inhibiting expression of C9ORF72 antisense transcript without reducing non-target transcript to an appreciable degree (e.g., a C9ORF72 antisense transcript specific inhibitor reduces expression of C9ORF72 antisense transcript, but does not reduce expression of C9ORF72 sense transcript to an appreciable degree). C9ORF72 specific antisense transcript inhibitors include antisense compounds, siRNAs, aptamers, antibodies, peptides, small molecules, and other agents capable of inhibiting the expression of C9ORF72 antisense transcript and/or its expression products, such as C9ORF72 antisense transcript associated RAN translation products.

"C9ORF72 associated disease" means any disease associated with any C9ORF72 nucleic acid or expression product thereof. Such diseases may include a neurodegenerative disease. Such neurodegenerative diseases may include ALS and FTD. In certain embodiments, the C9ORF72 associated disease is caused by (or is associated with) a hexanucleotide repeat expansion. In certain embodiments, the hexanucleotide repeat expansion may comprise GGGGCC, GGGGGG, GGGGGC, or GGGGCG repeated at least 30 times, more than 30 times, more than 100 times, more than 500 times, or more than 1000 times.

"C9ORF72 associated RAN translation products" means aberrant peptide or di-peptide polymers translated through RAN translation (i.e., repeat-associated, and non-ATG-dependent translation). In certain embodiments, the C9ORF72 associated RAN translation products are any of poly-(glycine-proline), poly-(glycine-alanine), and poly-(glycine-arginine).

"C9ORF72 nucleic acid" means any nucleic acid encoding C9ORF72. For example, in certain embodiments, a C9ORF72 nucleic acid includes a DNA sequence encoding C9ORF72, an RNA sequence transcribed from DNA encoding C9ORF72 including genomic DNA comprising introns and exons (i.e., pre-mRNA), and an mRNA sequence encoding C9ORF72. "C9ORF72 mRNA" means an mRNA encoding a C9ORF72 protein.

"C9ORF72 pathogenic associated mRNA variant" means the C9ORF72 mRNA variant processed from a C9ORF72 pre-mRNA variant containing the hexanucleotide repeat. A C9ORF72 pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). In certain embodiments, the level of a C9ORF72 pathogenic associated mRNA variant is measured to determine the level of a C9ORF72 pre-mRNA containing the hexanucleotide repeat in a sample.

"C9ORF72 specific inhibitor" refers to any agent capable of specifically inhibiting the expression of C9ORF72 mRNA and/or C9ORF72 protein at the molecular level. For example, C9ORF72 specific inhibitors include nucleic acids (including antisense compounds), siRNAs, aptamers, antibodies, peptides, small molecules, and other agents capable of inhibiting the expression of C9ORF72 mRNA and/or C9ORF72 protein. Similarly, in certain embodiments, C9ORF72 specific inhibitors may affect other molecular processes in an animal.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'—$CH(CH_3)$—O—2'.

"Constrained ethyl nucleoside" (also cEt nucleoside) means a nucleoside comprising a bicyclic sugar moiety comprising a 4'—$CH(CH_3)$—O—2' bridge.

"Chemically distinct region" refers to a region of an antisense compound that is in some way chemically different than another region of the same antisense compound. For example, a region having 2'—O—methoxyethyl nucleosides is chemically distinct from a region having nucleosides without 2'—O—methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Focus" or "foci" means a nuclear or cytoplasmic body comprising a C9ORF72 transcript. In certain embodiments, a focus comprises at least one C9ORF72 transcript. In certain embodiments, C9ORF72 foci comprise transcripts comprising any of the following hexanucleotide repeats: GGGGCC, GGGGGG, GGGGGC, and/or GGGGCG.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support Rnase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Hexanucleotide repeat expansion" means a series of six bases (for example, GGGGCC, GGGGGG, GGGGCG, or GGGGGC) repeated at least twice. In certain embodiments, the hexanucleotide repeat expansion may be located in intron 1 of a C9ORF72 nucleic acid. In certain embodiments, a pathogenic hexanucleotide repeat expansion includes at least 30, more than 30, more than 100, more than 500, or more than 1000 repeats of GGGGCC, GGGGGG, GGGGCG, or GGGGGC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 23 or fewer repeats of GGGGCC, GGGGGG, GGGGCG, or GGGGGC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target. "Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy. "Inhibiting C9ORF72" means reducing the level or expression of a C9ORF72 mRNA and/or protein. In certain embodiments, C9ORF72 mRNA and/or protein levels are inhibited in the presence of an antisense compound targeting C9ORF72, including an antisense oligonucleotide targeting C9ORF72, as compared to expression of C9ORF72 mRNA and/or protein levels in the absence of a C9ORF72 antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'—$CH_2$—O—2') LNA, (B) β-D-Methyleneoxy (4'—$CH_2$—O—2') LNA, (C) Ethyleneoxy (4'—$(CH_2)_2$—O—2') LNA, (D) Aminooxy (4'—$CH_2$—O—N®-2') LNA and (E) Oxyamino (4'—$CH_2$-N®—O—2') LNA, as depicted below.

(A)

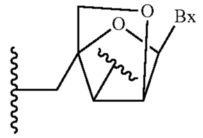

(B)

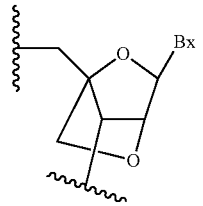

(C)

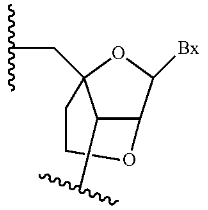

-continued (D)

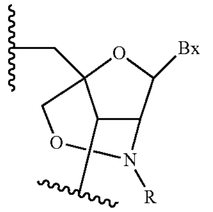

(E)

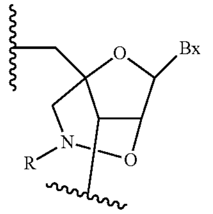

As used herein, LNA compounds include, but are not limited to, compounds having at least one bridge between the 4' and the 2' position of the sugar wherein each of the bridges independently comprises 1 or from 2 to 4 linked groups independently selected from $—[C(R_1)(R_2)]_n—$, $—C(R_1)═C(R_2)—$, $—C(R_1)═N—$, $—C(═NR_1)—$, $—C(═O)—$, $—C(═S)—$, $—O—$, $—Si(R_1)_2—$, $—S(═O)_x$-and $—N(R_1)—$; wherein: x is 0, 1, or 2; n is 1, 2, 3, or 4; each $R_1$ and $R_2$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl $(S(═O)_2$-$J_1)$, or sulfoxyl $(S(═O)—J_1)$; and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl or a protecting group.

Examples of 4'-2' bridging groups encompassed within the definition of LNA include, but are not limited to one of formulae: $—[C(R_1)(R_2)]_n—$, $—[C(R_1)(R_2)]_n—O—$, $—C(R_1R_2)—N(R_1)—O—$ or $—C(R_1R_2)—O—N(R_1)—$. Furthermore, other bridging groups encompassed with the definition of LNA are 4'—$CH_2$-2', 4'—$(CH_2)_2$-2', 4'—$(CH_2)$ 3-2', 4'—$CH_2$—O—2', 4'—$(CH_2)_2$—O—2', 4'—$CH_2$—O—N($R_1$)-2' and 4'—$CH_2$—N($R_1$)—O—2'-bridges, wherein each $R_1$ and $R_2$ is, independently, H, a protecting group or $C_1$-$C_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'—$CH_2$—O—2') bridge to form the bicyclic sugar moiety. The bridge can also be a methylene (—$CH_2$—) group connecting the 2' oxygen atom and the 4' carbon atom, for which the term methyleneoxy (4'—$CH_2$—O—2') LNA is used. Furthermore; in the case of the bicylic sugar moiety having an ethylene bridging group in this position, the term ethyleneoxy (4'—$CH_2CH_2$—O—2') LNA is used. A-L-methyleneoxy (4'—$CH_2$—O—2'), an isomer of methyleneoxy (4'—$CH_2$—O—2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleoside in an antisense compound. "Natural sugar moiety" means a sugar moiety found in DNA (2'-H) or RNA (2'—OH).

"Naturally occurring internucleoside linkage" means a 3' to 5' phosphodiester linkage. "Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O—or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid. "Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins. "Pharmaceutical agent" means a substance that provides a therapeutic benefit when administered to an individual. For example, in certain embodiments, an antisense oligonucleotide targeted to C9ORF72 is a pharmaceutical agent.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked)„ucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form within the body or cells thereof by the action of endogenous enzymes or other chemicals or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents. "Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid. "Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand. A "single-stranded modified oligonucleotide" means a modified oligonucleotide which is not hybridized to a complementary strand. "Sites," as used herein, are defined as unique nucleobase positions within a target nucleic acid.

"Slows progression" means decrease in the development of the disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect. "Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" or "treatment" means administering a composition to effect an alteration or improvement of a disease or condition.

"Unmodified nucleobases" means the purine bases adenine (A) and guanine (G), and the pyrimidine bases (T), cytosine (C), and uracil (U).

"Unmodified nucleotide" means a nucleotide composed of naturally occuring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside). "Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide compositions and methods for reducing total C9ORF72 mRNA and protein expression.

Certain embodiments provide compositions and methods for reducing C9ORF72 pathogenic associated mRNA variants.

Certain embodiments provide methods for the treatment, prevention, amelioration, or slowing progression of diseases associated with C9ORF72 in an individual in need thereof. Also contemplated are methods for the preparation of a medicament for the treatment, prevention, or amelioration of a disease associated with C9ORF72. C9ORF72 associated diseases include neurodegenerative diseases. In certain embodiments, the neurodegenerative disease may be ALS or FTD. In certain embodiments, the neurodegenerative disease may be familial or sporadic. The present disclosure provided the following non-limiting numbered embodiments:

Embodiment 1. A compound comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID Nos: 22-55.

Embodiment 2. The compound of embodiment 1, wherein the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1 or SEQ ID NO: 2.

Embodiment 3. The compound of embodiments 1 and 2, wherein the modified oligonucleotide is a single-stranded modified oligonucleotide.

Embodiment 4. The compound of any of embodiments 1-3, wherein the modified oligonucleotide comprises at least one modified internucleoside linkage.

Embodiment 5. The compound of embodiment 4, wherein the at least one modified internucleoside linkage is a phosphorothioate internucleoside linkage.

Embodiment 6. The compound of embodiments 4 and 5, wherein the modified oligonucleotide comprises at least one phosphodiester linkage.

Embodiment 7. The compound of embodiment 5, wherein each modified internucleoside linkage is a phosphorothioate internucleoside linkage.

Embodiment 8. The compound of any of embodiments 1-7, wherein at least one nucleoside comprises a modified nucleobase.

Embodiment 9. The compound of embodiment 8, wherein the modified nucleobase is a 5-methylcytosine.

Embodiment 10. The compound of any of embodiments 1-9, wherein at least one nucleoside of the modified oligonucleotide comprises a modified sugar.

Embodiment 11. The compound of embodiment 10, wherein each nucleoside of the modified oligonucleotide comprises a modified sugar.

Embodiment 12. The compound of embodiments 10 or 11, wherein the at least one modified sugar is a bicyclic sugar.

Embodiment 13. The compound of embodiment 12, wherein the bicyclic sugar comprises a chemical bridge between the 4' and 2' positions of the sugar, wherein the chemical bridge is selected from: 4'—CH®—O—2' and 4'—$(CH_2)_2$—O—2', wherein R is independently H, $C_1$-$C_6$ alkyl, and $C_1$-$C_6$ alkoxy.

Embodiment 14. The compound of embodiment 13, wherein the chemical bridge is 4'—CH®—O—2' and wherein R is methyl.

Embodiment 15. The compound of embodiment 13, wherein the chemical bridge is 4'—CH®—O—2' and wherein R is H.

Embodiment 16. The compound of embodiment 13, wherein the chemical bridge is 4'—CH®—O—2' and wherein R is —$CH_2$—O—$CH_3$.

Embodiment 17. The compound of embodiments 10 or 11, wherein the at least one modified sugar comprises a 2'—O—methoxyethyl group.

Embodiment 18. The compound of any of embodiments 1-10 or 12-16, wherein the modified oligonucleotide is a gapmer.

Embodiment 19. The compound of embodiment 18, wherein the gapmer is any of a 3-8-7 MOE gapmer, a 3-10-7 MOE gapmer, a 4-8-6 MOE gapmer, a 4-10-6 MOE gapmer, a 6-10-4 MOE gapmer, a 6-8-4 MOE gapmer, a 7-8-3 MOE gapmer, or a 7-10-3 MOE gapmer.

Embodiment 20. The compound of claim 5, wherein the modified oligonucleotide comprises internucleoside linkages in any of the following patterns: soosssssssssssooooss, sosssssssssooooss, or sooooossssssssssss, wherein, s=a phosphorothioate linkage, and o=a phosphodiester linkage.

Embodiment 19. A composition comprising the compound of any preceding embodiment or salt thereof and at least one of a pharmaceutically acceptable carrier or diluent.

Embodiment 20. The composition of embodiment 19, further comprising a C9ORF72 antisense transcript specific inhibitor.

Embodiment 21. The composition of embodiment 20, wherein the C9ORF72 antisense transcript specific inhibitor is an antisense compound.

Embodiment 22. The composition of embodiment 21, wherein the antisense compound is a modified oligonucleotide.

Embodiment 23. The composition of embodiment 22, wherein the modified oligonucleotide is single-stranded.

Embodiment 24. The composition of embodiments 22 or 23, wherein the modified oligonucleotide has a nucleobase sequence that is at least 80%, at least 85%, at least 90%, at least 91%, at least 92%, at least 93%, at least 94%, at least 95%, at least 96%, at least 97%, at least 98%, at least 99%, or 100% complementary to a C9ORF72 antisense transcript.

Embodiment 25. The composition of embodiment 24, wherein the C9ORF72 antisense transcript has the nucleobase sequence of SEQ ID NO: 18.

Embodiment 26. A method comprising administering to an animal the compound or composition of any preceding embodiment.

Embodiment 27. The method of embodiment 26, wherein the animal is a human.

Embodiment 28. The method of embodiments 26 and 27, wherein administering the compound prevents, treats, ameliorates, or slows progression of a C9ORF72 associated disease.

Embodiment 29. The method of embodiment 28, wherein the C9ORF72 associated disease is caused by a hexanucleotide repeat expansion.

Embodiment 30. The method of embodiment 28, wherein the C9ORF72 associated disease is amyotrophic lateral sclerosis (ALS), frontotemporal dementia (FTD), corticobasal degeneration syndrome (CBD), atypical Parkinsonian syndrome, and olivopontocerebellar degeneration (OPCD).

Embodiment 31. The method of embodiments 26-30, wherein the administering reduces nuclear foci.

Embodiment 32. The method of embodiments 26-31, wherein the administering reduces expression of C9ORF72 associated RAN translation products.

Embodiment 33. The method of embodiment 32, wherein the C9ORF72 associated RAN translation products are any of poly-(glycine-proline), poly-(glycine-alanine), and poly-(glycine-arginine).

Embodiment 34. Use of the compound or composition of any of embodiments 1-33 for the manufacture of a medicament for treating a neurodegenerative disorder.

Embodiment 35. A compound consisting of a modified oligonucleotide according to the following formula, or a salt thereof:

(SEQ ID NO: 33)

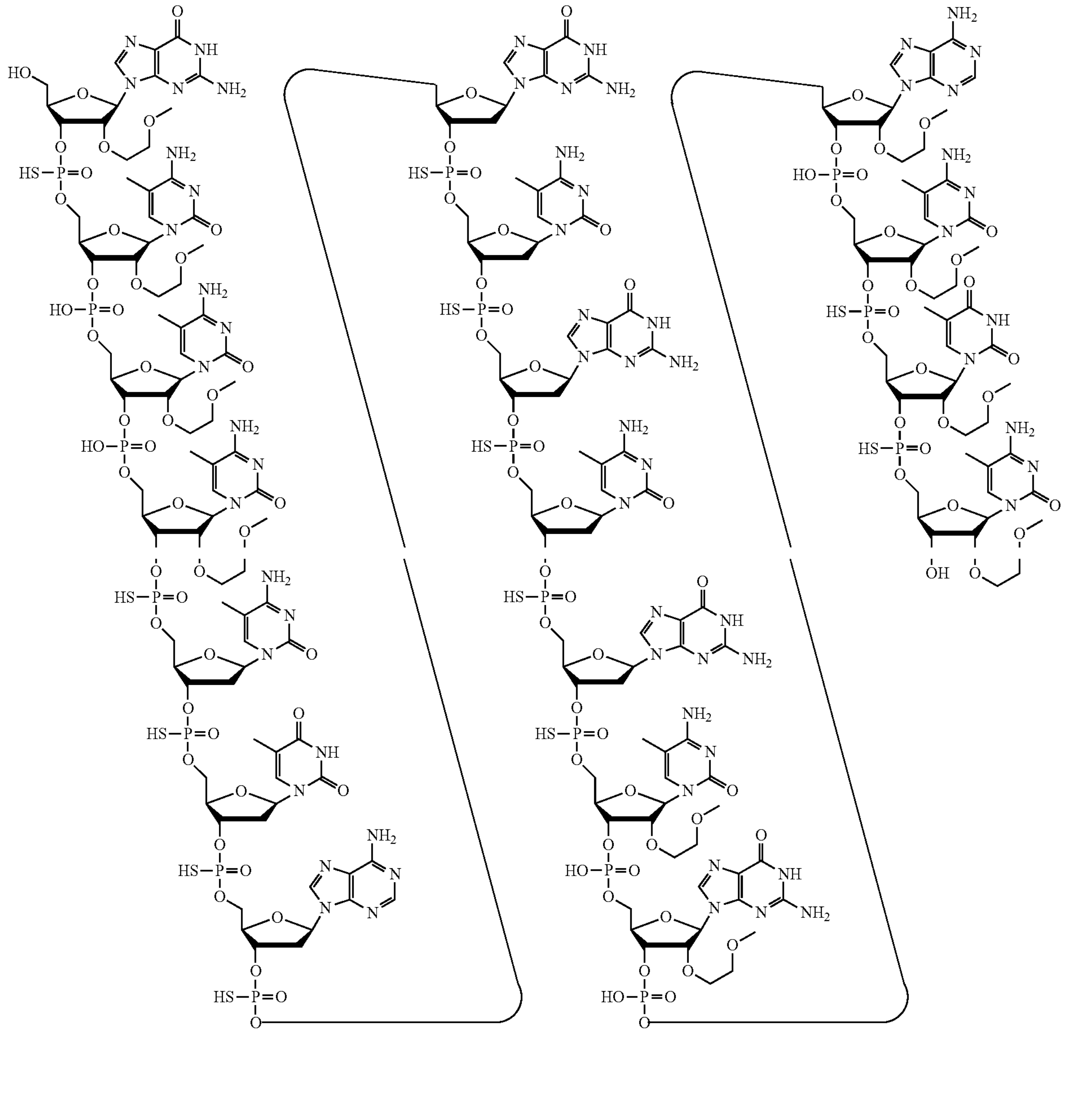

Embodiment 36. A composition consisting of the sodium salt of a modified oligonucleotide according to the following formula:
(SEQ ID NO: 33)
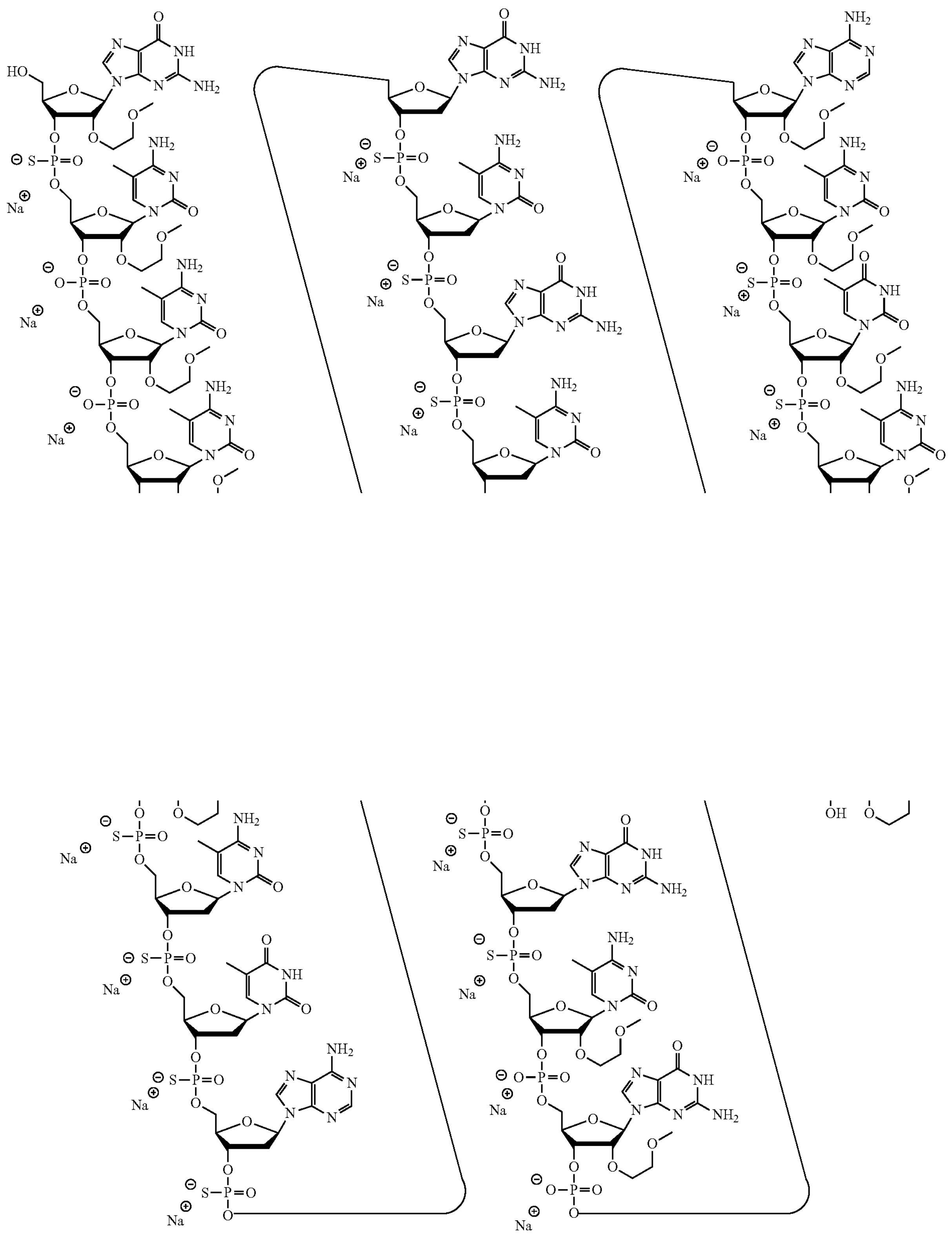

Embodiment 37. A compound consisting of a modified oligonucleotide according to the following formula, or a salt thereof:
(SEQ ID NO: 49)
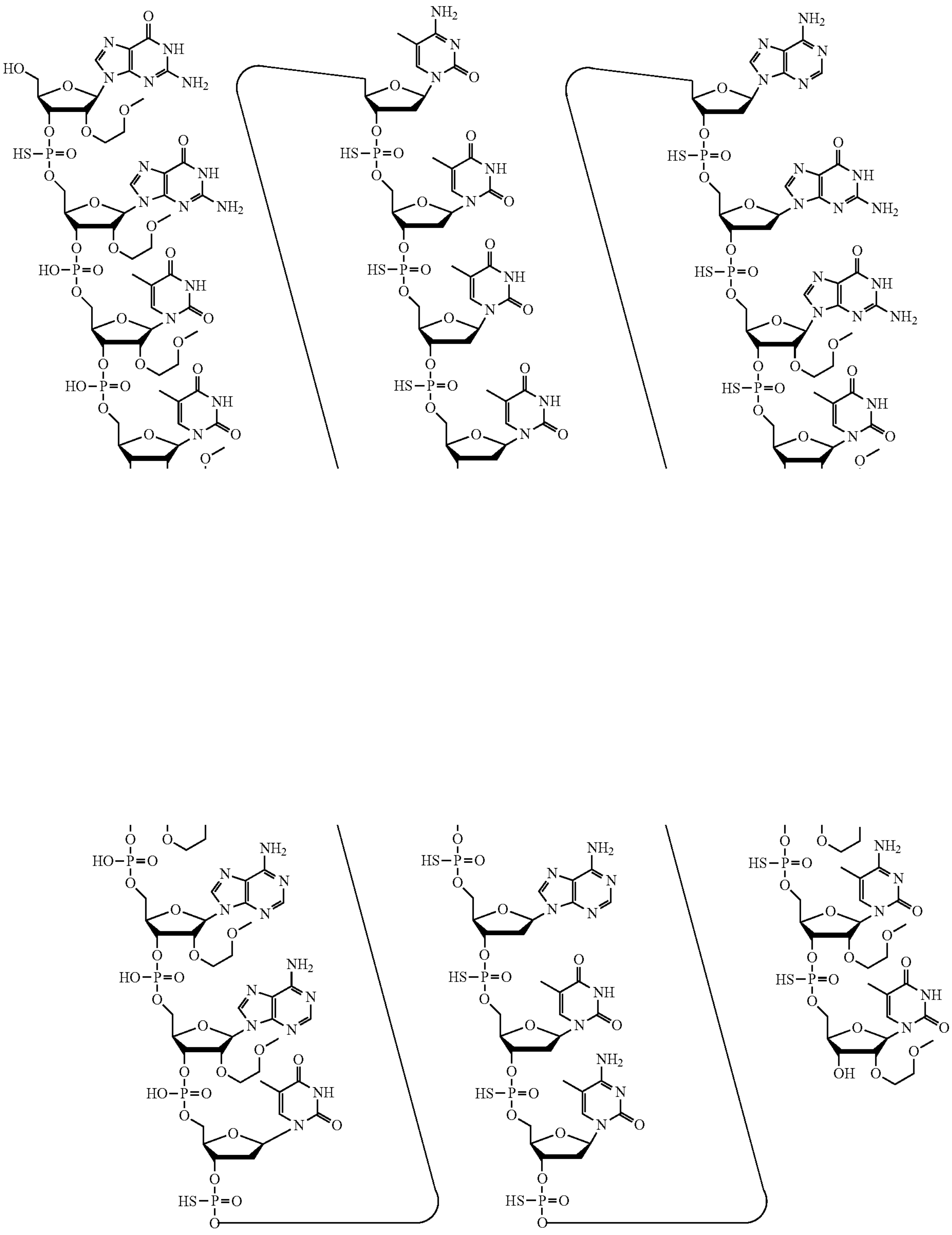

Embodiment 38. A composition consisting of the sodium salt of a modified oligonucleotide according to the following formula:
(SEQ ID NO: 49)
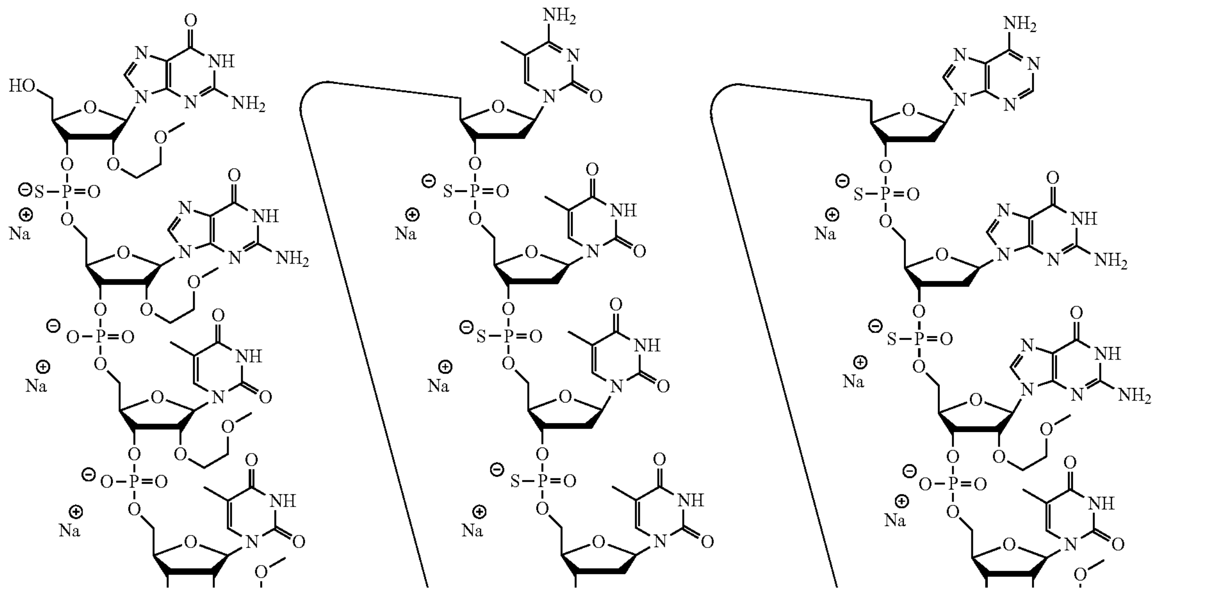
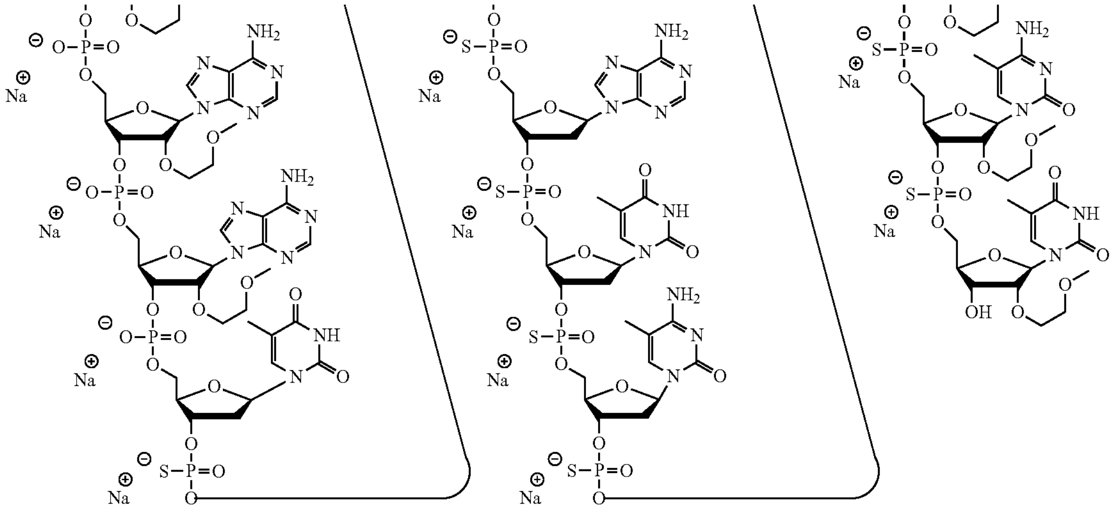

Embodiment 39. A compound consisting of a modified oligonucleotide according to the following formula, or a salt thereof:
(SEQ ID NO: 47)
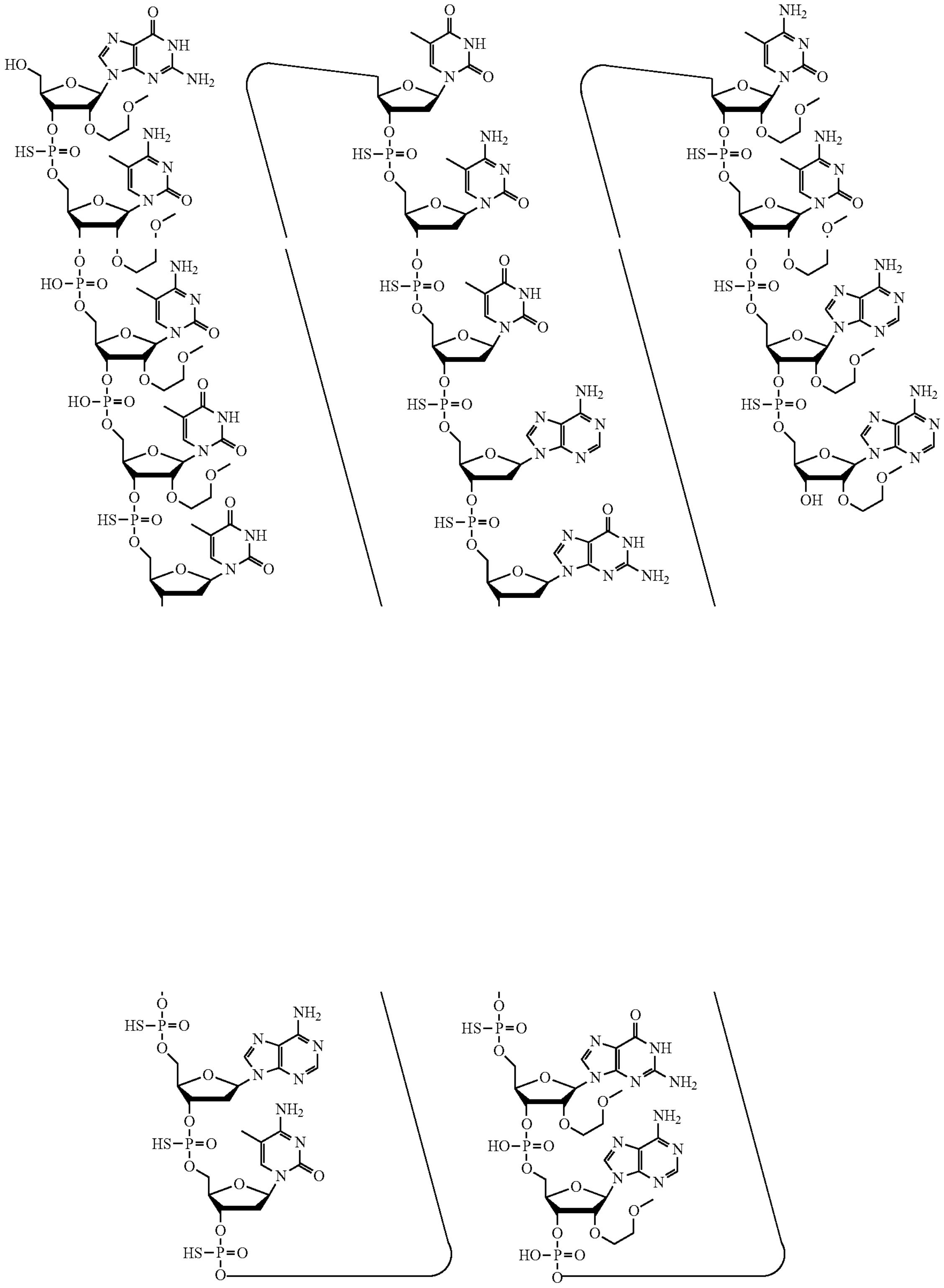

Embodiment 40. A composition consisting of the sodium salt of a modified oligonucleotide according to the following formula:
(SEQ ID NO: 47)
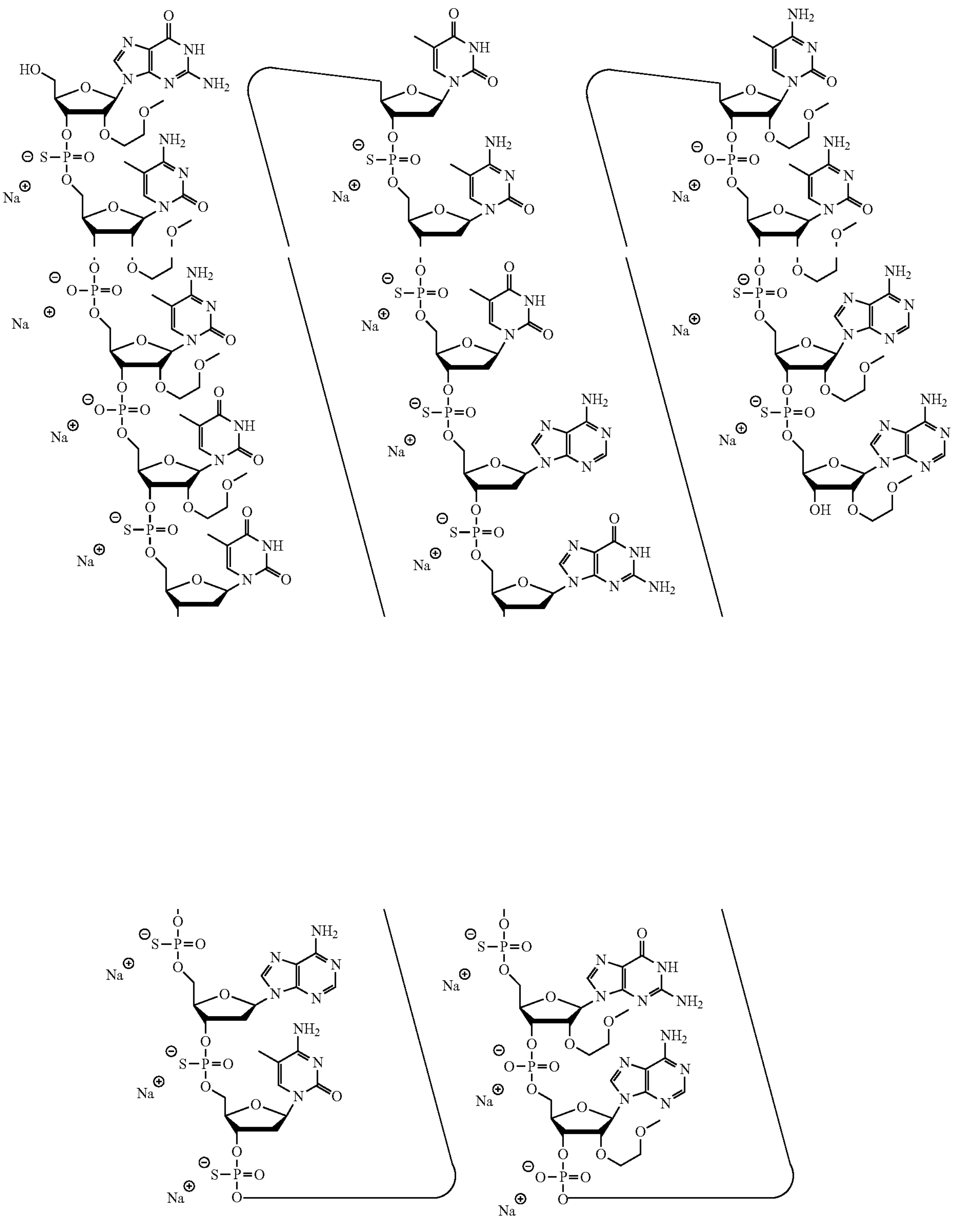

Embodiment 41. A compound consisting of a modified oligonucleotide according to the following formula, or a salt thereof:
(SEQ ID NO: 21)
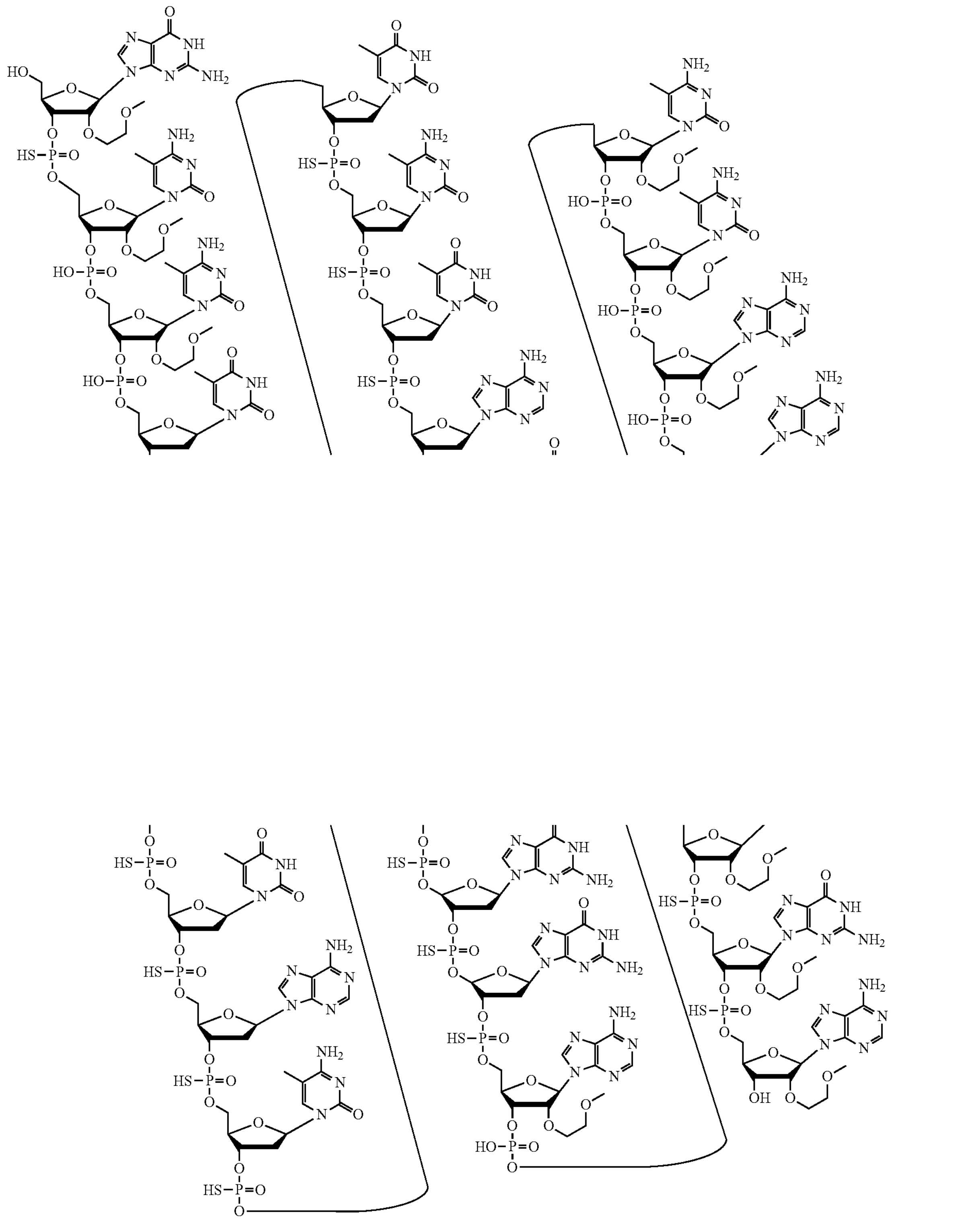

Embodiment 42. A composition consisting of the sodium salt of a modified oligonucleotide according to the following formula:

(SEQ ID NO: 21)

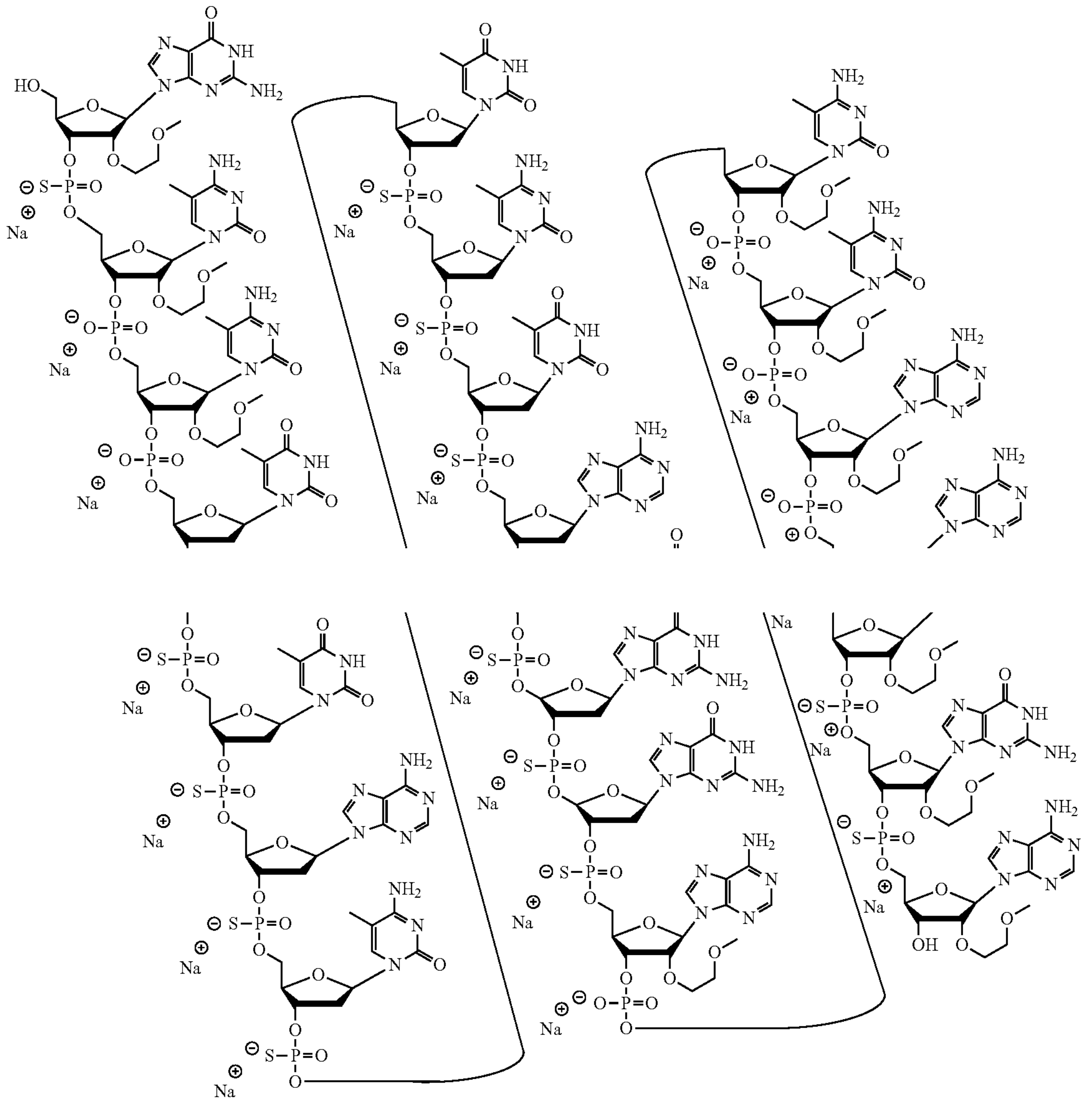

Embodiment 43. The compound or composition of any of embodiments 1-25 or 35-42, wherein the compound or composition is capable of reducing human C9ORF72 mRNA or protein expression in a mammal.

Embodiment 44. The compound or composition of any of embodiments 1-25 or 35-42, wherein the compound or composition is capable of ameliorating at least one symptom of amyotrophic lateral sclerosis (ALS), frontotemporal dementia (FTD), corticobasal degeneration syndrome (CBD), atypical Parkinsonian syndrome, or olivopontocerebellar degeneration (OPCD).

Embodiment 45. The compound or composition of embodiment 44, wherein the symptom of ALS is any of motor deficit, anxiety, and denervation.

Embodiment 46. The compound or composition of any of embodiments 1-25 or 35-42, wherein the compound or composition is capable of delaying progression of disease.

Embodiment 47. The compound or composition of any of embodiments 1-25 or 35-42, wherein the compound or composition is capable of extending survival.

Embodiment 48. The compound or composition of any of embodiments 1-25 or 35-42, wherein the compound or composition is capable of reducing C9ORF72 associated RAN translation products.

Embodiment 49. The compound or composition of any of embodiments 1-25 or 35-42, wherein the compound or composition is capable of selectively reducing C9ORF72 pathogenic associated mRNA variants.

Embodiment 50. The compound or composition of any of embodiments 1-25 or 35-42, wherein the compound or composition is capable of reducing nuclear foci.

Embodiment 51. A compound consisting of a modified oligonucleotide according to the following formula, or a salt thereof:

(SEQ ID NO: 33)

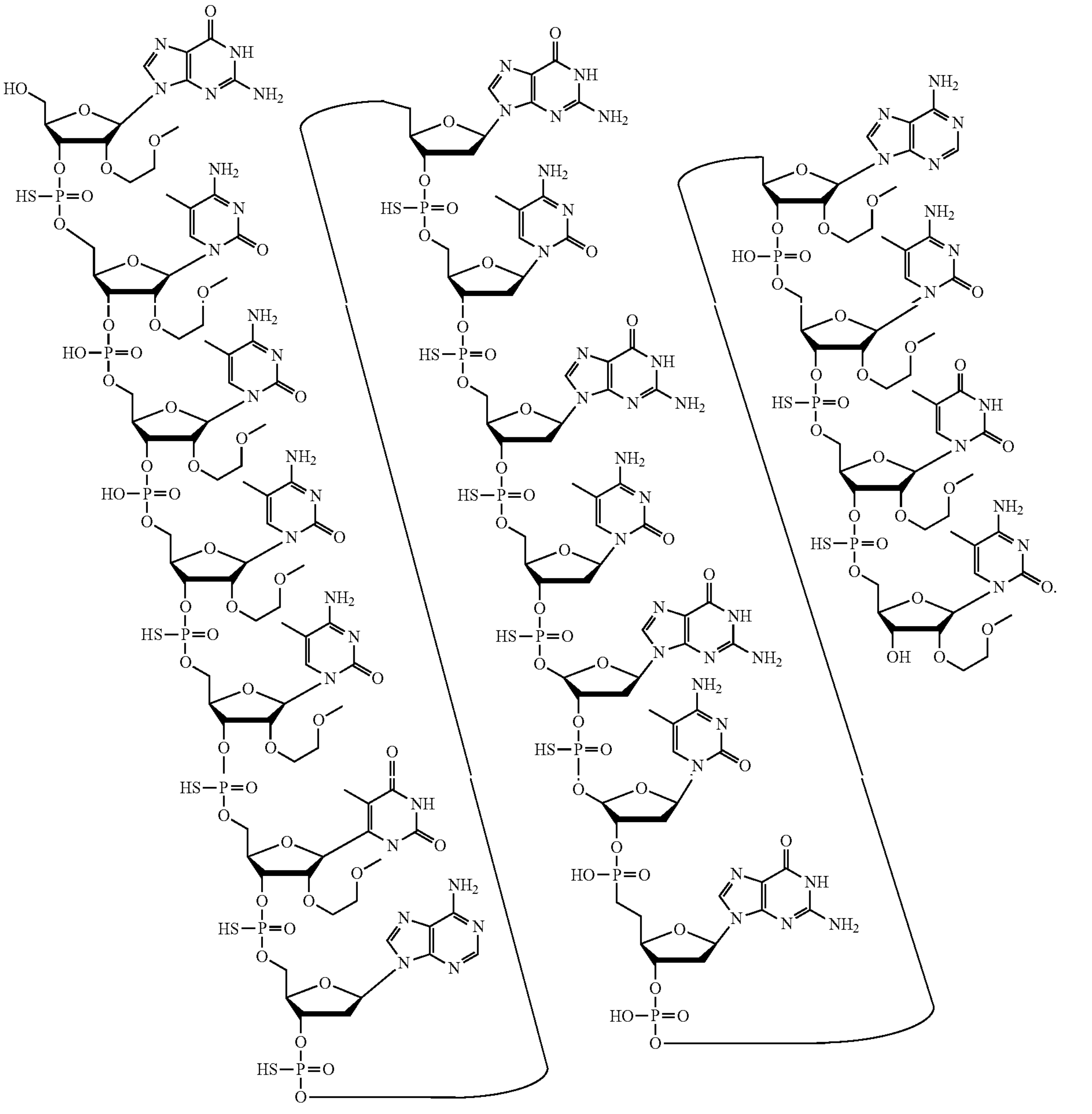

Embodiment 52. A method comprising administering to an animal the compound of 5 embodiment 51.

Embodiment 53. The method of embodiment 52, wherein the animal is a human.

Embodiment 54. The method of embodiment 53, wherein the administering inhibits C9ORF72.

Embodiment 55. The method of embodiment 53, wherein the administering prevents, treats, ameliorates, or slows progression of a C9ORF72 associated disease.

Embodiment 56. The method of embodiment 55, wherein the C9ORF72 associated disease is caused by a hexanucleotide repeat expansion.

Embodiment 57. The method of embodiment 55, wherein the C9ORF72 associated disease is any of amyotrophic lateral sclerosis (ALS), frontotemporal dementia (FTD), corticobasal degeneration syndrome (CBD), atypical Parkinsonian syndrome, or olivopontocerebellar degeneration (OPCD).

Embodiment 58. The method of embodiment 53, wherein the administering reduces nuclear foci.

Embodiment 59. The method of embodiment 53, wherein the administering reduces expression of C9ORF72 associated RAN translation products.

Embodiment 60. The method of embodiment 59, wherein the C9ORF72 associated RAN translation products are any of poly-(glycine-proline), poly-(glycine-alanine), and poly-(glycine-arginine).

Embodiment 61. A composition consisting of the sodium salt of a modified oligonucleotide according to the following formula:

(SEQ ID NO: 33)

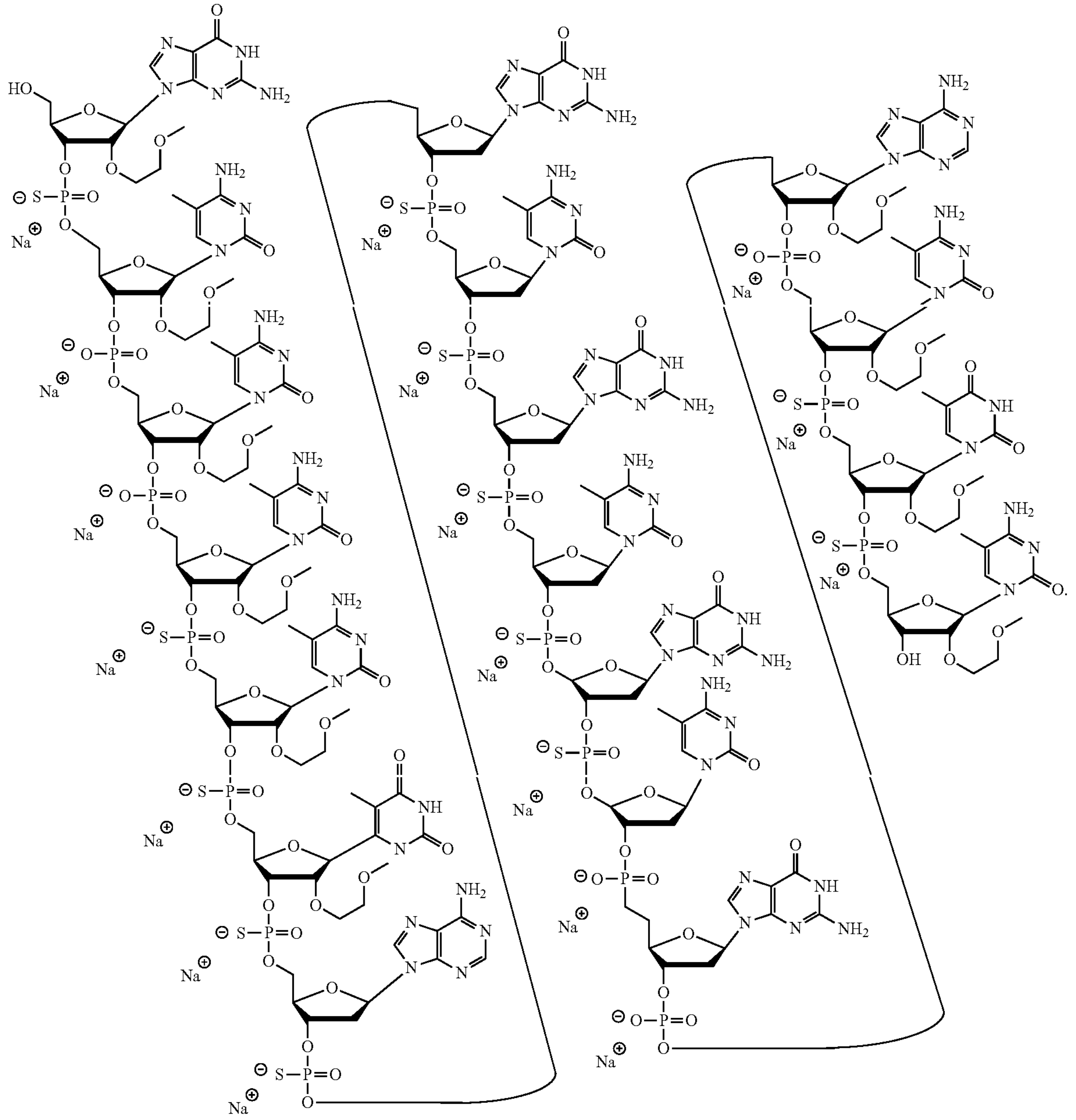

Embodiment 62. A method comprising administering to an animal the composition of embodiment 60.

Embodiment 63. The method of embodiment 62, wherein the animal is a human.

Embodiment 64. The method of embodiment 63, wherein the administering inhibits C9ORF72.

Embodiment 65. The method of embodiment 62, wherein the administering prevents, treats, ameliorates, or slows progression of a C9ORF72 associated disease.

Embodiment 66. The method of embodiment 65, wherein the C9ORF72 associated disease is caused by a hexanucleotide repeat expansion.

Embodiment 67. The method of embodiment 65, wherein the C9ORF72 associated disease is any of amyotrophic lateral sclerosis (ALS), frontotemporal dementia (FTD), corticobasal degeneration syndrome (CBD), atypical Parkinsonian syndrome, or olivopontocerebellar degeneration (OPCD).

Embodiment 68. The method of embodiment 63, wherein the administering reduces nuclear foci.

Embodiment 69. The method of embodiment 63, wherein the administering reduces expression of C9ORF72 associated RAN translation products.

Embodiment 70. The method of embodiment 69, wherein the C9ORF72 associated RAN translation products are any of poly-(glycine-proline), poly-(glycine-alanine), and poly-(glycine-arginine).

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound.

Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA: DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'—O—$CH_3$, among others), and bicyclic sugar modified nucleosides (such bicyclic sugar modified nucleosides may include those having a 4'—$(CH_2)_n$—O—2' bridge, where n=1 or n=2 and 4'—$CH_2$—O—$CH_2$-2'). Preferably, each distinct region comprises uniform sugar moieties. The wing-gap-wing motif is frequently described as "X—Y-Z", where "X" represents the length of the 5' wing region, "Y" represents the length of the gap region, and "Z" represents the length of the 3' wing region. As used herein, a gapmer described as "X—Y-Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X-Y or Y-Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a C9ORF72 nucleic acid possess a 5-10-5 gapmer motif.

In certain embodiments, antisense compounds targeted to a C9ORF72 nucleic acid possess a 5-8-5 gapmer motif.

In certain embodiments, antisense compounds targeted to a C9ORF72 nucleic acid possess sugar modifications in any of the following patterns: eeekkddddddddkkeee, eekkddddddddkkeee, ekddddddddekekeee, kekeddddddddde-keke, and ekekddddddddkekee; wherein, e=a 2'—O—methoxyethyl modified nucleoside d=a 2'-deoxynucleoside, and k=a cEt nucleoside.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'—$(CH_2)_n$—O—2' bridge, wherein n is 1 or 2; and 4'—$CH_2$—O—$CH_2$-2'. In certain embodiments, the bicyclic sugar is comprises a 4'—CH($CH_3$)—O—2' bridge. In certain embodiments, the chemical modification comprises a non-bicyclic 2'-modified sugar moiety. In certain embodiments, the non-bicyclic 2'-modified sugar moiety comprises a 2'—O—methylethyl group or a 2'—O—methyl group.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), the complement of GENBANK Accession No. NT_008413.18 truncated from nucleobase 27535000 to U.S. Pat. No. 27,565,000 (incorporated herein as SEQ ID NO: 2), GENBANK Accession No. BQ068108.1 (incorporated herein as SEQ ID NO: 3), GENBANK Accession No. NM 018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73 A (incorporated herein as SEQ ID NO: 10), and GENBANK Accession No. NW_001101662.1 truncated from nucleosides 8522000 to U.S. Pat. No. 8,552,000 (incorporated herein as SEQ ID NO: 11).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifcally exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) „oncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked)„ucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occuring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage. In certain embodiments, the antisense compounds targeted to a C9ORF72 nucleic acid comprise at least one phosphodiester linkage and at least one phosphorothioate linkage. In certain embodiments, antisense compounds targeted to a C9ORF72 nucleic acid possess internucleoside linkages in any of the following patterns: soooossssssssssooss, sooosssssssssooss, soosssssssssooss, and sosssssssssoooss; wherein, s=a phosphorothioate linkage, and o=a phosphodiester linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$(R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-

0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'—$OCH_3$, 2'—$OCH_2CH_3$, 2'—$OCH_2CH_2F$ and 2'—$O(CH_2)_2OCH_3$ substituent groups. The substituent at the 2' position can also be selected from allyl, amino, azido, thio, O-allyl, O-$C_1$-$C_{10}$ alkyl, $OCF_3$, $OCH_2F$, $O(CH_2)_2SCH_3$, $O(CH_2)_2$—O—N($R_m$)($R_n$), O—$CH_2$—C(═O)—N($R_m$)($R_n$), and O—$CH_2$—C(-O)—N($R_1$)—$(CH_2)_2$—N($R_m$)($R_n$), where each $R_1$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'—$(CH_2)$—O—2' (LNA); 4'—$(CH_2)$—S—2'; 4'—$(CH_2)_2$—O—2' (ENA); 4'—CH($CH_3$)—O—2' and 4'—CH($CH_2OCH_3$)—O—2' (and analogs thereof see U.S. Pat. No. 7,399,845, issued on Jul. 15, 2008); 4'—C($CH_3$)($CH_3$)—O—2' (and analogs thereof see PCT/US2008/068922 published as WO/2009/006478, published Jan. 8, 2009); 4'—$CH_2$—N($OCH_3$)-2' (and analogs thereof see PCT/US2008/064591 published as WO/2008/150729, published Dec. 11, 2008); 4'—$CH_2$—O—N($CH_3$)-2' (see published U.S. Patent Application US2004-0171570, published Sep. 2, 2004); 4'—$CH_2$—N(R)—O—2', wherein R is H, $C_1$-$C_{12}$ alkyl, or a protecting group (see U.S. Patent 7,427,672, issued on Sep. 23, 2008); 4'—$CH_2$—C(H) ($CH_3$)-2' (see Chattopadhyaya et al., J. Org. Chem., 2009, 74, 118-134); and 4'—$CH_2$—C(—$CH_2$)-2' (and analogs thereof see PCT/US2008/066154 published as WO 2008/154401, published on Dec. 8, 2008).

Further bicyclic nucleosides have been reported in published literature (see for example: Srivastava et al., J. Am. Chem. Soc., 2007, 129 (26) 8362-8379; Frieden et al., *Nucleic Acids Research,* 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A, 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,399,845; 7,053,207; 7,034,133; 6,794,499; 6,770,748; 6,670,461; 6,525,191; 6,268,490; U.S. Patent Publication Nos.: US2008-0039618; US2007-0287831; US2004-0171570; U.S. Patent Applications, Serial Nos.: 12/129,154; 61/099,844; 61/097,787; 61/086,231; 61/056,564; 61/026,998; 61/026,995; 60/989,574; International applications WO 2007/134181; WO 2005/021570; WO 2004/106356; and PCT International Applications Nos.: PCT/US2008/068922; PCT/US2008/066154; and PCT/US2008/064591). Each of the foregoing bicyclic nucleosides can be prepared having one or more stereochemical sugar configurations including for example a-L-ribofuranose and β-D-ribofuranose (see PCT international application PCT/DK98/00393, published on Mar. 25, 1999 as WO 99/14226).

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

In certain embodiments, bicyclic sugar moieties of BNA nucleosides include, but are not limited to, compounds having at least one bridge between the 4' and the 2' carbon atoms of the pentofuranosyl sugar moiety including without limitation, bridges comprising 1 or from 1 to 4 linked groups independently selected from —$[C(R_a)(R_b)]_n$—, —C($R_a$)═C($R_b$)—, —C($R_a$)═N—, —C(═$NR_a$)—, —C(═O)—, —C(═S)—, —O—, —Si$(R_a)_2$—, —S(═O)$_x$—, and —N($R_a$)—; wherein: x is 0, 1, or 2; n is 1, 2, 3, or 4; each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl (S(═O)$_2$-$J_1$), or sulfoxyl (S(═O)—$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C (-O)-H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is, —$[C(R_a)(R_b)]_n$-, —$[C(R_a)(R_b)]_n$—O—, —C($R_aR_b$)—N($R_1$)—O—or —C($R_aR_b$)—O—N(R)-. In certain embodiments, the bridge is 4'—$CH_2$-2', 4'—$(CH_2)_2$-2', 4'—$(CH_2)$ 3-2', 4'—$CH_2$—O—2', 4'—$(CH_2)_2$—O—2', 4'—$CH_2$—O—N(R)-2' and 4'—$CH_2$—N(R)—O—2'- wherein each Ris, independently, H, a protecting group or $C_1$-$C_{12}$ alkyl.

In certain embodiments, bicyclic nucleosides are further defined by isomeric configuration. For example, a nucleoside comprising a 4'—$(CH_2)$—O—2' bridge, may be in the a-L configuration or in the B-D configuration. Previously, a-L-methyleneoxy (4'—$CH_2$—O—2') BNA's have been incorporated into antisense oligonucleotides that showed antisense activity (Frieden et al., *Nucleic Acids Research,* 2003, 21, 6365-6372).

In certain embodiments, bicyclic nucleosides include those having a 4' to 2' bridge wherein such bridges include without limitation, a-L-4'—$(CH_2)$—O—2', β-D-4'—$CH_2$—O—2', 4'—$(CH_2)_2$—O—2', 4'—$CH_2$—O—N(R)-2', 4'—$CH_2$—N(R)—O—2', 4'—CH($CH_3$)—O—2', 4'—$CH_2$-S-2', 4'—$CH_2$—N(R)-2', 4'—$CH_2$—CH($CH_3$)-2', and 4'—$(CH_2)$ 3-2', wherein R is H, a protecting group or $C_1$-$C_{12}$ alkyl.

In certain embodiment, bicyclic nucleosides have the formula:

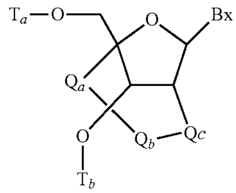

wherein:

Bx is a heterocyclic base moiety; $-Q_a-Q_b-Q_c-$ is $-CH_2-N(R_c)-CH_2-$, $-C(=O)-N(R_c)-CH_2-$, $-CH_2-O-N(R_c)-$, $-CH_2-N(R_c)-O-$ or $-N(R_c)-O-CH_2$;

$R_c$ is $C_1$-$C_{12}$ alkyl or an amino protecting group; and $T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides have the formula:

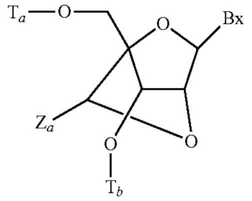

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thiol.

In one embodiment, each of the substituted groups, is, independently, mono or poly substituted with substituent groups independently selected from halogen, oxo, hydroxyl, $OJ_c$, $NJ_cJ_a$, $SJ_c$, $N_3$, $OC(=X)J_c$, and $NJ_cC(=X)NJ$-$J_a$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides have the formula:

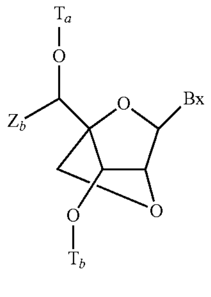

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl $(C(=O)-)$.

In certain embodiments, bicyclic nucleosides have the formula:

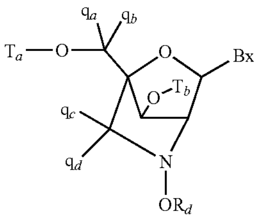

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides have the formula:

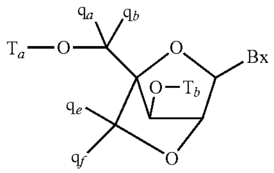

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O-C(=O)NJ_jJ_k$, $N(H)C(=NH)NJ_jJ_k$, $N(H)C(=O)NJ_jJk$ or $N(H)C(=S)NJ_jJk$;

or $q_e$ and $q_f$ together are $=C(q_g)(q_h)$;

$q_g$ and $q_h$ are each, independently, H, halogen, $C_1$-$C_{12}$ alkyl or substituted $C_1$-$C_{12}$ alkyl.

The synthesis and preparation of adenine, cytosine, guanine, 5-methyl-cytosine, thymine and uracil bicyclic nucleosides having a 4'—$CH_2$—O—2' bridge, along with their oligomerization, and nucleic acid recognition properties have been described (Koshkin et al., *Tetrahedron,* 1998, 54, 3607-3630). The synthesis of bicyclic nucleosides has also been described in WO 98/39352 and WO 99/14226.

Analogs of various bicyclic nucleosides that have 4' to 2' bridging groups such as 4'—$CH_2$—O—2' and 4'—$CH_2$-S-2', have also been prepared (Kumar et al., *Bioorg. Med. Chem. Lett.,* 1998, 8, 2219-2222). Preparation of oligodeoxyribonucleotide duplexes comprising bicyclic nucleosides for use as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.,* 1998, 63, 10035-10039). In addition, 2'-amino- and 2'-methylamino-BNA's have been prepared and the thermal stability of their duplexes with complementary RNA and DNA strands has been previously reported. In certain embodiments, bicyclic nucleosides have the formula:

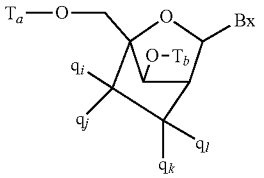

wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_i$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(═O)$OJ_j$, C(═O)$NJ_jJ_k$, C(═O)$J_j$, O-C(═O)$NJ_jJ_k$, N(H)C(═NH)$NJ_jJ_k$, N(H)C(═O)$NJ_j$Jk or N(H)C(═S)$NJ_j$Jk; and $q_i$ and $q_j$ or $q_l$ and $q_k$ together are=C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'—($CH_2$) 3-2' bridge and the alkenyl analog bridge 4'—CH═CH—$CH_2$-2' have been described (Frier et al., *Nucleic Acids Research,* 1997, 25 (22), 4429-4443 and Albaek et al., *J. Org. Chem.,* 2006, 71, 7731-7740). The synthesis and preparation of carbocyclic bicyclic nucleosides along with their oligomerization and biochemical studies have also been described (Srivastava et al., *J. Am. Chem. Soc.* 2007, 129 (26), 8362-8379).

In certain embodiments, bicyclic nucleosides include, but are not limited to, (A) a-L-methyleneoxy (4'—$CH_2$—O—2') BNA, (B) β-D-methyleneoxy (4'—$CH_2$—O—2') BNA, (C) ethyleneoxy (4'—$(CH_2)_2$—O—2') BNA, (D) aminooxy (4'—$CH_2$—O—N(R)-2') BNA, (E) oxyamino (4'—$CH_2$—N(R)—O—2') BNA, (F) methyl(methyleneoxy) (4'—CH($CH_3$)—O—2') BNA (also referred to as constrained ethyl or cEt), (G) methylene-thio (4'—$CH_2$-S-2') BNA, (H) methylene-amino (4'—$CH_2$—N(R)-2') BNA, (I) methyl carbocyclic (4'—$CH_2$—CH($CH_3$)-2') BNA, (J) propylene carbocyclic (4'—($CH_2$) 3-2') BNA, and (K) vinyl BNA as depicted below.

(A)

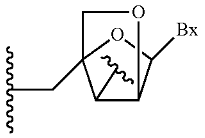

(B)

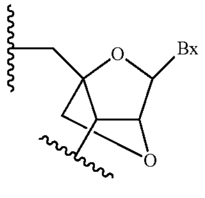

(C)

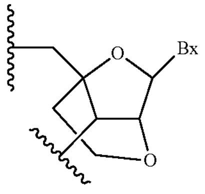

(D)

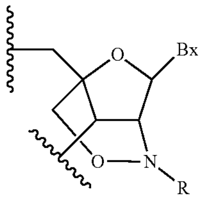

(E)

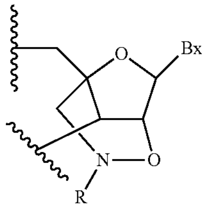

(F)

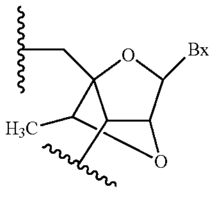

(G)

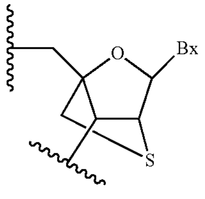

-continued (H)

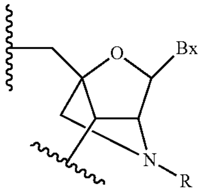

(I)

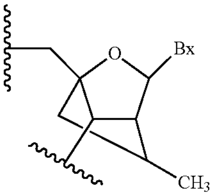

(J)

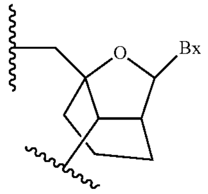

(K)

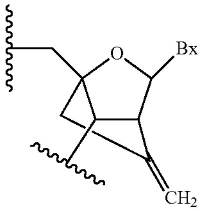

wherein Bx is the base moiety and R is, independently, H, a protecting group, $C_1$-$C_6$ alkyl or $C_1$-$C_6$ alkoxy.

As used herein, the term "modified tetrahydropyran nucleoside" or "modified THP nucleoside" means a nucleoside having a six-membered tetrahydropyran "sugar" substituted for the pentofuranosyl residue in normal nucleosides and can be referred to as a sugar surrogate. Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854) or fluoro HNA (F-HNA) having a tetrahydropyranyl ring system as illustrated below.

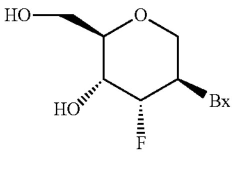

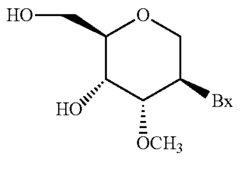

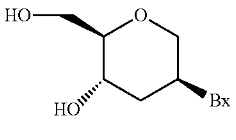

In certain embodiment, sugar surrogates are selected having the formula:

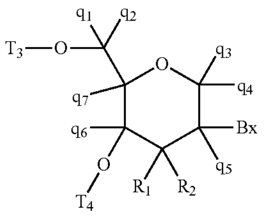

wherein:

Bx is a heterocyclic base moiety;

$T_3$ and $T_4$ are each, independently, an internucleoside linking group linking the tetrahydropyran nucleoside analog to the oligomeric compound or one of $T_3$ and $T_4$ is an internucleoside linking group linking the tetrahydropyran nucleoside analog to an oligomeric compound or oligonucleotide and the other of $T_3$ and $T_4$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides are provided wherein one of $R_1$ and $R_2$ is F. In certain embodiments, $R_1$ is fluoro and $R_2$ is H; $R_1$ is methoxy and $R_2$ is H, and $R_1$ is methoxyethoxy and $R_2$ is H.

In certain embodiments, sugar surrogates comprise rings having more than 5 atoms and more than one heteroatom. For example nucleosides comprising morpholino sugar moieties and their use in oligomeric compounds has been reported (see for example: Braasch et al., Biochemistry, 2002, 41, 4503-4510; and U.S. Pat. Nos. 5,698,685; 5,166,315; 5,185,444; and 5,034,506). As used here, the term "morpholino" means a sugar surrogate having the following formula:

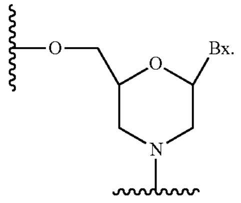

In certain embodiments, morpholinos may be modified, for example by adding or altering various substituent groups from the above morpholino structure. Such sugar surrogates are referred to herein as "modified morpholinos."

Combinations of modifications are also provided without limitation, such as 2'-F-5'-methyl substituted nucleosides (see PCT International Application WO 2008/101157 published on Aug. 21, 2008 for other disclosed 5', 2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'—$CH_2$—O—2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129 (26), 8362-8379).

In certain embodiments, antisense compounds comprise one or more modified cyclohexenyl nucleosides, which is a nucleoside having a six-membered cyclohexenyl in place of the pentofuranosyl residue in naturally occurring nucleosides. Modified cyclohexenyl nucleosides include, but are not limited to those described in the art (see for example commonly owned, published PCT Application WO 2010/036696, published on Apr. 10, 2010, Robeyns et al., *J. Am. Chem. Soc.,* 2008, 130 (6), 1979-1984; Horváth et al., *Tetrahedron Letters,* 2007, 48, 3621-3623; Nauwelaerts et al., *J. Am. Chem. Soc.,* 2007, 129 (30), 9340-9348; Gu et al.,, *Nucleosides, Nucleotides & Nucleic Acids,* 2005, 24 (5-7), 993-998; Nauwelaerts et al., *Nucleic Acids Research,* 2005, 33 (8), 2452-2463; Robeyns et al., *Acta Crystallographica, Section F: Structural Biology and Crystallization Communications,* 2005, F61 (6), 585-586; Gu et al., *Tetrahedron,* 2004, 60 (9), 2111-2123; Gu et al., *Oligonucleotides,* 2003, 13 (6), 479-489; Wang et al., *J. Org. Chem.,* 2003, 68, 4499-4505; Verbeure et al., *Nucleic Acids Research,* 2001, 29 (24), 4941-4947; Wang et al., *J. Org. Chem.,* 2001, 66, 8478-82; Wang et al., *Nucleosides, Nucleotides & Nucleic Acids,* 2001, 20 (4-7), 785-788; Wang et al., *J. Am. Chem.,* 2000, 122, 8595-8602; Published PCT application, WO 06/047842; and Published PCT Application WO 01/049687; the text of each is incorporated by reference herein, in their entirety). Certain modified cyclohexenyl nucleosides have Formula X.

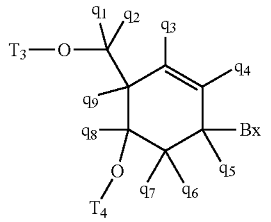

X wherein independently for each of said at least one cyclohexenyl nucleoside analog of Formula X:

Bx is a heterocyclic base moiety;

$T_3$ and $T_4$ are each, independently, an internucleoside linking group linking the cyclohexenyl nucleoside analog to an antisense compound or one of $T_3$ and $T_4$ is an internucleoside linking group linking the tetrahydropyran nucleoside analog to an antisense compound and the other of $T_3$ and $T_4$ is H, a hydroxyl protecting group, a linked conjugate group, or a 5'- or 3'-terminal group; and $q_1$, $q_2$, $q_3$, $q_4$, $q_5$, $q_6$, $q_7$, $q_8$ and $q_9$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or other sugar substituent group.

Many other monocyclic, bicyclic and tricyclic ring systems are known in the art and are suitable as sugar surrogates that can be used to modify nucleosides for incorporation into oligomeric compounds as provided herein (see for example review article: Leumann, Christian *J. Bioorg. & Med. Chem.,* 2002, 10, 841-854). Such ring systems can undergo various additional substitutions to further enhance their activity.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O $[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)$ N(H) $CH_3$, and $O(CH_2)_nON[(CH_2)_nCH_3]_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'—O—methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., Chimia, 1996, 50, 168-176; Altmann et al., *Biochem. Soc. Trans.,* 1996, 24, 630-637; and Altmann et al., *Nucleosides Nucleotides,* 1997, 16, 917-926).

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, O-allyl, O-$C_1$-$C_{10}$ alkyl, —$OCF_3$, O—$(CH_2)_2$—O—$CH_3$, 2'—$O(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl, 2'-modified nucleosides may further comprise other modifications, for example at other positions of the sugar and/or at the nucleobase.

As used herein, "2'-F" refers to a nucleoside comprising a sugar comprising a fluoro group at the 2' position of the sugar ring.

As used herein, "2'—OMe" or "2'—$OCH_3$", "2'—O—methyl" or "2'-methoxy" each refers to a nucleoside comprising a sugar comprising an —$OCH_3$ group at the 2' position of the sugar ring.

As used herein, "MOE" or "2'-MOE" or "2'—$OCH_2CH_2OCH_3$" or "2'—O—methoxyethyl" each refers to a nucleoside comprising a sugar comprising a—$OCH_2CH_2OCH_3$ group at the 2' position of the sugar ring.

Methods for the preparations of modified sugars are well known to those skilled in the art. Some representative U.S. patents that teach the preparation of such modified sugars include without limitation, U.S.: 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

In nucleotides having modified sugar moieties, the nucleobase moieties (natural, modified or a combination thereof) are maintained for hybridization with an appropriate nucleic acid target. In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'—$CH(CH_3)$—O—2') bridging group. In certain embodiments, the (4'—$CH(CH_3)$—O—2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commercial vendors (e.g. American Type Culture Collection, Manassas, VA; Zen-Bio, Inc., Research Triangle Park, NC; Clonetics Corporation, Walkersville, MD) and are cultured according to the vendor's instructions using commercially available reagents (e.g. Invitrogen Life Technologies, Carlsbad, CA). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN(Invitrogen, Carlsbad, CA). Antisense oligonucleotides are mixed with LIPOFECTIN in OPTI-MEM 1 (Invitrogen, Carlsbad, CA) to achieve the desired final concentration of antisense oligonucleotide and a LIPOFECTIN concentration that typically ranges 2 to 12 μg/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPO- FECTAMINE concentration that typically ranges 2 to 12 μg/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, CA) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, CA). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN(Invitrogen, Inc. Carlsbad, CA). Cyclophilin A expression is quantified by real time PCR, by being run simultaneously with the target, multiplexing, or separately. Total RNA is quantified using RIBOGREEN RNA quantification reagent (Invetrogen, Inc. Eugene, OR). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, CA).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline (PBS) or artificial cerebrospinal fluid (aCSF). Administration includes parenteral routes of administration, such as intraperitoneal, intravenous, and subcutaneous, as well as central routes of administration such as intracerebroventricular or intrathecal. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid in any stage of RNA processing. For example, described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1*a*, exon 1b, exon 1c, exon 1d, exon 1e, exon 2, exon 3, exon 4, exon 5, exon 6, exon 7, exon 8, exon 9, exon 10, exon11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72. In certain embodiments, the antisense oligonucleotides described herein selectively hybridize to certain variants of C9ORF72. In certain embodiments, the antisense oligonucleotides described herein selectively hybridize to variants of C9ORF72 containing a hexanucleotide repeat expansion. In certain embodiments, the antisense oligonucleotides described herein selectively hybridize to pre-mRNA variants containing the hexanucleotide repeat. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG.

In certain embodiments, the antisense oligonucleotides described herein inhibit expression of all variants of C9ORF72. In certain embodiments, the antisense oligonucleotides described herein inhibit expression of all variants of C9ORF72 equally. In certain embodiments, the antisense oligonucleotides described herein preferentially inhibit expression of one or more variants of C9ORF72. In certain embodiments, the antisense oligonucleotides described herein preferentially inhibit expression of variants of C9ORF72 containing a hexanucleotide repeat expansion. In certain embodiments, the antisense oligonucleotides described herein selectively inhibit expression of pre-mRNA variants containing the hexanucleotide repeat. In certain embodiments, the antisense oligonucleotides described herein selectively inhibit expression of C9ORF72 pathogenic associated mRNA variants. In certain embodiments, pre-mRNA variants of C9ORF72 containing a hexanucleotide repeat expansion include SEQ ID NO: 1-3 and 6-10. In certain embodiments, such hexanucleotide repeat expansion comprises at least 24 repeats of any of GGGGCC, GGGGGG, GGGGGC, or GGGGCG. In certain embodiments, the hexanucleotide repeat expansion forms nuclear foci. In certain embodiments, antisense oligonucleotides described herein are useful for reducing nuclear foci. Nuclear foci may be reduced in terms of percent of cells with foci as well as number of foci per cell.

Selective Inhibition of Certain Pathogenic Associated Variants

In certain examples herein, primer probe set RTS3905 detects an mRNA variant (e.g. NM_001256054.1) processed from a pre-mRNA variant containing the hexanucleotide repeat. The mRNA variant processed from a pre-mRNA variant containing the hexanucleotide repeat (i.e., the "C9ORF72 pathogenic associated mRNA variant"). A pre-mRNA contains the hexanucleotide repeat when transcription of the pre-mRNA begins in the region from the start site of exon 1A to the start site of exon 1B, e.g., nucleotides 1107 to 1520 of the genomic sequence (SEQ ID NO: 2, the complement of GENBANK Accession No. NT_008413.18 truncated from nucleosides 27535000 to 27565000). Oligonucleotides were designed in this region to selectively target the pre-mRNA variant containing the hexanucleotide repeat. RTS3905 measures an mRNA product (i.e. the C9ORF72 pathogenic associated mRNA variant) of the pre-mRNA variant containing the hexanucleotide repeat and, therefore, measures the reduction of the pre-mRNA variant containing the hexanucleotide repeat.

C9ORF72 Features

Antisense oligonucleotides described herein may hybridize to any C9ORF72 variant at any state of processing within any element of the C9ORF72 gene. For example, antisense oligonucleotides described herein may hybridize to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 for the various C9ORF72 variants described below. Antisense oligonucleotides described herein may also target variants not characterized below and such variants are characterized in GENBANK. Moreover, antisense oligonucleotides described herein may also target elements other than exons and such elements are characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
|---|---|---|---|---|
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
|---|---|---|---|---|
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
|---|---|---|---|---|
| exon 1A | 1 | 80 | 1137 | 1216 |
| exon 2 | 81 | 568 | 7839 | 8326 |
| exon 3 | 569 | 628 | 9413 | 9472 |

TABLE 3-continued

| Functional Segments for NM_145005.5 (SEQ ID NO: 6) | | | | |
|---|---|---|---|---|
| Exon Number | mRNA start site | mRNA stop site | Start site in reference to SEQ ID NO: 2 | Stop site in reference to SEQ ID NO: 2 |
| exon 4 | 629 | 724 | 12527 | 12622 |
| exon 5B (exon 5 into intron 5) | 725 | 1871 | 13354 | 14500 |

TABLE 4

| Functional Segments for DB079375.1 (SEQ ID NO: 7) | | | | |
|---|---|---|---|---|
| Exon Number | mRNA start site | mRNA stop site | Start site in reference to SEQ ID NO: 2 | Stop site in reference to SEQ ID NO: 2 |
| exon 1E | 1 | 35 | 1135 | 1169 |
| exon 2 | 36 | 524 | 7839 | 8326 |
| exon 3 (EST ends before end of full exon | 525 | 562 | 9413 | 9450 |

TABLE 5

| Functional Segments for BU194591.1 (SEQ ID NO: 8) | | | | |
|---|---|---|---|---|
| Exon Number | mRNA start site | mRNA stop site | Start site in reference to SEQ ID NO: 2 | Stop site in reference to SEQ ID NO: 2 |
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to C9ORF72 are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 specific inhibitor described herein include, but are not limited to, an additional C9ORF72 inhibitor.

In certain embodiments, pharmaceutical agents that may be co-administered with a C9ORF72 specific inhibitor described herein include, but are not limited to, a C9ORF72 antisense transcript specific inhibitor. In certain embodiments, the C9ORF72 antisense transcript specific inhibitor is an antisense compound. In certain embodiments, the antisense compound is a modified oligonucleotide. In certain embodiments, the modified oligonucleotide is single-stranded.

In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

Certain Comparator Compositions

In certain embodiments, compounds described herein are more tolerable than ISIS 576816, ISIS 576974, ISIS 577061, ISIS 577065, and/or ISIS 577083. ISIS 576816, ISIS 576974, ISIS 577061, ISIS 577065, and ISIS 577083 were selected as comparator compounds because they exhibited high levels of dose-dependent reduction of C9ORF72 mRNA in various studies described in WO2014/062691. Thus, ISIS 576816, ISIS 576974, ISIS 577061, ISIS 577065, and ISIS 577083 were deemed highly efficacious and potent compounds. Additionally, ISIS 577065, ISIS 577056, and ISIS 576816 described in WO2014/062691 are structurally similar as compounds described herein. For example, ISIS 577065 has a 16 nucleobase overlap with ISIS 801287; ISIS 577056 has a 16 nucleobase overlap with ISIS 806679; ISIS 576816 has an 18 nucleobase overlap with ISIS 802473 (18-mer); and ISIS 576816 has an 18 nucleobase overlap with ISIS 802459.

In certain embodiments, ISIS 576816, a 5-10-5 MOE gapmer, having a sequence of (from 5' to 3') GCCTTACTCTAGGACCAAGA (incorporated herein as SEQ ID NO: 21), wherein each internucleoside linkage is a phosphorothioate linkage, each cytosine is a 5-methylcytosine, and each of nucleosides 1-5 and 16-20 comprise a 2'—O—methoxyethyl group, which was previously described in WO2014/062691, incorporated herein by reference, is a comparator compound. ISIS 576816 achieved an average FOB score of 7.00 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 576816.

In certain embodiments, ISIS 576974, a 5-10-5 MOE gapmer, having a sequence of (from 5' to 3') GGGACACTACAAGGTAGTAT (incorporated herein as SEQ ID NO: 56), wherein each internucleoside linkage is a phosphorothioate linkage, each cytosine is a 5-methylcytosine, and each of nucleosides 1-5 and 16-20 comprise a 2'—O—methoxyethyl group, which was previously described in WO2014/062691, incorporated herein by reference, is a comparator compound. ISIS 576974 achieved an average FOB score of 5.67 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 576974.

In certain embodiments, ISIS 577061, a 5-10-5 MOE gapmer, having a sequence of (from 5' to 3') TACAGGCTGCGGTTGTTTCC (incorporated herein as SEQ ID NO: 57), wherein each internucleoside linkage is a phosphorothioate linkage, each cytosine is a 5-methylcytosine, and each of nucleosides 1-5 and 16-20 comprise a 2'—O—methoxyethyl group, which was previously described in WO2014/062691, incorporated herein by reference, is a comparator compound. ISIS 577061 achieved an average FOB score of 7.00 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 577061.

In certain embodiments, ISIS 577065, a 5-10-5 MOE gapmer, having a sequence of (from 5' to 3') CCCGGCCCCTAGCGCGCGAC (incorporated herein as SEQ ID NO: 58), wherein each internucleoside linkage is a phosphorothioate linkage, each cytosine is a 5-methylcytosine, and each of nucleosides 1-5 and 16-20 comprise a 2'—O—methoxyethyl group, which was previously described in WO2014/062691, incorporated herein by reference, is a comparator compound. ISIS 577065 achieved an average FOB score of 6.00 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 577065.

In certain embodiments, ISIS 577083, a 5-10-5 MOE gapmer, having a sequence of (from 5' to 3') GGTAACTTCAAACTCTTGGG (incorporated herein as SEQ ID NO: 59), wherein each internucleoside linkage is a phosphorothioate linkage, each cytosine is a 5-methylcytosine, and each of nucleosides 1-5 and 16-20 comprise a 2'—O—methoxyethyl group, which was previously described in WO2014/062691, incorporated herein by reference, is a comparator compound. ISIS 577083 achieved an average FOB score of 7.00 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 577083.

In certain embodiments, ISIS 577056, a 5-10-5 MOE gapmer, having a sequence of (from 5' to 3') AATCTTTATCAGGTCTTTTC (incorporated herein as SEQ ID NO:

60), wherein each internucleoside linkage is a phosphorothioate linkage, each cytosine is a 5-methylcytosine, and each of nucleosides 1-5 and 16-20 comprise a 2'—O—methoxyethyl group, which was previously described in WO2014/062691, incorporated herein by reference, is a comparator compound. ISIS 577056 achieved an average FOB score of 6.5 in a study of acute tolerability in mice (see Example 3 hereinbelow). Certain compounds described herein achieved a lower FOB score in a similar study of acute tolerability in mice (see Example 2 hereinbelow), including ISIS 801287, ISIS 806679, ISIS 802473, and ISIS 802459. Therefore, certain compounds described herein are more tolerable than comparator compound ISIS 577056.

Certain Human Therapeutics

The human C9ORF72 antisense oligonucleotides described herein are human therapeutics. Various parameters of potency, efficacy, and/or tolerability are being examined. Such parameters include in vitro inhibition of total C9ORF72 RNA expression, in vitro inhibition of C9ORF72 pathogenic associated RNA variant expression, in vitro dose response (IC50), in vivo inhibition of total or pathogenic RNA and/or protein in a transgenic animal containing a human C9ORF72 transgene in relevant tissues (e.g., brain and/or spinal cord), tolerability in mouse, tolerability in rat, and/or tolerability in a primate. Tolerability markers that may be measured include blood and serum chemistry parameters, CSF chemistry parameters, body and organ weights, general observations and/or behavioral tests, and/or biochemical markers such as GFAP and/or AIF1. Acute or long term tolerability may be measured.

Certain Compositions

1. ISIS 801287

In certain embodiments, ISIS 801287 is characterized as a 4-8-6 MOE gapmer, having a sequence of (from 5' to 3') GCCCCTAGCGCGCGACTC (incorporated herein as SEQ ID NO: 33), wherein each of nucleosides 1~4 and 13-18 are 2'—O—methoxyethylribose modified nucleosides, and each of nucleosides 5-12 are 2'-deoxynucleosides, wherein the internucleoside linkages between nucleosides 2 to 3, 3 to 4, 13 to 14, 14 to 15, and 15 to 16 are phosphodiester linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 16 to 17, and 17 to 18 are phosphorothioate linkages, and wherein each cytosine is a 5'-methylcytosine.

In certain embodiments, ISIS 801287 is described by the following chemical notation: Ges mCeo mCeo mCes mCds Tds Ads Gds mCds Gds mCds Gds mCeo Geo Aeo mCes Tes mCe; wherein, A=an adenine, mC=a 5'-methylcytosine G=a guanine, T=a thymine, e=a 2'—O—methoxyethylribose modified sugar d=a 2'-deoxyribose sugar, s=a phosphorothioate internucleoside linkage, and o=a phosphodiester internucleoside linkage.

In certain embodiments, ISIS 801287 is described by the following chemical structure, or a salt thereof:

(SEQ ID NO: 33)

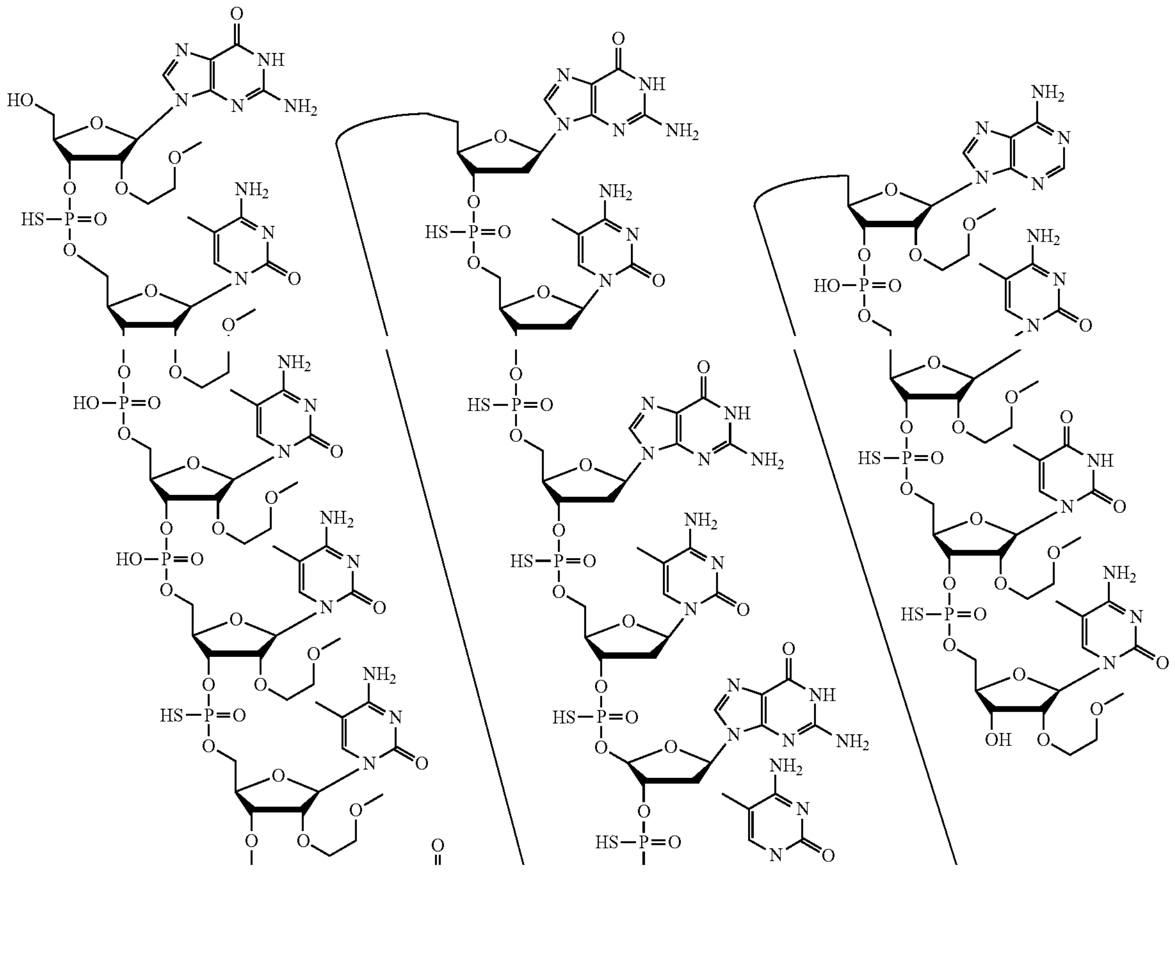

-continued
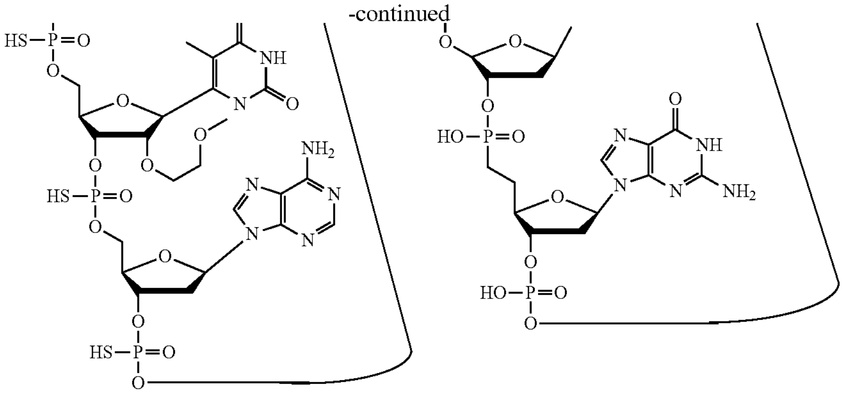
Structure 1. ISIS 801287
In certain embodiments, the sodium salt of ISIS 801287 is described by the following chemical structure:
(SEQ ID NO: 33)
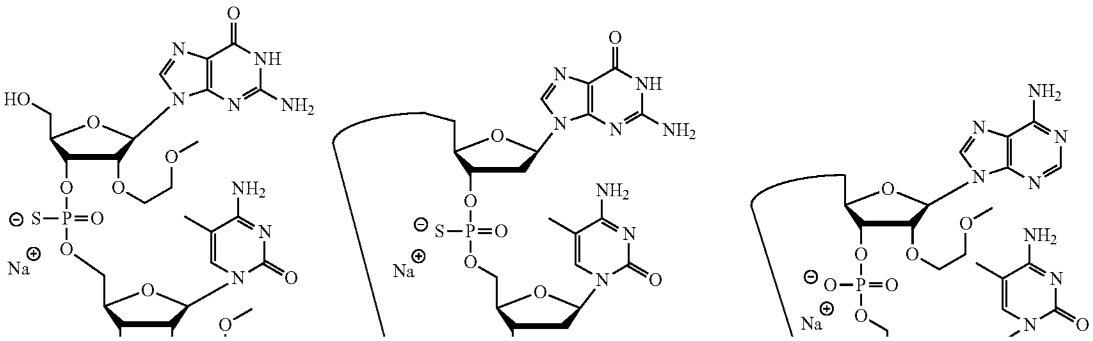
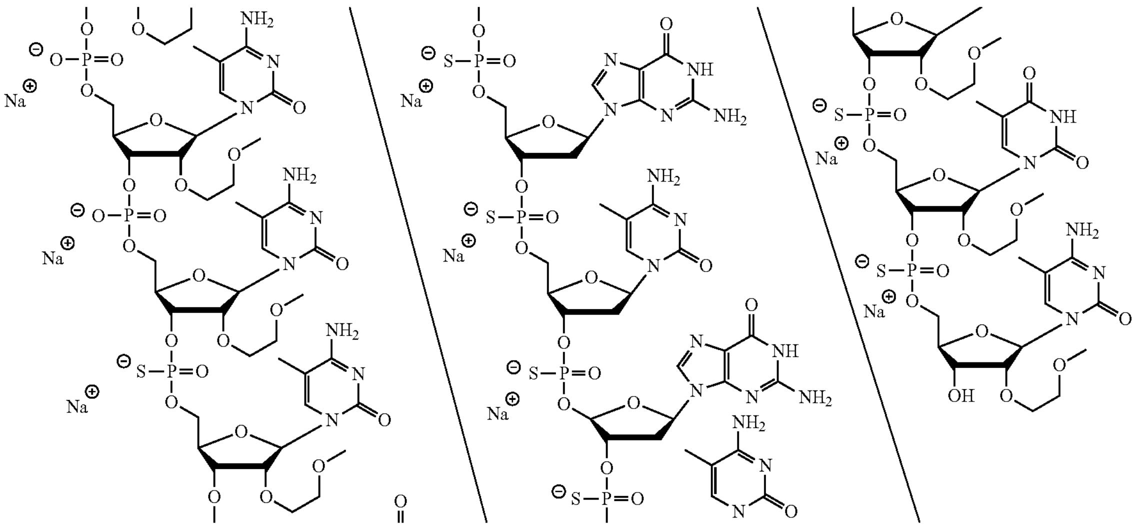

-continued

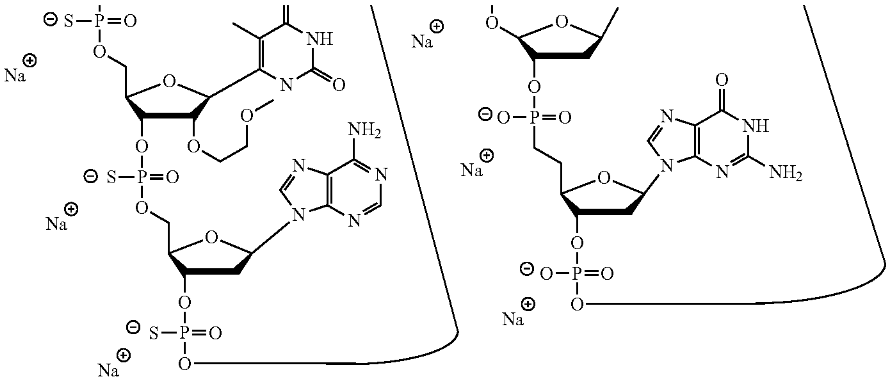

Structure 2. The sodium salt of ISIS 801287

2. ISIS 806679

In certain embodiments, ISIS 806679 is characterized as a 6-10-4 MOE gapmer, having a sequence of (from 5' to 3') GGTTAATCTTTATCAGGTCT (incorporated herein as SEQ ID NO: 49), wherein each of nucleosides 1-6 and 17-20 are 2'—O—methoxyethylribose modified nucleosides, and each of nucleosides 7-16 are 2'-deoxynucleosides, wherein the internucleoside linkages between nucleosides 2 to 3, 3 to 4, 4 to 5, 5 to 6, 6 to 7, and 17 to 18 are phosphodiester linkages and the internucleoside linkages between nucleosides 1 to 2, 7 to 8, 8 to 9, 9 to 10, 10 to 11, 11 to 12, 12 to 13, 13 to 14, 14 to 15, 15 to 16, 16 to 17, 18 to 19, and 19 to 20 are phosphorothioate linkages, and wherein each cytosine is a 5'-methylcytosine.

In certain embodiments, ISIS 806679 is described by the following chemical notation: Ges Geo Teo Teo Aeo Aeo Tds mCds Tds Tds Tds Ads Tds mCds Ads Gds Geo Tes mCes Te; wherein, A=an adenine, mC=a 5'-methylcytosine G=a guanine, T=a thymine, e=a 2'—O—methoxyethylribose modified sugar d=a 2'-deoxyribose sugar, s=a phosphorothioate internucleoside linkage, and o=a phosphodiester internucleoside linkage.

In certain embodiments, ISIS 806679 is described by the following chemical structure, or a salt thereof:

(SEQ ID NO: 49)

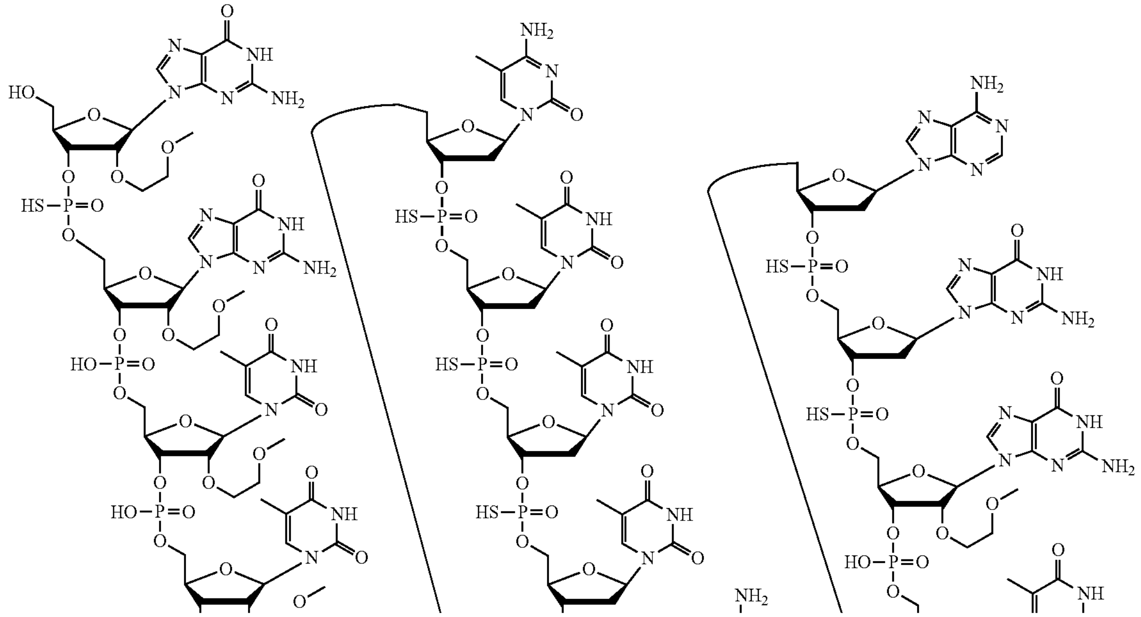

-continued
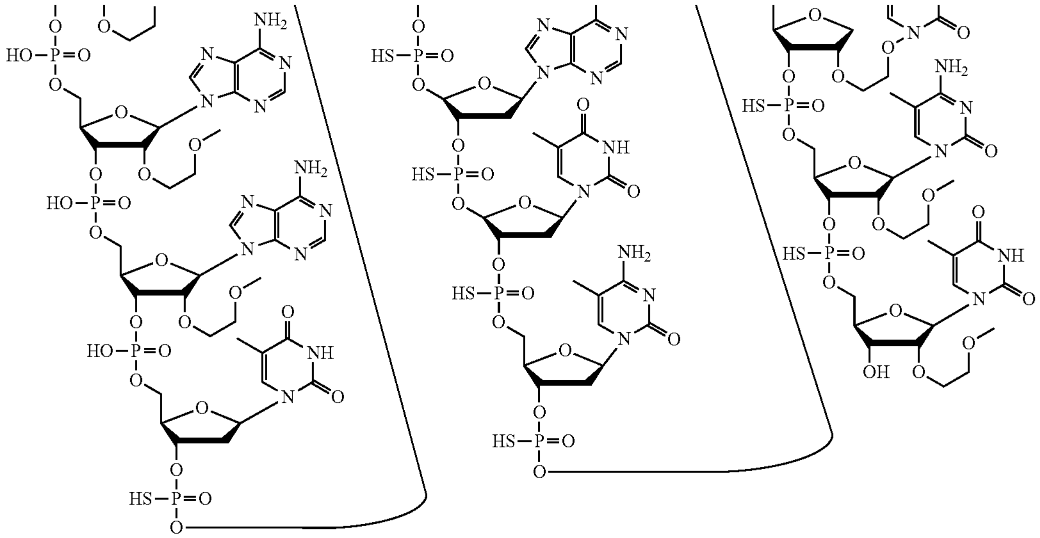
Structure 3. ISIS 806679
In certain embodiments, the sodium salt of ISIS 806679 is described by the following chemical structure:
(SEQ ID NO: 49)
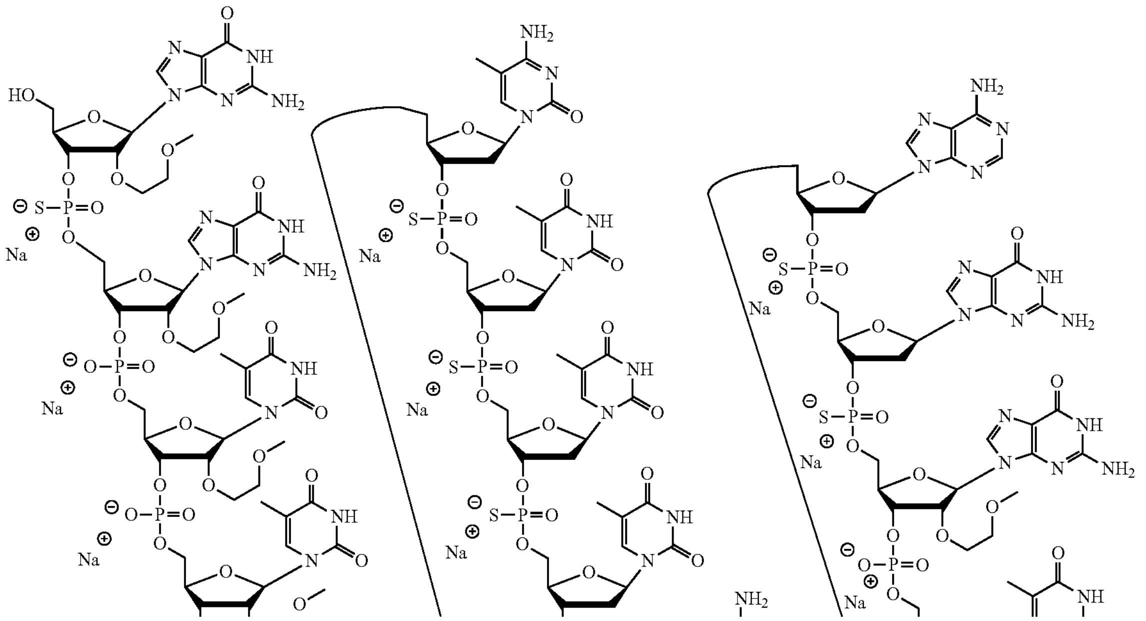

-continued

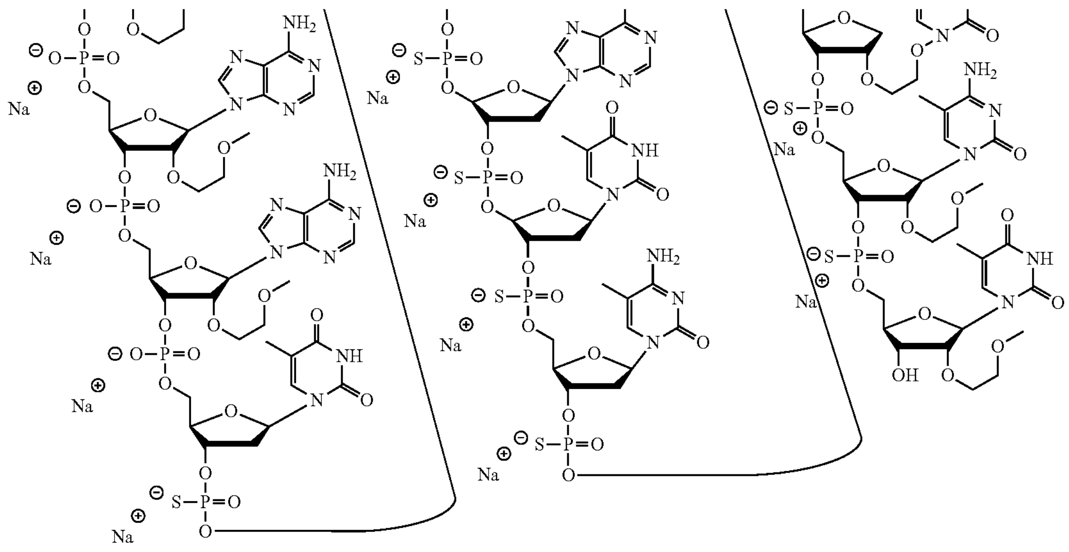

Structure 4. The sodium salt of ISIS 806679

3. ISIS 802473

In certain embodiments, ISIS 802473 is characterized as a 4-8-6 MOE gapmer, having a sequence of (from 5' to 3') GCCTTACTCTAGGACCAA (incorporated herein as SEQ ID NO: 47), wherein each of nucleosides 1~4 and 13-18 are 2'—O—methoxyethylribose modified nucleosides, and each of nucleosides 5-12 are 2'-deoxynucleosides, wherein the internucleoside linkages between nucleosides 2 to 3, 3 to 4, 13 to 14, 14 to 15, and 15 to 16 are phosphodiester linkages and the internucleoside linkages between nucleosides are 1 to 2, 4 to 5, 5 to 6, 6 to 7, 7 to 8, 8 to 9, 9 to 10, 10 to 11, 11 to 12, 12 to 13, 16 to 17, and 17 to 18 are phosphorothioate linkages, and wherein each cytosine is a 5'-methylcytosine.

In certain embodiments, ISIS 802473 is described by the following chemical notation: Ges mCeo mCeo Tes Tds Ads mCds Tds mCds Tds Ads Gds Geo Aeo mCeo mCes Aes Ae; wherein, A=an adenine, mC=a 5'-methylcytosine G=a guanine, T=a thymine, e=a 2'—O—methoxyethylribose modified sugar d=a 2'-deoxyribose sugar, s=a phosphorothioate internucleoside linkage, and o=a phosphodiester internucleoside linkage.

In certain embodiments, ISIS 802473 is described by the following chemical structure, or a salt thereof:

(SEQ ID NO: 47)

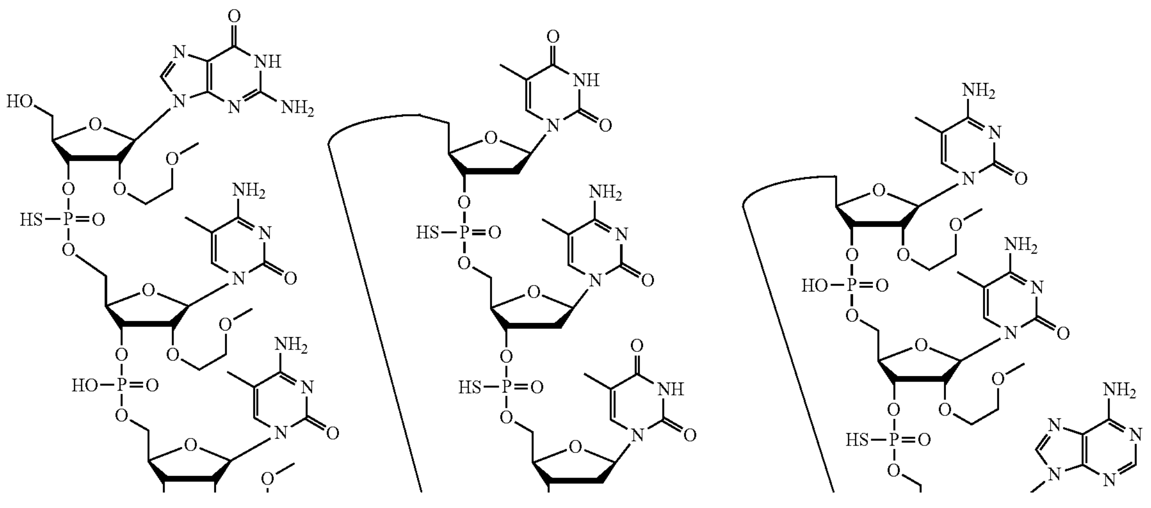

-continued
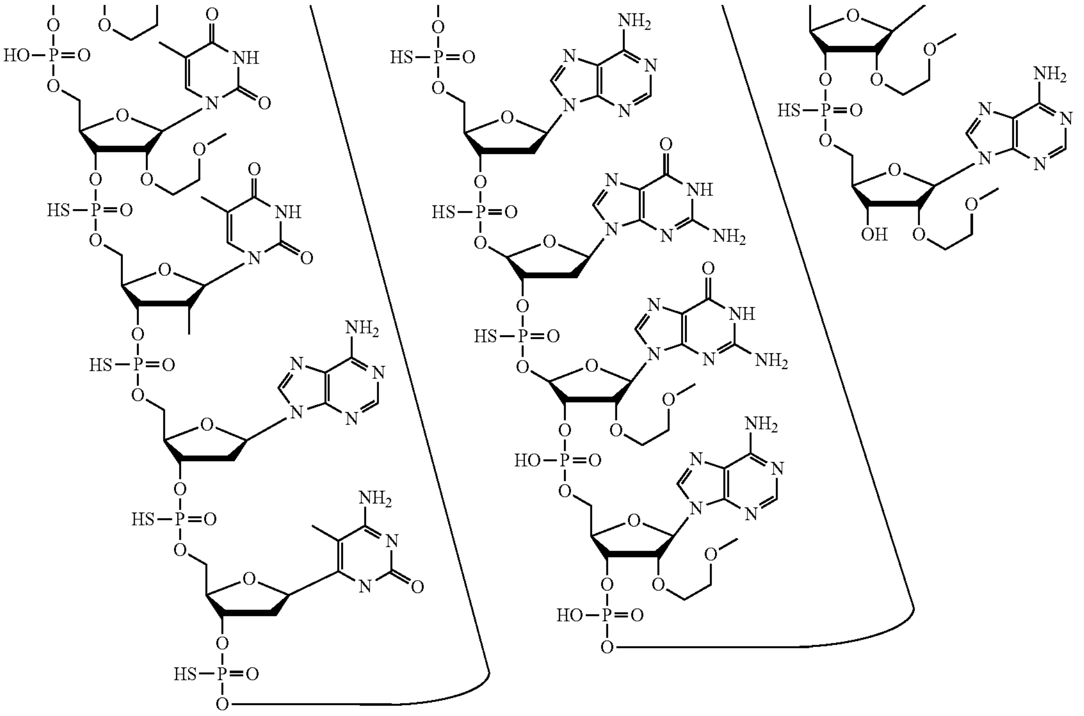
Structure 5. ISIS 802473
In certain embodiments, the sodium salt of ISIS 802473 is described by the following chemical structure:
(SEQ ID NO: 47)
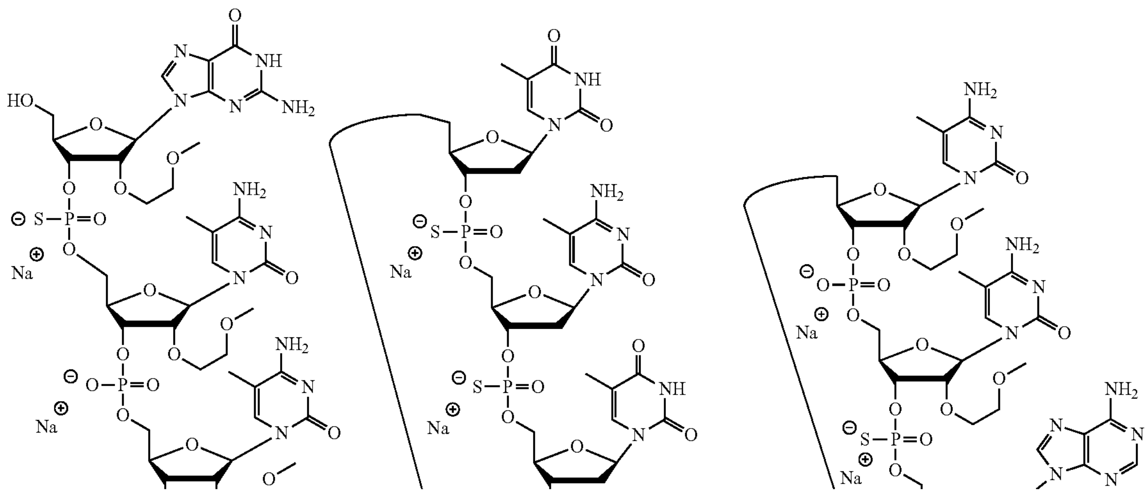

-continued

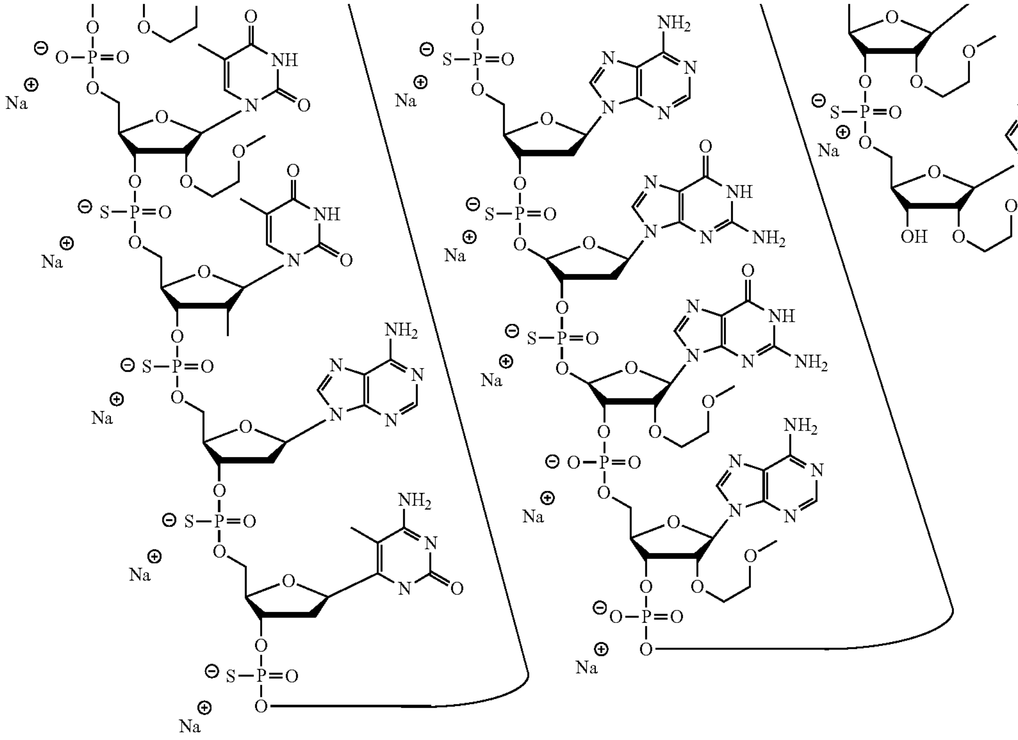

Structure 6. The sodium salt of ISIS 802473

4. ISIS 802459

In certain embodiments, ISIS 802459 is characterized as a 3-10-7 MOE gapmer, having a sequence of (from 5' to 3') GCCTTACTCTAGGACCAAGA (incorporated herein as SEQ ID NO: 21), wherein each of nucleosides 1-3 and 14-20 are 2'—O—methoxyethylribose modified nucleosides, and each of nucleosides 4-13 are 2'-deoxynucleosides, wherein the internucleoside linkages between nucleosides 2 to 3, 3 to 4, 14 to 15, 15 to 16, 16 to 17, and 17 to 18 are phosphodiester linkages and the internucleoside linkages between nucleosides are 1 to 2, 4 to 5, 5 to 6, 6 to 7, 7 to 8, 8 to 9, 9 to 10 10, 10 to 11, 11 to 12, 12 to 13, 13 to 14, 18 to 19, and 19 to 20 are phosphorothioate linkages, and wherein each cytosine is a 5'-methylcytosine.

In certain embodiments, ISIS 802459 is described by the following chemical notation: Ges mCeo mCeo Tds Tds Ads mCds Tds mCds Tds Ads Gds Gds Aeo mCeo mCeo Aeo Aes Ges Ae; wherein, A=an adenine, mC=a 5'-methylcytosine G=a guanine, T=a thymine, e=a 2'—O—methoxyethylribose modified sugar d=a 2'-deoxyribose sugar, s=a phosphorothioate internucleoside linkage, and o=a phosphodiester internucleoside linkage.

In certain embodiments, ISIS 802459 is described by the following chemical structure, or a salt thereof:
(SEQ ID NO: 21)
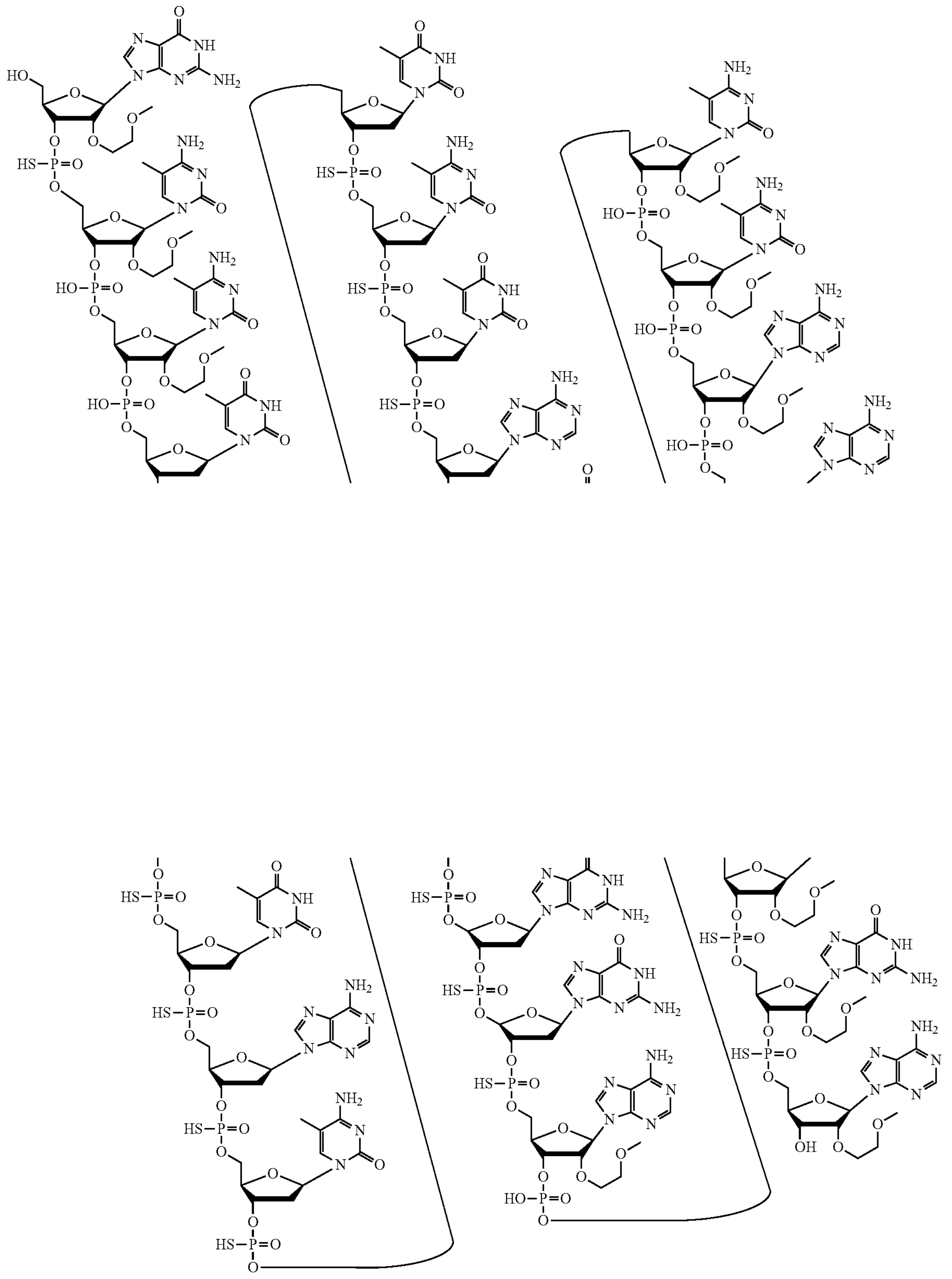

Structure 7. ISIS 802459

In certain embodiments, the sodium salt of ISIS 802459 is described by the following chemical structure:

(SEQ ID NO: 21)

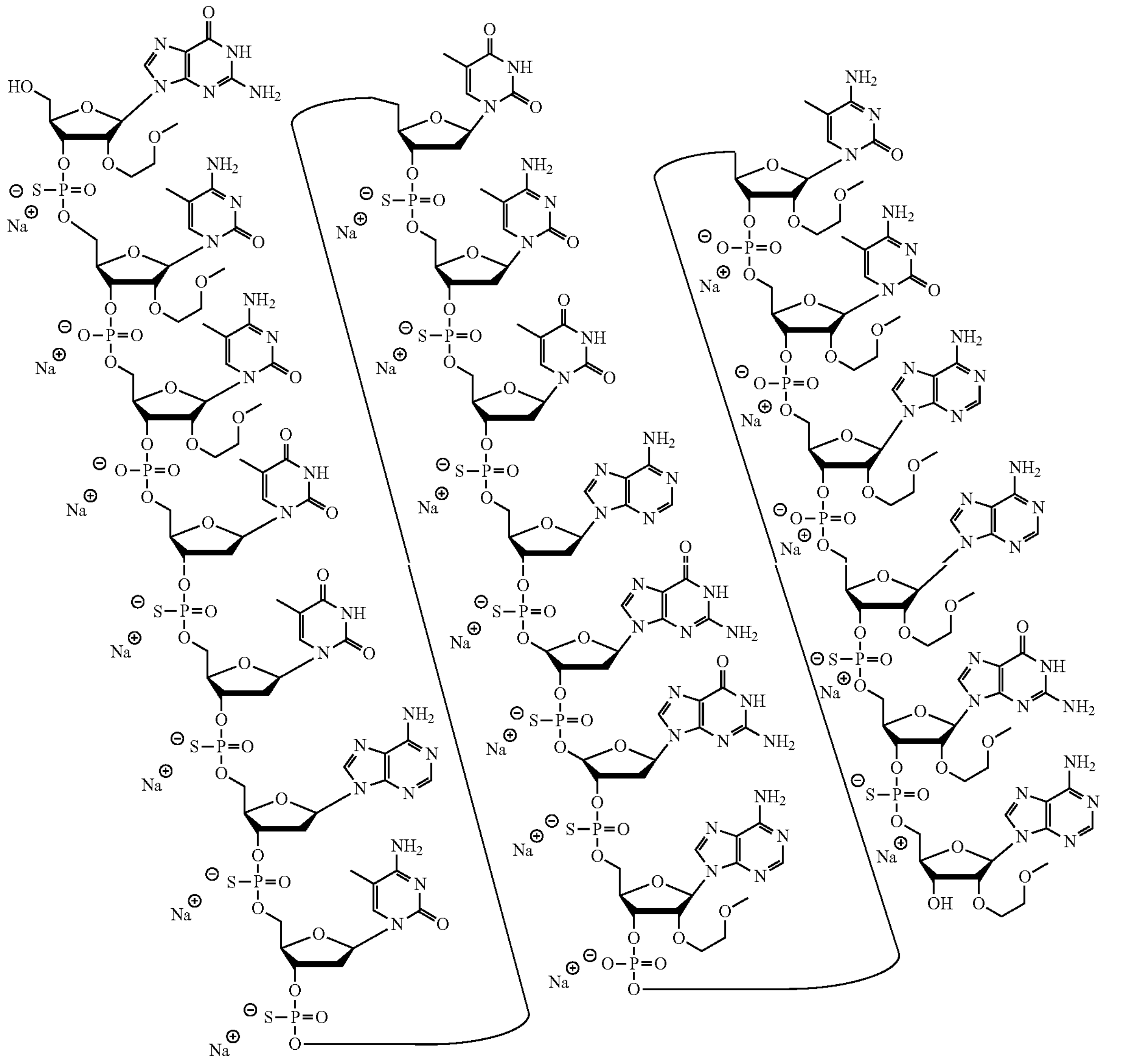

Structure 8. The sodium salt of ISIS 802459

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Oligonucleotides Targeting Human C9ORF72

The antisense oligonucleotides in the table below were designed as MOE gapmers. The central gap segment of each gapmer contains 2'-deoxynucleosides and is flanked by wing segments on both the 5' end and on the 3' end containing nucleosides that each comprise a 2'-MOE group. The specific motif of each gapmer is listed in table below, represented by three numbers separated by hyphens. The numbers represent the number of nucleosides in the 5'-wing, the gap, and the 3'-wing, respectively. All cytosine residues throughout each oligonucleotide are 5-methylcytosines. The internucleoside linkages for the gapmers are mixed phosphorothioate and phosphodiester linkages. The internucleoside linkages for each gapmer are presented in the Linkage column, where 'o' indicates a phosphodiester linkage and's' indicates a phosphorothioate linkage.

Each antisense oligonucleotide listed in the table below is targeted to the human C9ORF72 genomic sequence, designated herein as SEQ ID NO: 2 (the complement of GEN BANK Accession No. NT_008413.18 truncated from nucleosides 27535000 to 27565000). "Start site" indicates the 5'-most nucleoside to which the gapmer is targeted in the human genomic sequence. "Stop site" indicates the 3'-most nucleoside to which the gapmer is targeted human genomic sequence.

TABLE 6

Antisense oligonucleotides targeting human C9ORF72

| Isis No. | Start Site | Stop Site | Sequence | Linkage | Motif | SEQ ID NO |
|---|---|---|---|---|---|---|
| 791656 | 1445 | 1464 | CCGGCCCCTAGCGCGCGACT | soossssssssssooooss | 3-10-7 | 22 |
| 791657 | 1445 | 1464 | CCGGCCCCTAGCGCGCGACT | sooossssssssssoooss | 4-10-6 | 22 |
| 791658 | 1445 | 1464 | CCGGCCCCTAGCGCGCGACT | sooooossssssssssoss | 6-10-4 | 22 |
| 791659 | 1445 | 1464 | CCGGCCCCTAGCGCGCGACT | soooooossssssssssss | 7-10-3 | 22 |
| 791660 | 1445 | 1463 | CGGCCCCTAGCGCGCGACT | soooosssssssssooss | 5-9-5 | 23 |
| 791661 | 1446 | 1464 | CCGGCCCCTAGCGCGCGAC | soooosssssssssooss | 5-9-5 | 24 |
| 791662 | 1445 | 1463 | CGGCCCCTAGCGCGCGACT | sooossssssssssoooss | 4-9-6 | 23 |
| 791663 | 1446 | 1464 | CCGGCCCCTAGCGCGCGAC | sooossssssssssoooss | 4-9-6 | 24 |
| 791664 | 1445 | 1463 | CGGCCCCTAGCGCGCGACT | sooooosssssssssoss | 6-9-4 | 23 |
| 791665 | 1446 | 1464 | CCGGCCCCTAGCGCGCGAC | sooooosssssssssoss | 6-9-4 | 24 |
| 801274 | 1440 | 1459 | CCCTAGCGCGCGACTCCTGA | sooossssssssssoooss | 4-10-6 | 25 |
| 801275 | 1441 | 1460 | CCCCTAGCGCGCGACTCCTG | sooossssssssssoooss | 4-10-6 | 26 |
| 801276 | 1442 | 1461 | GCCCCTAGCGCGCGACTCCT | sooossssssssssoooss | 4-10-6 | 27 |
| 801277 | 1443 | 1462 | GGCCCCTAGCGCGCGACTCC | sooossssssssssoooss | 4-10-6 | 28 |
| 801278 | 1444 | 1463 | CGGCCCCTAGCGCGCGACTC | sooossssssssssoooss | 4-10-6 | 29 |
| 801279 | 1440 | 1459 | CCCTAGCGCGCGACTCCTGA | sooooossssssssssoss | 6-10-4 | 25 |
| 801280 | 1441 | 1460 | CCCCTAGCGCGCGACTCCTG | sooooossssssssssoss | 6-10-4 | 26 |
| 801281 | 1442 | 1461 | GCCCCTAGCGCGCGACTCCT | sooooossssssssssoss | 6-10-4 | 27 |
| 801282 | 1443 | 1462 | GGCCCCTAGCGCGCGACTCC | sooooossssssssssoss | 6-10-4 | 28 |
| 801283 | 1444 | 1463 | CGGCCCCTAGCGCGCGACTC | sooooossssssssssoss | 6-10-4 | 29 |
| 801284 | 1441 | 1458 | CCTAGCGCGCGACTCCTG | soosssssssssoooss | 4-8-6 | 30 |
| 801285 | 1442 | 1459 | CCCTAGCGCGCGACTCCT | soosssssssssoooss | 4-8-6 | 31 |
| 801286 | 1443 | 1460 | CCCCTAGCGCGCGACTCC | soosssssssssoooss | 4-8-6 | 32 |
| 801287 | 1444 | 1461 | GCCCCTAGCGCGCGACTC | soosssssssssoooss | 4-8-6 | 33 |
| 801288 | 1445 | 1462 | GGCCCCTAGCGCGCGACT | soosssssssssoooss | 4-8-6 | 34 |
| 801289 | 1446 | 1463 | CGGCCCCTAGCGCGCGAC | soosssssssssoooss | 4-8-6 | 35 |
| 801290 | 1441 | 1458 | CCTAGCGCGCGACTCCTG | sooooosssssssssoss | 6-8-4 | 30 |
| 801291 | 1442 | 1459 | CCCTAGCGCGCGACTCCT | sooooosssssssssoss | 6-8-4 | 31 |
| 801292 | 1443 | 1460 | CCCCTAGCGCGCGACTCC | sooooosssssssssoss | 6-8-4 | 32 |
| 801293 | 1444 | 1461 | GCCCCTAGCGCGCGACTC | sooooosssssssssoss | 6-8-4 | 33 |
| 801294 | 1445 | 1462 | GGCCCCTAGCGCGCGACT | sooooosssssssssoss | 6-8-4 | 34 |
| 801295 | 1446 | 1463 | CGGCCCCTAGCGCGCGAC | sooooosssssssssoss | 6-8-4 | 35 |
| 801296 | 1403 | 1422 | AGGCTGCGGTTGTTTCCCTC | sooossssssssssoooss | 4-10-6 | 36 |
| 801297 | 1404 | 1423 | CAGGCTGCGGTTGTTTCCCT | sooossssssssssoooss | 4-10-6 | 37 |
| 801298 | 1403 | 1421 | GGCTGCGGTTGTTTCCCTC | soooosssssssssooss | 5-9-5 | 38 |

TABLE 6-continued

| Antisense oligonucleotides targeting human C9ORF72 | | | | | | |
|---|---|---|---|---|---|---|
| Isis No. | Start Site | Stop Site | Sequence | Linkage | Motif | SEQ ID NO |
| 801299 | 1404 | 1422 | AGGCTGCGGTTGTTTCCCT | soooosssssssssooss | 5-9-5 | 39 |
| 801300 | 1405 | 1423 | CAGGCTGCGGTTGTTTCCC | soooosssssssssooss | 5-9-5 | 40 |
| 801301 | 1403 | 1421 | GGCTGCGGTTGTTTCCCTC | sooosssssssssoooss | 4-9-6 | 38 |
| 801302 | 1404 | 1422 | AGGCTGCGGTTGTTTCCCT | sooosssssssssoooss | 4-9-6 | 39 |
| 801303 | 1405 | 1423 | CAGGCTGCGGTTGTTTCCC | sooosssssssssoooss | 4-9-6 | 40 |
| 801304 | 1403 | 1421 | GGCTGCGGTTGTTTCCCTC | sooooosssssssssoss | 6-9-4 | 38 |
| 801305 | 1404 | 1422 | AGGCTGCGGTTGTTTCCCT | sooooosssssssssoss | 6-9-4 | 39 |
| 801306 | 1405 | 1423 | CAGGCTGCGGTTGTTTCCC | sooooosssssssssoss | 6-9-4 | 40 |
| 801307 | 1403 | 1420 | GCTGCGGTTGTTTCCCTC | soosssssssssoooss | 4-8-6 | 41 |
| 801308 | 1404 | 1421 | GGCTGCGGTTGTTTCCCT | soosssssssssoooss | 4-8-6 | 42 |
| 801309 | 1405 | 1422 | AGGCTGCGGTTGTTTCCC | soosssssssssoooss | 4-8-6 | 43 |
| 801310 | 1406 | 1423 | CAGGCTGCGGTTGTTTCC | soosssssssssoooss | 4-8-6 | 44 |
| 801311 | 1403 | 1420 | GCTGCGGTTGTTTCCCTC | soooosssssssssoss | 6-8-4 | 41 |
| 801312 | 1404 | 1421 | GGCTGCGGTTGTTTCCCT | soooosssssssssoss | 6-8-4 | 42 |
| 801313 | 1405 | 1422 | AGGCTGCGGTTGTTTCCC | soooosssssssssoss | 6-8-4 | 43 |
| 801314 | 1406 | 1423 | CAGGCTGCGGTTGTTTCC | soooosssssssssoss | 6-8-4 | 44 |
| 801315 | 1403 | 1422 | AGGCTGCGGTTGTTTCCCTC | sooooossssssssssoss | 6-10-4 | 36 |
| 801316 | 1404 | 1423 | CAGGCTGCGGTTGTTTCCCT | sooooossssssssssoss | 6-10-4 | 37 |
| 802459 | 7990 | 8009 | GCCTTACTCTAGGACCAAGA | soossssssssssooooss | 3-10-7 | 21 |
| 802460 | 8012 | 8031 | TCTGTCTTTGGAGCCCAAAT | soossssssssssooooss | 3-10-7 | 45 |
| 802461 | 8186 | 8205 | CTGCGATCCCCATTCCAGTT | soossssssssssooooss | 3-10-7 | 46 |
| 802462 | 7990 | 8009 | GCCTTACTCTAGGACCAAGA | sooossssssssssoooss | 4-10-6 | 21 |
| 802463 | 8012 | 8031 | TCTGTCTTTGGAGCCCAAAT | sooossssssssssoooss | 4-10-6 | 45 |
| 802464 | 8186 | 8205 | CTGCGATCCCCATTCCAGTT | sooossssssssssoooss | 4-10-6 | 46 |
| 802465 | 7990 | 8009 | GCCTTACTCTAGGACCAAGA | sooooossssssssssoss | 6-10-4 | 21 |
| 802466 | 8012 | 8031 | TCTGTCTTTGGAGCCCAAAT | sooooossssssssssoss | 6-10-4 | 45 |
| 802467 | 8186 | 8205 | CTGCGATCCCCATTCCAGTT | sooooossssssssssoss | 6-10-4 | 46 |
| 802468 | 7990 | 8009 | GCCTTACTCTAGGACCAAGA | soooooossssssssssss | 7-10-3 | 21 |
| 802469 | 8012 | 8031 | TCTGTCTTTGGAGCCCAAAT | soooooossssssssssss | 7-10-3 | 45 |
| 802470 | 8186 | 8205 | CTGCGATCCCCATTCCAGTT | soooooossssssssssss | 7-10-3 | 46 |
| 802471 | 7992 | 8009 | GCCTTACTCTAGGACCAA | sosssssssssooooss | 3-8-7 | 47 |
| 802472 | 8014 | 8031 | TCTGTCTTTGGAGCCCAA | sosssssssssooooss | 3-8-7 | 48 |
| 802473 | 7992 | 8009 | GCCTTACTCTAGGACCAA | soosssssssssoooss | 4-8-6 | 47 |
| 802474 | 8014 | 8031 | TCTGTCTTTGGAGCCCAA | soosssssssssoooss | 4-8-6 | 48 |
| 802475 | 7992 | 8009 | GCCTTACTCTAGGACCAA | soooosssssssssoss | 6-8-4 | 47 |
| 802476 | 8014 | 8031 | TCTGTCTTTGGAGCCCAA | soooosssssssssoss | 6-8-4 | 48 |
| 802477 | 7992 | 8009 | GCCTTACTCTAGGACCAA | sooooosssssssssss | 7-8-3 | 47 |
| 802478 | 8014 | 8031 | TCTGTCTTTGGAGCCCAA | sooooosssssssssss | 7-8-3 | 48 |

TABLE 6-continued

| Antisense oligonucleotides targeting human C9ORF72 | | | | | | |
|---|---|---|---|---|---|---|
| Isis No. | Start Site | Stop Site | Sequence | Linkage | Motif | SEQ ID NO |
| 806673 | 1370 | 1389 | GGTTAATCTTTATCAGGTCT | soossssssssssooooss | 3-10-7 | 49 |
| 806674 | 1371 | 1390 | TGGTTAATCTTTATCAGGTC | soossssssssssooooss | 3-10-7 | 50 |
| 806675 | 1372 | 1391 | CTGGTTAATCTTTATCAGGT | soossssssssssooooss | 3-10-7 | 51 |
| 806676 | 1370 | 1389 | GGTTAATCTTTATCAGGTCT | sooossssssssssoooss | 4-10-6 | 49 |
| 806677 | 1371 | 1390 | TGGTTAATCTTTATCAGGTC | sooossssssssssoooss | 4-10-6 | 50 |
| 806678 | 1372 | 1391 | CTGGTTAATCTTTATCAGGT | sooossssssssssoooss | 4-10-6 | 51 |
| 806679 | 1370 | 1389 | GGTTAATCTTTATCAGGTCT | sooooossssssssssoss | 6-10-4 | 49 |
| 806680 | 1371 | 1390 | TGGTTAATCTTTATCAGGTC | sooooossssssssssoss | 6-10-4 | 50 |
| 806681 | 1372 | 1391 | CTGGTTAATCTTTATCAGGT | sooooossssssssssoss | 6-10-4 | 51 |
| 806682 | 1370 | 1389 | GGTTAATCTTTATCAGGTCT | soooooossssssssssss | 7-10-3 | 49 |
| 806683 | 1371 | 1390 | TGGTTAATCTTTATCAGGTC | soooooossssssssssss | 7-10-3 | 50 |
| 806684 | 1372 | 1391 | CTGGTTAATCTTTATCAGGT | soooooossssssssssss | 7-10-3 | 51 |
| 806685 | 1371 | 1388 | GTTAATCTTTATCAGGTC | soosssssssssoooss | 4-8-6 | 52 |
| 806686 | 1372 | 1389 | GGTTAATCTTTATCAGGT | soosssssssssoooss | 4-8-6 | 53 |
| 806687 | 1373 | 1390 | TGGTTAATCTTTATCAGG | soosssssssssoooss | 4-8-6 | 54 |
| 806688 | 1440 | 1457 | CTAGCGCGCGACTCCTGA | soosssssssssoooss | 4-8-6 | 55 |
| 806689 | 1371 | 1388 | GTTAATCTTTATCAGGTC | soooosssssssssoss | 6-8-4 | 52 |
| 806690 | 1372 | 1389 | GGTTAATCTTTATCAGGT | soooosssssssssoss | 6-8-4 | 53 |
| 806691 | 1373 | 1390 | TGGTTAATCTTTATCAGG | soooosssssssssoss | 6-8-4 | 54 |
| 806692 | 1440 | 1457 | CTAGCGCGCGACTCCTGA | soooosssssssssoss | 6-8-4 | 55 |

Example 2: Tolerability of Antisense Oligonucleotides Targeting Human C9ORF72 in Mice Antisense oligonucleotides described above were tested in mice to assess tolerability of the oligonucleotides. Wild type C57/B16 mice each received a single ICV dose of 700 μg of an antisense oligonucleotide listed in the table below. Each treatment group consisted of 4 mice. At 3 hours post injection, each mouse was evaluated according to 7 different criteria. The 7 criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the 700 μg ICV dose, and met all other criteria, it would get a summed score of 0. If another mouse was not bright, alert, and responsive 3 hours after the 700 μg ICV dose but met all other criteria, it would receive a score of 1. The results are presented as the average score for each treatment group.

TABLE 7

| Acute tolerability scores | |
|---|---|
| Isis No. | Score |
| 791656 | 3.25 |
| 791657 | 4.25 |
| 791658 | 3.50 |
| 791659 | 2.00 |
| 791660 | 4.00 |
| 791661 | 4.50 |
| 791662 | 5.25 |
| 791663 | 6.00 |
| 791664 | 3.00 |
| 791665 | 5.75 |
| 801274 | 1.75 |
| 801275 | 3.75 |
| 801276 | 1.25 |
| 801277 | 1.50 |
| 801278 | 1.75 |
| 801279 | 1.25 |
| 801280 | 6.00 |
| 801281 | 0.00 |
| 801282 | 1.25 |
| 801283 | 1.25 |
| 801284 | 3.00 |
| 801285 | 1.00 |
| 801286 | 1.00 |
| 801287 | 1.50 |
| 801288 | 2.50 |

TABLE 7-continued

| Acute tolerability scores | |
|---|---|
| Isis No. | Score |
| 801289 | 7.00 |
| 801290 | 6.00 |
| 801291 | 3.00 |
| 801292 | 2.00 |
| 801293 | 1.00 |
| 801294 | 3.25 |
| 801295 | 4.50 |
| 801296 | 6.25 |
| 801297 | 4.75 |
| 801298 | 5.50 |
| 801299 | 6.25 |
| 801300 | 5.00 |
| 801301 | 6.00 |
| 801302 | 6.50 |
| 801303 | 4.00 |
| 801304 | 5.25 |
| 801305 | 6.00 |
| 801306 | 6.00 |
| 801307 | 5.00 |
| 801308 | 6.00 |
| 801309 | 7.00 |
| 801310 | 3.50 |
| 801311 | 5.50 |
| 801312 | 2.50 |
| 801313 | 5.25 |
| 801314 | 4.50 |
| 801315 | 4.00 |
| 801316 | 2.00 |
| 802459 | 2.00 |
| 802460 | 6.75 |
| 802461 | 1.75 |
| 802462 | 5.75 |
| 802463 | 6.75 |
| 802464 | 1.75 |
| 802465 | 2.25 |
| 802466 | 4.25 |
| 802467 | 0.25 |
| 802468 | 3.25 |
| 802469 | 2.00 |
| 802470 | 0.25 |
| 802471 | 1.25 |
| 802472 | 4.00 |
| 802473 | 0.25 |
| 802474 | 5.25 |
| 802475 | 1.00 |
| 802476 | 5.50 |
| 802477 | 2.50 |
| 802478 | 6.25 |
| 806673 | 0.00 |
| 806674 | 0.25 |
| 806675 | 0.00 |
| 806676 | 0.00 |
| 806677 | 1.00 |
| 806678 | 0.00 |
| 806679 | 1.50 |
| 806680 | 1.00 |
| 806681 | 0.00 |
| 806682 | 5.75 |
| 806683 | 3.75 |
| 806684 | 2.25 |
| 806685 | 1.00 |
| 806686 | 1.00 |
| 806687 | 3.25 |
| 806688 | 3.25 |
| 806689 | 3.00 |
| 806690 | 1.25 |
| 806691 | 6.25 |

Example 3: Tolerability of Oligonucleotides from WO 2014/062691

Oligonucleotides described in WO 2014/062691 were tested in an acute tolerability study in mice. Groups of 3 wild type C57/B16 mice were treated and analyzed as described in Example 2. The tested oligonucleotides include those listed in the table below, which are 5-10-5 MOE gapmers with a full phosphorothioate backbone and each cytosine is a 5-methylcytosine. The start and stop sites on SEQ ID NO: 2 that each oligonucleotide is targeted to are shown. The results are presented as the average score for each treatment group in the table below. These results demonstrate that ISIS 576816, ISIS 576974, ISIS 577061, ISIS 577065, ISIS 577083, and ISIS 577056 were poorly tolerated.

TABLE 8

Acute tolerability scores 3 h after treatment with antisense oligonucleotides from WO 2014/062691

| Isis No. | Start site | Stop site | Sequence | Score | SEQ ID NO |
|---|---|---|---|---|---|
| 576816 | 7990 | 8009 | GCCTTACTCTAGGACCAAGA | 7.00 | 21 |
| 576974 | 28251 | 28270 | GGGACACTACAAGGTAGTAT | 5.67 | 56 |
| 577061 | 1406 | 1425 | TACAGGCTGCGGTTGTTTCC | 7.00 | 57 |
| 577065 | 1446 | 1465 | CCCGGCCCCTAGCGCGCGAC | 6.00 | 58 |
| 577083 | 3452 | 3471 | GGTAACTTCAAACTCTTGGG | 7.00 | 59 |

TABLE 9

Acute tolerability scores 3 h after treatment with antisense oligonucleotides from WO 2014/062691

| Isis No. | Start site | Stop site | Sequence | Score | SEQ ID NO |
|---|---|---|---|---|---|
| 577056 | 1366 | 1385 | AATCTTTATCAGGTCTTTTC | 6.5 | 60 |

Example 4: Antisense Inhibition of a Human C9ORF72 mRNA Variant in HepG2 Cells Antisense oligonucleotides described above are tested for their effects on C9ORF72 mRNA in vitro. Cultured HepG2 cells at a density of 20,000 cells per well are electroporated with an antisense oligonucleotide. After a treatment period of approximately 24 hours, RNA is isolated from the cells and C90RF72 mRNA levels are measured by quantitative real-time PCR. Human primer probe set RTS3905 (forward primer sequence GGGTCTAGCAAGAGCAGGTG, designated herein as SEQ ID NO: 12; reverse primer sequence GTCTTGGCAACAGCTGGAGAT, designated herein as SEQ ID NO: 13; probe sequence TGATGTCGACTCTTTGCCCACCGC, designated herein as SEQ ID NO: 14-a TAQ-man primer probe set) are used. RTS3905 detects an mRNA variant (e.g. NM_001256054.1) processed from a pre-mRNA variant containing the hexanucleotide repeat. The mRNA variant processed from a pre-mRNA variant containing the hexanucleotide repeat is herein the “C9ORF72 pathogenic associated mRNA variant.” A pre-mRNA contains the hexanucleotide repeat when transcription of the pre-mRNA begins in the region from the start site of exon 1A to the start site of exon 1B (generally nucleotides 1107 to 1520 of the genomic sequence: SEQ ID NO: 2, the complement of GENBANK Accession No. NT_008413.18 truncated from nucleosides 27535000 to 2756500. Therefore, oligonucleotides designed in this region selectively target the pre-mRNA variant containing the hexanucleotide repeat. RTS3905 measures an mRNA product (i.e. the C9ORF72 pathogenic associated mRNA variant) of the pre-mRNA variant containing the hexanucleotide repeat and, therefore, measures the reduction of the pre-mRNA variant containing the hexanucleotide repeat. The levels of the C90RF72 pathogenic associated mRNA variant are normalized to the total RNA content of the cell, as measured by RIBOGREEN®, then the normalized mRNA variant levels are compared to those of cells that were not treated with antisense oligonucleotide.

Example 5: Dose-Dependent Antisense Inhibition of a Human C9ORF72 mRNA Variant Antisense oligonucleotides described above are tested at various doses in HepG2 cells. Cells are plated at a density of 20,000 cells per well and electroporated with antisense oligonucleotide. After a treatment period of approximately 16 hours or 24 hours, RNA is isolated from the cells and C9ORF72 mRNA levels are measured by quantitative real-time PCR. Human C9ORF72 primer probe set RTS3905 is used to measure the C9ORF72 pathogenic associated mRNA variant. The levels of the C9ORF72 pathogenic associated mRNA variant are adjusted according to total RNA content, as measured by RIBOGREEN®. The half maximal inhibitory concentration (IC50) of each oligonucleotide is calculated based on the inhibition of mRNA variant levels observed at each individual dose of antisense oligonucleotide.

Example 6: Antisense Inhibition of C9ORF72 by Human-Rhesus Cross-Reactive Antisense Oligonucleotides in LLC-MK2 Cells Antisense oligonucleotides described above that are fully cross-reactive with a rhesus C9ORF72 nucleic acid are tested for their effects on rhesus C9ORF72 mRNA in vitro. Cultured rhesus LLC-MK2 cells at a density of 20,000 cells per well are electroporated with antisense oligonucleotide. After a treatment period of approximately 24 hours, RNA is isolated from the cells and C9ORF72 mRNA levels are measured by quantitative real-time PCR. Primer probe set RTS3750 (forward sequence TGTGACAGTTGGAATGCAGTGA, designated herein as SEQ ID NO: 15; reverse sequence GCCACTTAAAGCAATCTCTGTCTTG, designated herein as SEQ ID NO: 16; probe sequence TCGACTCTTTGCCCACCGCCA, designated herein as SEQ ID NO: 17-a TAQ-man primer probe set) is used to measure total C9ORF72 mRNA levels. RTS3750 targets exon 2 of the mRNA transcripts and, therefore, measures total mRNA transcripts. C9ORF72 mRNA levels are adjusted according to total RNA content, as measured by RIBOGREEN®, then the normalized mRNA variant levels are compared to those of cells that were not treated with antisense oligonucleotide.

Example 7: Dose-Dependent Antisense Inhibition of Human C9ORF72 mRNA in LLC-MK2

Antisense oligonucleotides described above are tested at various doses in LLC-MK2 cells. Cells are plated at a density of 20,000 cells per well and electroporated with antisense oligonucleotide. After a treatment period of approximately 16 hours or 24 hours, RNA is isolated from the cells and C9ORF72 mRNA levels are measured by quantitative real-time PCR. Primer probe set RTS3750 is used to measure total C90RF72 mRNA levels. C9ORF72 mRNA levels are adjusted according to total RNA content, as measured by RIBOGREEN®, then the normalized mRNA variant levels are compared to those of cells that were not treated with antisense oligonucleotide.

Example 8: Antisense Inhibition of Human C9ORF72 mRNA in a Transgenic Mouse Model Antisense oligonucleotides described above are tested in two BAC transgenic mouse lines, designated herein as C9B41 and C9B183, that each express a truncated human C9ORF72 gene comprising exons 1-5. The truncated human C9ORF72 genes of the C9B41 and C9B183 mouse lines comprise 110 and 450 hexanucleotide repeats, respectively. Each mouse in each treatment group receives 350 μg of an antisense oligonucleotide, then expression levels of human C9ORF72 RNA are analyzed by RT-PCR. Dose responses are also performed.

Example 9: Antisense Inhibition of C9ORF72 mRNA in Patient Fibroblasts

Antisense oligonucleotides described above were tested for their effects on C9ORF72 mRNA in vitro. The antisense oligonucleotides listed in the table below were added to a plate before patient fibroblasts F09-152 were added at a density of 20,000 cells per well. The final concentrations of the antisense oligonucleotides after the addition of the cells are listed in the table below. After 30 seconds of shaking, the cells were electroporated then transferred to a Primaria coated culture plate. After 16 hours, RNA was isolated from the cells, and levels of total C9ORF72 mRNA (i.e., mRNA starting from exon 1A and mRNA starting from exon 1B) and levels of the pathogenic associated mRNA (see Example 4) were measured by RT-qPCR. Human primer probe sets RTS 3750 (see Example 6) and RTS3905 (see Example 4) were used to detect the total C9ORF72 mRNA and C9ORF72 pathogenic associated mRNA, respectively. The levels of the C9ORF72 total mRNA and C9ORF72 pathogenic associated mRNA were normalized to the total RNA content of the cell, as measured by RIBOGREEN®, then the normalized mRNA levels were compared to those of cells that were not treated with antisense oligonucleotide. The results are shown in the table below. An entry of "nd" means not determined. IC50 values listed as "nd" were not determined, because the target was not inhibited sufficiently to determine an IC50. The results show that all of the oligonucleotides listed below inhibited the pathogenic associated C9ORF72 mRNA variant. Oligonucleotides that do not specifically target the repeat variant pre-mRNA inhibited both the pathogenic associated C9ORF72 mRNA and total C90RF72 mRNA. Oligonucleotides that specifically target the repeat variant pre-mRNA selectively inhibited the pathogenic associated C9ORF72 mRNA.

TABLE 10

C9ORF72 mRNA levels following antisense inhibition in patient fibroblasts

| | Concentration | Total C9ORF72 mRNA | | Pathogenic associated C9ORF72 mRNA | |
|---|---|---|---|---|---|
| Isis No. | (μM) | Level (% UTC) | $IC_{50}$ (μM) | Level (% UTC) | $IC_{50}$ (μM) |
| 791658 | 0.12 | 87 | nd | 26 | <0.1 |
| | 0.60 | 80 | | 9 | |
| | 3.00 | 87 | | nd | |
| | 15.00 | 105 | | 4 | |
| 791664 | 0.12 | 85 | nd | 13 | <0.1 |
| | 0.60 | 101 | | 7 | |
| | 3.00 | 125 | | 4 | |
| | 15.00 | 114 | | 3 | |
| 801278 | 0.12 | 91 | nd | 19 | <0.1 |
| | 0.60 | 71 | | 7 | |
| | 3.00 | 85 | | nd | |
| | 15.00 | 90 | | nd | |
| 801279 | 0.12 | 98 | nd | 57 | 0.12 |
| | 0.60 | 77 | | 27 | |
| | 3.00 | 77 | | 3 | |
| | 15.00 | 86 | | 5 | |
| 801282 | 0.12 | 100 | nd | 51 | 0.08 |
| | 0.60 | 84 | | 12 | |
| | 3.00 | 97 | | 6 | |
| | 15.00 | 190 | | nd | |
| 801283 | 0.12 | 87 | nd | 40 | <0.1 |
| | 0.60 | 75 | | 8 | |
| | 3.00 | 94 | | 4 | |
| | 15.00 | 111 | | 4 | |
| 801285 | 0.12 | 103 | nd | 35 | <0.1 |
| | 0.60 | 78 | | 23 | |
| | 3.00 | 75 | | 7 | |
| | 15.00 | 79 | | 6 | |
| 801286 | 0.12 | 94 | nd | 33 | <0.1 |
| | 0.60 | 85 | | 14 | |
| | 3.00 | 97 | | 5 | |
| | 15.00 | 88 | | 3 | |
| 801287 | 0.12 | 85 | nd | 31 | <0.1 |
| | 0.60 | 76 | | 11 | |
| | 3.00 | 77 | | 9 | |
| | 15.00 | 87 | | 2 | |
| 801288 | 0.12 | 77 | nd | 13 | <0.1 |
| | 0.60 | 86 | | 11 | |
| | 3.00 | 123 | | 5 | |
| | 15.00 | 177 | | 3 | |
| 801292 | 0.12 | 69 | nd | 29 | <0.1 |
| | 0.60 | 71 | | 12 | |
| | 3.00 | 82 | | 3 | |
| | 15.00 | 71 | | nd | |
| 801293 | 0.12 | 77 | nd | 51 | 0.09 |
| | 0.60 | 70 | | 10 | |
| | 3.00 | 74 | | 3 | |
| | 15.00 | 81 | | 1 | |
| 801294 | 0.12 | 75 | nd | 27 | <0.1 |
| | 0.60 | 67 | | 9 | |
| | 3.00 | 107 | | 7 | |
| | 15.00 | 146 | | 2 | |
| 801316 | 0.12 | 73 | nd | 35 | <0.1 |
| | 0.60 | 68 | | 7 | |
| | 3.00 | 65 | | 1 | |
| | 15.00 | 78 | | 1 | |
| 802459 | 0.12 | 58 | 0.10 | 75 | 0.18 |
| | 0.60 | 15 | | 6 | |
| | 3.00 | 2 | | 11 | |
| | 15.00 | 1 | | 6 | |
| 802464 | 0.12 | 81 | 0.39 | 69 | 0.21 |
| | 0.60 | 31 | | 23 | |
| | 3.00 | 6 | | 7 | |
| | 15.00 | 2 | | 3 | |
| 802465 | 0.12 | 40 | <0.1 | 35 | <0.1 |
| | 0.60 | 7 | | 7 | |
| | 3.00 | 2 | | nd | |
| | 15.00 | 1 | | nd | |
| 802468 | 0.12 | 52 | 0.10 | 40 | <0.1 |
| | 0.60 | 15 | | 13 | |
| | 3.00 | 3 | | 7 | |
| | 15.00 | 2 | | nd | |
| 802469 | 0.12 | 69 | 0.17 | 57 | ~0.5 |
| | 0.60 | 16 | | 9 | |

TABLE 10-continued

C9ORF72 mRNA levels following antisense inhibition in patient fibroblasts

| | Concentration | Total C9ORF72 mRNA | | Pathogenic associated C9ORF72 mRNA | |
|---|---|---|---|---|---|
| Isis No. | (μM) | Level (% UTC) | $IC_{50}$ (μM) | Level (% UTC) | $IC_{50}$ (μM) |
| | 3.00 | 4 | | nd | |
| | 15.00 | 1 | | nd | |
| 802471 | 0.12 | 71 | 0.27 | 54 | 0.12 |
| | 0.60 | 29 | | 20 | |
| | 3.00 | 6 | | 6 | |
| | 15.00 | 7 | | nd | |
| 802473 | 0.12 | 63 | 0.18 | 48 | <0.1 |
| | 0.60 | 27 | | 14 | |
| | 3.00 | 8 | | 11 | |
| | 15.00 | 4 | | nd | |
| 802477 | 0.12 | 54 | 0.12 | 32 | <0.1 |
| | 0.60 | 16 | | 12 | |
| | 3.00 | 4 | | 11 | |
| | 15.00 | 3 | | 3 | |
| 806676 | 0.12 | 66 | nd | 20 | <0.1 |
| | 0.60 | 66 | | 4 | |
| | 3.00 | 76 | | 2 | |
| | 15.00 | 64 | | nd | |
| 806679 | 0.12 | 71 | nd | 23 | <0.1 |
| | 0.60 | 68 | | 2 | |
| | 3.00 | 78 | | 1 | |
| | 15.00 | 84 | | 1 | |
| 806680 | 0.12 | 89 | nd | 41 | <0.1 |
| | 0.60 | 76 | | 13 | |
| | 3.00 | 65 | | 7 | |
| | 15.00 | 84 | | nd | |
| 806690 | 0.12 | 99 | nd | 44 | <0.1 |
| | 0.60 | 88 | | 17 | |
| | 3.00 | 85 | | 2 | |
| | 15.00 | 77 | | 1 | |

Example 10: Antisense Inhibition of Human C9ORF72 mRNA in a Transgenic Mouse Model Antisense oligonucleotides described above were tested in a BAC transgenic mouse line, C9B41 (see Example 8), that expresses a human C9ORF72 gene comprising the promoter region through exon 5 and 110 hexanucleotide repeats. Each treatment group consisted of 2-3 mice. Each mouse received a single ICVB of 350 μg of an antisense oligonucleotide listed in the tables below or PBS. Two weeks later, the mice were euthanized, and expression levels of the human pathogenic associated C9ORF72 mRNA variant and/or total human C9ORF72 mRNA were analyzed by RT-qPCR as described in Example 9. Analysis of the pathogenic associated C9ORF72 variant mRNA levels was not completed for the oligonucleotides that do not specifically target the C9ORF72 repeat variant pre-mRNA. The results in the tables below show the average percent normalized human C9ORF72 mRNA levels relative to the normalized average for the PBS treated group.

TABLE 11

Human C9ORF72 mRNA levels following antisense inhibition in transgenic mice

| | Spinal Cord (% PBS treated) | | Cortex (% PBS treated) | |
|---|---|---|---|---|
| Isis No. | Pathogenic variant | Total | Pathogenic variant | Total |
| 791658 | 6 | 69 | 12 | 47 |
| 791659 | 18 | 72 | 27 | 57 |
| 791664 | 13 | 55 | 15 | 39 |
| 801274 | 49 | 65 | 27 | 37 |

TABLE 11-continued

Human C9ORF72 mRNA levels following antisense inhibition in transgenic mice

| | Spinal Cord (% PBS treated) | | Cortex (% PBS treated) | |
|---|---|---|---|---|
| Isis No. | Pathogenic variant | Total | Pathogenic variant | Total |
| 801276 | 10 | 47 | 12 | 29 |
| 801277 | 9 | 44 | 10 | 28 |
| 801278 | 8 | 39 | 10 | 27 |
| 801279 | 33 | 55 | 40 | 47 |
| 801281 | 16 | 48 | 17 | 32 |
| 801282 | 18 | 49 | 31 | 42 |
| 801283 | 15 | 46 | 17 | 31 |
| 801285 | 29 | 51 | 24 | 36 |
| 801286 | 37 | 61 | 37 | 47 |
| 801287 | 13 | 47 | 30 | 40 |
| 801288 | 18 | 52 | 39 | 48 |
| 801292 | 25 | 49 | 33 | 40 |
| 801293 | 20 | 50 | 29 | 38 |
| 801310 | 70 | 80 | 68 | 70 |
| 801312 | 43 | 61 | 46 | 55 |
| 801315 | 39 | 59 | 41 | 51 |
| 801316 | 27 | 56 | 50 | 58 |
| 806673 | 38 | 66 | 66 | 66 |
| 806674 | 78 | 88 | 98 | 96 |
| 806675 | 67 | 86 | 81 | 85 |
| 806676 | 29 | 64 | 52 | 58 |
| 806677 | 61 | 77 | 69 | 68 |
| 806678 | 83 | 96 | 95 | 102 |
| 806679 | 24 | 63 | 26 | 44 |
| 806680 | 29 | 62 | 41 | 56 |
| 806681 | 39 | 68 | 36 | 54 |
| 806684 | 44 | 69 | 62 | 64 |
| 806685 | 69 | 87 | 56 | 58 |
| 806686 | 59 | 75 | 57 | 68 |
| 806687 | 74 | 88 | 77 | 80 |

TABLE 11-continued

Human C9ORF72 mRNA levels following antisense inhibition in transgenic mice

| | Spinal Cord (% PBS treated) | | Cortex (% PBS treated) | |
|---|---|---|---|---|
| Isis No. | Pathogenic variant | Total | Pathogenic variant | Total |
| 806688 | 34 | 62 | 42 | 51 |
| 806689 | 67 | 92 | 87 | 88 |
| 806690 | 28 | 61 | 57 | 68 |
| 806692 | 45 | 64 | 44 | 50 |

TABLE 12

Human C9ORF72 mRNA levels following antisense inhibition in transgenic mice

| | Total human C9ORF72 mRNA (% PBS) | |
|---|---|---|
| Isis No. | Spinal Cord | Cortex |
| 802459 | 28 | 30 |
| 802461 | 22 | 19 |
| 802464 | 30 | 28 |
| 802465 | 25 | 25 |
| 802467 | 13 | 14 |
| 802468 | 24 | 26 |
| 802469 | 24 | 20 |
| 802470 | 18 | 20 |
| 802471 | 36 | 44 |
| 802473 | 28 | 38 |
| 802475 | 15 | 15 |
| 802477 | 14 | 15 |

Example 11: Dose Dependent Antisense Inhibition of Human C9ORF72 mRNA in a Transgenic Mouse Model Antisense oligonucleotides described above were tested in two BAC transgenic mouse lines, C9B41 and C9B183, that each express a truncated human C9ORF72 gene comprising exons 1-5. The truncated human C9ORF72 genes of the C9B41 and C9B183 mouse lines comprise 110 and 450 hexanucleotide repeats, respectively (see Example 8). Each treatment group consisted of 2-4 mice. Each mouse received a single ICVB of 30 μg, 100 μg, 300 μg, or 700 μg of an antisense oligonucleotide as listed in the tables below or PBS. Two weeks later, the mice were euthanized, and expression levels of the human pathogenic associated C9ORF72 mRNA variant and/or total human C9ORF72 mRNA were analyzed by RT-qPCR as described in Example 9. The results in the tables below show the average percent normalized human C90RF72 mRNA levels relative to the normalized average for the PBS treated group. A value of 100 or greater means the antisense oligonucleotide did not reduce mRNA or increased the amount of mRNA.

TABLE 13

Human C9ORF72 mRNA levels following dose dependnent antisense inhibition in C9B41 transgenic mice

| Isis No. | Concentration (μg) | Spinal Cord (% PBS treated) Total C9 | Cortex (% PBS treated) Total C9 |
|---|---|---|---|
| 802459 | 30 | 84 | 85 |
| | 100 | 63 | 61 |
| | 300 | 33 | 26 |
| | 700 | 29 | 17 |

TABLE 13-continued

Human C9ORF72 mRNA levels following dose dependnent antisense inhibition in C9B41 transgenic mice

| Isis No. | Concentration (μg) | Spinal Cord (% PBS treated) Total C9 | Cortex (% PBS treated) Total C9 |
|---|---|---|---|
| 802473 | 30 | 74 | 90 |
| | 100 | 60 | 77 |
| | 300 | 37 | 39 |
| | 700 | 28 | 26 |

TABLE 14

Human C9ORF72 mRNA levels following dose dependnent antisense inhibition in C9B183 transgenic mice

| Isis No. | Concentration (μg) | Spinal Cord (% PBS treated) Pathogenic variant | Cortex (% PBS treated) Pathogenic variant |
|---|---|---|---|
| 801287 | 30 | 76 | 10 |
| | 100 | 37 | 75 |
| | 300 | 21 | 32 |
| | 700 | 11 | 15 |
| 806679 | 30 | 72 | 13 |
| | 100 | 59 | 100 |
| | 300 | 21 | 61 |
| | 700 | 10 | 16 |
| 806680 | 30 | 94 | 118 |
| | 100 | 72 | 97 |
| | 300 | 34 | 89 |
| | 700 | 30 | 56 |
| 806690 | 30 | 52 | 125 |
| | 100 | 60 | 131 |
| | 300 | 43 | 119 |
| | 700 | 19 | 49 |

Example 12: Tolerability of Antisense Oligonucleotides Targeting Human $C_9$Orf72 in Mice Wild type C57/B16 mice each received a single ICV dose of 700 μg of an antisense oligonucleotide listed in the table below, as described in Example 2. Each treatment group consisted of 4 mice. At 8 weeks post-injection, mice were evaluated according to 7 different criteria. The criteria are (1) the mouse was bright, alert, and responsive; (2) the mouse was standing or hunched without stimuli; (3) the mouse showed any movement without stimuli; (4) the mouse demonstrated forward movement after it was lifted; (5) the mouse demonstrated any movement after it was lifted; (6) the mouse responded to tail pinching; (7) regular breathing. For each of the 7 criteria, a mouse was given a subscore of 0 if it met the criteria and 1 if it did not. After all 7 criteria were evaluated, the scores were summed for each mouse and averaged within each treatment group. The results are presented in the table below.

Animals were sacrificed at 8 weeks. The cortex and spinal cord were collected from each animal, and RT-PCR was performed. Expression levels of allograft inflammatory factor (AIF1) were determined as a measure of inflammation. Expression levels of glial fibrillary acidic protein (GFAP) were also determined as a measure of glial cell activation. Results were normalized to Gpadh and are presented relative to PBS control (1.0) in the table below. "N.D." indicates there was no data because the experiment was not performed. An asterisk indicates that the corresponding result is the average of 1-3 mice.

TABLE 15

| Tolerabilty of antisense oligonucleotides targeting C9Orf72 in mice | | | | | | |
|---|---|---|---|---|---|---|
| ISIS No. | Score 8 weeks after injection | AIF1 (spinal cord) | AIF1 (cere-bellum) | GFAP (spinal cord) | GFAP (cortex) | SEQ ID NO. |
| 791656 | 3.5 | 1.1* | 1.3* | 1.0* | 1.3* | 22 |
| 791657 | 3.5 | 2.3* | 1.0* | 1.4* | 0.8* | 22 |
| 791658 | 0.0 | 1.9 | 1.2 | 1.4 | 1.3 | 22 |
| 791659 | 0.0 | 1.8 | 1.3 | 1.5 | 2.5 | 22 |
| 791660 | 1.8 | 2.5* | 1.4* | 1.9* | 0.8* | 23 |
| 791661 | 1.8 | 1.7* | 1.3* | 1.5* | 1.1* | 24 |
| 791662 | 5.3 | 1.1* | 1.2* | 1.1* | 0.8* | 23 |
| 791663 | 7.0 | N.D. | N.D. | N.D. | N.D. | 24 |
| 791664 | 0.0 | 1.6 | 1.6 | 1.2 | 0.9 | 23 |
| 791665 | 3.5 | 1.9* | 1.5* | 1.9* | 0.9* | 24 |
| 801274 | 0.0 | 1.2 | 1.3 | 1.3 | 1.1 | 25 |
| 801275 | 3.5 | 1.4* | 1.7* | 1.6* | 2.1* | 26 |
| 801276 | 0.0 | 13.1 | 2.6 | 3.7 | 1.2 | 27 |
| 801277 | 0.0 | 2.9 | 1.4 | 2.3 | 1.5 | 28 |
| 801278 | 0.0 | 2.0 | 1.3 | 1.8 | 1.1 | 29 |
| 801279 | 0.0 | 1.2 | 1.4 | 1.3 | 1.0 | 25 |
| 801280 | 5.3 | 1.5* | 1.5* | 1.4* | 1.2* | 26 |
| 801281 | 0.0 | 3.6 | 2.2 | 2.4 | 1.6 | 27 |
| 801282 | 0.0 | 1.2 | 1.2 | 1.2 | 1.0 | 28 |
| 801283 | 0.0 | 1.4 | 1.4 | 1.0 | 0.9 | 29 |
| 801284 | 1.8 | 1.2* | 1.5* | 0.9* | 1.0* | 30 |
| 801285 | 0.0 | 1.2 | 1.2 | 1.1 | 0.8 | 31 |
| 801286 | 0.0 | 1.1 | 1.2 | 1.0 | 1.1 | 32 |
| 801287 | 0.0 | 1.3 | 1.2 | 1.1 | 1.4 | 33 |
| 801288 | 0.0 | 1.3 | 1.3 | 1.1 | 0.9 | 34 |
| 801289 | 7.0 | N.D. | N.D. | N.D. | N.D. | 35 |
| 801290 | 3.5 | 1.2* | 1.3* | 1.0* | 1.1* | 30 |
| 801291 | 0.0 | 2.2 | 2.2 | 1.5 | 1.1 | 31 |
| 801292 | 0.0 | 1.3 | 1.3 | 1.2 | 0.9 | 32 |
| 801293 | 0.0 | 1.6 | 1.6 | 1.3 | 1.5 | 33 |
| 801294 | 0.0 | 1.2 | 1.2 | 1.0 | 1.1 | 34 |
| 801295 | 1.8 | 1.4* | 1.4* | 1.0* | 0.9* | 35 |
| 801296 | 7.0 | N.D. | N.D. | N.D. | N.D. | 36 |
| 801297 | 3.5 | 1.0* | 1.0* | 0.9* | 0.8* | 37 |
| 801307 | 5.3 | 1.2* | 0.9* | 1.1* | 0.8* | 41 |
| 801308 | 5.3 | 1.2* | 1.2* | 0.9* | 1.1* | 42 |
| 801309 | 7.0 | N.D. | N.D. | N.D. | N.D. | 43 |
| 801310 | 1.8 | 1.2* | 1.2* | 1.0* | 1.0* | 44 |
| 801311 | 7.0 | N.D. | N.D. | N.D. | N.D. | 41 |
| 801312 | 0.0 | 2.0 | 1.3 | 1.0 | 1.4 | 42 |
| 801313 | 3.5 | 1.7* | 1.1* | 0.9* | 0.9* | 43 |
| 801314 | 0.0 | 1.9 | 1.2 | 1.0 | 2.9 | 44 |
| 801315 | 1.8 | 1.4* | 1.3* | 1.0* | 1.1* | 36 |
| 801316 | 0.0 | 1.5 | 1.4 | 1.0 | 1.2 | 37 |
| 801298 | 3.5 | 1.4* | 1.0* | 1.1* | 1.3* | 38 |
| 801299 | 5.3 | 1.2* | 1.2* | 1.0* | 1.0* | 39 |
| 801300 | 3.5 | 1.2* | 1.1* | 0.9* | 1.0* | 40 |
| 801301 | 7.0 | N.D. | N.D. | N.D. | N.D. | 38 |
| 801302 | 5.3 | 1.0* | 1.1* | 0.8* | 0.8* | 39 |
| 801303 | 1.8 | 1.1* | 1.0* | 1.0* | 1.1* | 40 |
| 801304 | 4.8 | 14.3* | 5.4* | 2.2* | 3.5* | 38 |
| 801305 | 5.3 | 3.6* | 1.7* | 1.6* | 1.6* | 39 |
| 801306 | 0.0 | 4.7 | 1.8 | 1.8 | 1.8 | 40 |
| 806673 | 0.0 | 1.1 | 1.0 | 1.0 | 9.1 | 49 |
| 806674 | 0.0 | 1.0 | 1.0 | 0.8 | 8.2 | 50 |
| 806675 | 0.0 | 1.0 | 1.0 | 0.8 | 10.3 | 51 |
| 806676 | 0.0 | 1.0 | 1.0 | 0.8 | 1.5 | 49 |
| 806677 | 0.0 | 0.9 | 1.0 | 0.9 | 1.5 | 50 |
| 806678 | 0.0 | 1.0 | 0.9 | 1.1 | 1.2 | 51 |
| 806679 | 0.0 | 1.2 | 1.1 | 1.1 | 1.3 | 49 |
| 806680 | 0.0 | 1.0 | 1.1 | 0.8 | 1.0 | 50 |
| 806681 | 0.0 | 1.0 | 1.0 | 0.9 | 1.4 | 51 |
| 806682 | 1.8 | 1.4* | 1.2* | 1.0* | 1.2* | 49 |
| 806683 | 0.0 | 1.2 | 1.2 | 0.9 | 1.2 | 50 |
| 806684 | 0.0 | 1.2 | 1.1 | 0.9 | 2.0 | 51 |
| 806685 | 0.0 | 1.0 | 0.9 | 0.8 | 1.5 | 52 |
| 806686 | 0.0 | 0.9 | 0.9 | 0.8 | 1.1 | 53 |
| 806687 | 0.0 | 1.0 | 1.0 | 0.8 | 1.0 | 54 |
| 806688 | 1.8 | 1.1* | 1.0* | 0.8* | 1.8* | 55 |
| 806689 | 0.0 | 1.1 | 1.0 | 0.8 | 1.3 | 52 |
| 806690 | 0.0 | 1.0 | 1.1 | 0.9 | 1.1 | 53 |
| 806691 | 5.3 | N.D. | N.D. | N.D. | N.D. | 54 |

TABLE 15-continued

| Tolerabilty of antisense oligonucleotides targeting C9Orf72 in mice | | | | | | |
|---|---|---|---|---|---|---|
| ISIS No. | Score 8 weeks after injection | AIF1 (spinal cord) | AIF1 (cere-bellum) | GFAP (spinal cord) | GFAP (cortex) | SEQ ID NO. |
| 802459 | 0.0 | 0.9 | 0.9 | 0.9 | 1.2 | 21 |
| 802460 | 5.3 | 1.1* | 1.1* | 1.0* | 1.4* | 45 |
| 802461 | 3.5 | 1.4* | 1.4* | 0.9* | 0.9* | 46 |
| 802462 | 3.5 | 0.8* | 0.9* | 0.9* | 1.1* | 21 |
| 802463 | 7.0 | N.D. | N.D. | N.D. | N.D. | 45 |
| 802464 | 1.8 | 1.4* | 1.2* | 1.5* | 1.4* | 46 |
| 802465 | 0.0 | 0.9 | 1.1 | 1.1 | 1.6 | 21 |
| 802466 | 1.8 | 1.0* | 1.0* | 1.0* | 1.4* | 45 |
| 802467 | 1.3 | 4.9 | 2.4 | 2.7 | 2.8 | 46 |
| 802468 | 0.0 | 1.4 | 1.3 | 1.2 | 2.2 | 21 |
| 802469 | 0.0 | 1.0 | 1.0 | 1.0 | 1.2 | 45 |
| 802470 | 1.5 | 3.2 | 3.4 | 2.6 | 3.4 | 46 |
| 802471 | 0.0 | 0.9 | 0.9 | 0.9 | 1.2 | 47 |
| 802472 | 3.5 | 1.6* | 1.4* | 0.9* | 1.5* | 48 |
| 802473 | 0.0 | 1.0 | 0.9 | 0.9 | 1.3 | 47 |
| 802474 | 1.8 | 1.3* | 1.2* | 1.0* | 1.8* | 48 |
| 802475 | 7.0 | N.D. | N.D. | N.D. | N.D. | 47 |
| 802476 | 1.8 | 1* | 1.2* | 0.8* | 1.8* | 48 |
| 802477 | 0.0 | 1.9 | 1.7 | 1.3 | 2.1 | 47 |
| 802478 | 3.5 | 1.4* | 1.1* | 1.1* | 1.3* | 48 |

Example 13: Tolerability of Antisense Oligonucleotides Targeting Human $C_9$Orf72 in Rats Sprague Dawley rats were separated into groups of 4 or 6 rats. Each rat in each group of rats was administered a single 3 mg intrathecal (IT) dose of the oligonucleotide indicated in the table below. At 3 hours and at 8 weeks following the IT dose, the movement of 7 different parts of the body was evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; (7) the rat's head. For each of the 7 different body parts, each rat was given a sub-score of 0 if the body part was moving or 1 if the body part was paralyzed. After each of the 7 body parts were evaluated, the sub-scores were summed for each rat and then averaged for each group. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Saline treated rats generally receive a score of 0. A score of at the top end of the range would be suggestive of acute toxicity. Results are presented in the table below as the average score for each treatment group.

Animals were sacrificed at 8 weeks. The cortex and spinal cord were collected from each animal, and RT-PCR was performed. Expression levels of AIF1were determined as a measure of inflammation. Expression levels of (GFAP) were also determined as a measure of glial cell activation. An asterisk indicates that the corresponding result is the average of 2-3 mice. Results were normalized to Gapdh and are presented relative to PBS control (1.0) in the table below.

TABLE 16

| Tolerability of antisense oligonucleotides targeting C9Orf72 in rats | | | | | | | |
|---|---|---|---|---|---|---|---|
| ISIS No. | Score 3 hours after injection | Score 8 weeks after injection | AIF1 (spinal cord) | AIF1 (cortex) | GFAP (spinal cord) | GFAP (cortex) | SEQ ID NO. |
| 801287 | 2.5 | 0.0 | 1.9 | 1.2 | 1.3 | 1.3 | 33 |
| 801288 | 4.0 | 3.5 | 1.3* | 1.3* | 1.2* | 1.3* | 34 |
| 806676 | 2.0 | 1.8 | 1.6* | 1.5* | 1.3* | 2.5* | 49 |
| 806679 | 1.2 | 0.0 | 1.4 | 1.3 | 1.3 | 1.8 | 49 |
| 806680 | 2.0 | 0.3 | 1.4 | 1.4 | 1.3 | 1.3 | 50 |
| 806690 | 1.3 | 0.0 | 1.5 | 1.4 | 1.3 | 2.0 | 53 |
| 802459 | 2.0 | 0.0 | 1.4 | 1.2 | 1.5 | 1.5 | 21 |
| 802473 | 2.0 | 2.3 | 1.8* | 1.6* | 1.7* | 1.6* | 47 |

Example 14: Tolerability of Antisense Oligonucleotides Targeting Human C9ORF72 in Non-Human Primates Female cynomolgus monkeys (2-6 kg) were given 3 doses of 35 mg of antisense oligonucleotide on days 1, 14, and 28 via intrathecal bolus injection (1 mL slow bolus followed by 0.25 mL flush). Each treatment group contained four monkeys. Two weeks after the final dose, animals were sacrificed and RT-PCR was performed on various CNS tissues. Expression levels of AIF1 were determined as a measure of inflammation and expression levels of GFAP were determined as a measure of glial cell activation. Results were normalized to GADPH and are presented relative to PBS control (1.0) in the table below for ISIS No. 801287, 802459, and 806679.

TABLE 17

| Tolerability of antisense oligonucleotides targeting C9ORF72 in cynomolgus monkeys | | | | | | |
|---|---|---|---|---|---|---|
| | AIF1 | | | GFAP | | |
| Brain Region | 801287 | 802459 | 806679 | 801287 | 802459 | 806679 |
| Cervical spinal cord | 1.0 | 0.9 | 0.9 | 1.1 | 1.0 | 1.1 |
| Thoracic spinal cord | 1.1 | 0.9 | 0.9 | 1.2 | 1.2 | 1.2 |
| Temporal cortex | 1.0 | 1.0 | 1.5 | 1.2 | 1.1 | 1.7 |
| Motor cortex | 1.0 | 1.0 | 1.2 | 1.2 | 0.7 | 1.3 |
| Lumbar spinal cord | 1.2 | 0.9 | 0.9 | 1.3 | 0.9 | 1.1 |
| Hippocampus | 1.0 | 1.0 | 1.3 | 1.9 | 1.9 | 1.7 |
| Frontal cortex | 1.3 | 0.9 | 1.3 | 1.0 | 0.7 | 1.3 |

What is claimed is:

1. A compound comprising a modified oligonucleotide, wherein the modified oligonucleotide is a gapmer consisting of a 5' wing segment, a central gap segment, and a 3' wing segment, wherein:

the 5' wing segment consists of five 2'—O—methoxyethyl nucleosides, the central gap segment consists of eight β-D-deoxyribonucleosides, and the 3' wing segment consists of five 2'—O—methoxyethyl nucleosides;

wherein the modified oligonucleotide has the nucleobase sequence 5'-GCCCCTAGCGCGCGACTC-3' (SEQ ID NO: 33), wherein each cytosine is a 5-methylcytosine; and wherein each internucleoside linkage of the modified oligonucleotide is a phosphorothioate linkage or a phosphodiester linkage.

2. The compound of claim 1, comprising the modified oligonucleotide covalently linked to a conjugate group.

3. A pharmaceutical composition consisting essentially of the compound of claim 1 and a pharmaceutically acceptable diluent or carrier.

4. The pharmaceutical composition of claim 3, wherein the pharmaceutically acceptable diluent is phosphate-buffered saline (PBS).

5. A pharmaceutical composition comprising the compound of claim 1 and a pharmaceutically acceptable diluent or carrier.

6. The pharmaceutical composition of claim 5, wherein the pharmaceutically acceptable diluent is phosphate-buffered saline (PBS).

7. A method comprising administering to an animal the compound of claim 1.

8. The method of claim 7, wherein the administering inhibits C9ORF72.

9. The method of claim 7, wherein the administering prevents, treats, ameliorates, or slows progression of a C9ORF72 associated disease.

10. The method of claim 9, wherein the C9ORF72 associated disease is any of amyotrophic lateral sclerosis (ALS), frontotemporal dementia (FTD), corticobasal degeneration syndrome (CBD), atypical Parkinsonian syndrome, or olivopontocerebellar degeneration (OPCD).

11. A modified oligonucleotide, which is a gapmer consisting of a 5' wing segment, a central gap segment, and a 3' wing segment, wherein:

the 5' wing segment consists of five 2'—O—methoxyethyl nucleosides, the central gap segment consists of eight β-D-deoxyribonucleosides, and the 3' wing segment consists of five 2'—O—methoxyethyl nucleosides;

wherein the modified oligonucleotide has the nucleobase sequence 5'-GCCCCTAGCGCGCGACTC-3' (SEQ ID NO: 33), wherein each cytosine is a 5-methylcytosine; and wherein each internucleoside linkage of the modified oligonucleotide are is a phosphorothioate linkage or a phosphodiester linkage.

12. A pharmaceutical composition consisting essentially of the modified oligonucleotide of claim 11 and a pharmaceutically acceptable diluent or carrier.

13. The pharmaceutical composition of claim 12, wherein the pharmaceutically acceptable diluent is phosphate-buffered saline (PBS).

14. A pharmaceutical composition comprising the modified oligonucleotide of claim 11 and a pharmaceutically acceptable diluent or carrier.

15. The pharmaceutical composition of claim 14, wherein the pharmaceutically acceptable diluent is phosphate-buffered saline (PBS).

16. A method comprising administering to an animal the modified oligonucleotide of claim 11.

17. The method of claim 16, wherein the administering inhibits C9ORF72.

18. The method of claim 16, wherein the administering prevents, treats, ameliorates, or slows progression of a C9ORF72 associated disease.

19. The method of claim 18, wherein the C9ORF72 associated disease is any of amyotrophic lateral sclerosis (ALS), frontotemporal dementia (FTD), corticobasal degeneration syndrome (CBD), atypical Parkinsonian syndrome, or olivopontocerebellar degeneration (OPCD).

* * * * *

SEQUENCE LISTING

```
<160> NUMBER OF SEQ ID NOS: 60

<210> SEQ ID NO 1
<211> LENGTH: 3339
<212> TYPE: DNA
<213> ORGANISM: homo sapiens

<400> SEQUENCE: 1

acgtaaccta cggtgtcccg ctaggaaaga gaggtgcgtc aaacagcgac aagttccgcc     60

cacgtaaaag atgacgcttg gtgtgtcagc cgtccctgct gcccggttgc ttctcttttg    120

ggggcggggt ctagcaagag caggtgtggg tttaggagat atctccggag catttggata    180

atgtgacagt tggaatgcag tgatgtcgac tctttgccca ccgccatctc cagctgttgc    240

caagacagag attgctttaa gtggcaaatc acctttatta gcagctactt ttgcttactg    300

ggacaatatt cttggtccta gagtaaggca catttgggct ccaaagacag aacaggtact    360

tctcagtgat ggagaaataa cttttcttgc caaccacact ctaaatggag aaatccttcg    420

aaatgcagag agtggtgcta tagatgtaaa gtttttttgtc ttgtctgaaa agggagtgat    480

tattgtttca ttaatctttg atggaaactg gaatggggat cgcagcacat atggactatc    540

aattatactt ccacagacag aacttagttt ctacctccca cttcatagag tgtgtgttga    600

tagattaaca catataatcc ggaaaggaag aatatggatg cataaggaaa gacaagaaaa    660

tgtccagaag attatcttag aaggcacaga gagaatggaa gatcagggtc agagtattat    720

tccaatgctt actggagaag tgattcctgt aatggaactg ctttcatcta tgaaatcaca    780

cagtgttcct gaagaaatag atatagctga tacagtactc aatgatgatg atattggtga    840

cagctgtcat gaaggctttc ttctcaatgc catcagctca cacttgcaaa cctgtggctg    900

ttccgttgta gtaggtagca gtgcagagaa agtaaataag atagtcagaa cattatgcct    960

ttttctgact ccagcagaga gaaaatgctc caggttatgt gaagcagaat catcatttaa   1020

atatgagtca gggctctttg tacaaggcct gctaaaggat tcaactggaa gctttgtgct   1080

gcctttccgg caagtcatgt atgctccata tcccaccaca cacatagatg tggatgtcaa   1140
```

```
tactgtgaag cagatgccac cctgtcatga acatatttat aatcagcgta gatacatgag   1200
atccgagctg acagccttct ggagagccac ttcagaagaa gacatggctc aggatacgat   1260
catctacact gacgaaagct ttactcctga tttgaatatt tttcaagatg tcttacacag   1320
agacactcta gtgaaagcct tcctggatca ggtctttcag ctgaaacctg gcttatctct   1380
cagaagtact ttccttgcac agtttctact tgtccttcac agaaaagcct tgacactaat   1440
aaaatatata gaagacgata cgcagaaggg aaaaaagccc tttaaatctc ttcggaacct   1500
gaagatagac cttgatttaa cagcagaggg cgatcttaac ataataatgg ctctggctga   1560
gaaaattaaa ccaggcctac actcttttat ctttggaaga cctttctaca ctagtgtgca   1620
agaacgagat gttctaatga ctttttaaat gtgtaactta ataagcctat tccatcacaa   1680
tcatgatcgc tggtaaagta gctcagtggt gtggggaaac gttcccctgg atcatactcc   1740
agaattctgc tctcagcaat tgcagttaag taagttacac tacagttctc acaagagcct   1800
gtgaggggat gtcaggtgca tcattacatt gggtgtctct tttcctagat ttatgctttt   1860
gggatacaga cctatgttta caatataata aatattattg ctatctttta aagatataat   1920
aataggatgt aaacttgacc acaactactg ttttttgaa atacatgatt catggtttac   1980
atgtgtcaag gtgaaatctg agttggcttt tacagatagt tgactttcta tcttttggca   2040
ttctttggtg tgtagaatta ctgtaatact tctgcaatca actgaaaact agagccttta   2100
aatgatttca attccacaga aagaaagtga gcttgaacat aggatgagct ttagaaagaa   2160
aattgatcaa gcagatgttt aattggaatt gattattaga tcctactttg tggatttagt   2220
ccctgggatt cagtctgtag aaatgtctaa tagttctcta tagtccttgt tcctggtgaa   2280
ccacagttag ggtgttttgt ttattttatt gttcttgcta ttgttgatat tctatgtagt   2340
tgagctctgt aaaaggaaat tgtattttat gttttagtaa ttgttgccaa ctttttaaat   2400
taattttcat tatttttgag ccaaattgaa atgtgcacct cctgtgcctt ttttctcctt   2460
agaaaatcta attacttgga acaagttcag atttcactgg tcagtcattt tcatcttgtt   2520
ttcttcttgc taagtcttac catgtacctg ctttggcaat cattgcaact ctgagattat   2580
aaaatgcctt agagaatata ctaactaata agatcttttt ttcagaaaca gaaaatagtt   2640
ccttgagtac ttccttcttg catttctgcc tatgtttttg aagttgttgc tgtttgcctg   2700
caataggcta taaggaatag caggagaaat tttactgaag tgctgttttc ctaggtgcta   2760
ctttggcaga gctaagttat cttttgtttt cttaatgcgt ttggaccatt ttgctggcta   2820
taaaataact gattaatata attctaacac aatgttgaca ttgtagttac acaaacacaa   2880
ataaatattt tatttaaaat tctggaagta atataaaagg gaaaatatat ttataagaaa   2940
gggataaagg taatagagcc cttctgcccc ccacccacca aatttacaca acaaaatgac   3000
atgttcgaat gtgaaaggtc ataatagctt tcccatcatg aatcagaaag atgtggacag   3060
cttgatgttt tagacaacca ctgaactaga tgactgttgt actgtagctc agtcatttaa   3120
aaaatatata aatactacct tgtagtgtcc catactgtgt tttttacatg gtagattctt   3180
atttaagtgc taactggtta ttttctttgg ctggtttatt gtactgttat acagaatgta   3240
agttgtacag tgaaataagt tattaaagca tgtgtaaaca ttgttatata tcttttctcc   3300
taaatggaga attttgaata aaatatattt gaaattttg                          3339
```

<210> SEQ ID NO 2
<211> LENGTH: 30001
<212> TYPE: DNA

<213> ORGANISM: homo sapiens

<400> SEQUENCE: 2

```
caaagaaaag ggggaggttt tgttaaaaaa gagaaatgtt acatagtgct ctttgagaaa     60
attcattggc actattaagg atctgaggag ctggtgagtt tcaactggtg agtgatggtg    120
gtagataaaa ttagagctgc agcaggtcat tttagcaact attagataaa actggtctca    180
ggtcacaacg ggcagttgca gcagctggac ttggagagaa ttacactgtg ggagcagtgt    240
catttgtcct aagtgctttt ctacccccta cccccactat tttagttggg tataaaaaga    300
atgacccaat ttgtatgatc aactttcaca aagcatagaa cagtaggaaa agggtctgtt    360
tctgcagaag gtgtagacgt tgagagccat tttgtgtatt tattcctccc tttcttcctc    420
ggtgaatgat taaaacgttc tgtgtgattt ttagtgatga aaaagattaa atgctactca    480
ctgtagtaag tgccatctca cacttgcaga tcaaaaggca cacagtttaa aaaacctttg    540
tttttttaca catctgagtg gtgtaaatgc tactcatctg tagtaagtgg aatctataca    600
cctgcagacc aaaagacgca aggtttcaaa aatctttgtg ttttttacac atcaaacaga    660
atggtacgtt tttcaaaagt taaaaaaaaa caactcatcc acatattgca actagcaaaa    720
atgacattcc ccagtgtgaa aatcatgctt gagagaattc ttacatgtaa aggcaaaatt    780
gcgatgactt tgcaggggac cgtgggattc ccgcccgcag tgccggagct gtcccctacc    840
agggtttgca gtggagtttt gaatgcactt aacagtgtct tacggtaaaa acaaaatttc    900
atccaccaat tatgtgttga gcgcccactg cctaccaagc acaaacaaaa ccattcaaaa    960
ccacgaaatc gtcttcactt tctccagatc cagcagcctc ccctattaag gttcgcacac   1020
gctattgcgc caacgctcct ccagagcggg tcttaagata aaagaacagg acaagttgcc   1080
ccgccccatt tcgctagcct cgtgagaaaa cgtcatcgca catagaaaac agacagacgt   1140
aacctacggt gtcccgctag gaaagagagg tgcgtcaaac agcgacaagt tccgcccacg   1200
taaaagatga cgcttggtgt gtcagccgtc cctgctgccc ggttgcttct cttttggggg   1260
cggggtctag caagagcagg tgtgggttta ggaggtgtgt gtttttgttt ttcccaccct   1320
ctctccccac tacttgctct cacagtactc gctgagggtg aacaagaaaa gacctgataa   1380
agattaacca gaagaaaaca aggagggaaa caaccgcagc ctgtagcaag ctctggaact   1440
caggagtcgc gcgctagggg ccggggccgg ggccggggcg tggtcggggc gggcccgggg   1500
gcgggcccgg ggcggggctg cggttgcggt gcctgcgccc gcggcggcgg aggcgcaggc   1560
ggtggcgagt gggtgagtga ggaggcggca tcctggcggg tggctgtttg gggttcggct   1620
gccgggaaga ggcgcgggta gaagcggggg ctctcctcag agctcgacgc atttttactt   1680
tccctctcat ttctctgacc gaagctgggt gtcgggcttt cgcctctagc gactggtgga   1740
attgcctgca tccgggcccc gggcttcccg gcggcggcgg cggcggcggc ggcgcaggga   1800
caagggatgg ggatctggcc tcttccttgc tttcccgccc tcagtacccg agctgtctcc   1860
ttcccgggga cccgctggga gcgctgccgc tgcgggctcg agaaaaggga gcctcgggta   1920
ctgagaggcc tcgcctgggg gaaggccgga gggtgggcgg cgcgcggctt ctgcggacca   1980
agtcggggtt cgctaggaac ccgagacggt ccctgccggc gaggagatca tgcgggatga   2040
gatgggggtg tggagacgcc tgcacaattt cagcccaagc ttctagagag tggtgatgac   2100
ttgcatatga gggcagcaat gcaagtcggt gtgctcccca ttctgtggga catgacctgg   2160
ttgcttcaca gctccgagat gacacagact tgcttaaagg aagtgactat tgtgacttgg   2220
gcatcacttg actgatggta atcagttgtc taaagaagtg cacagattac atgtccgtgt   2280
```

```
gctcattggg tctatctggc cgcgttgaac accaccaggc tttgtattca gaaacaggag   2340
ggaggtcctg cactttccca ggaggggtgg ccctttcaga tgcaatcgag attgttaggc   2400
tctgggagag tagttgcctg gttgtggcag ttggtaaatt tctattcaaa cagttgccat   2460
gcaccagttg ttcacaacaa gggtacgtaa tctgtctggc attacttcta cttttgtaca   2520
aaggatcaaa aaaaaaaaag atactgttaa gatatgattt ttctcagact ttgggaaact   2580
tttaacataa tctgtgaata tcacagaaac aagactatca tataggggat attaataacc   2640
tggagtcaga atacttgaaa tacggtgtca tttgacacgg gcattgttgt caccacctct   2700
gccaaggcct gccactttag gaaaaccctg aatcagttgg aaactgctac atgctgatag   2760
tacatctgaa acaagaacga gagtaattac cacattccag attgttcact aagccagcat   2820
ttacctgctc caggaaaaaa ttacaagcac cttatgaagt tgataaaata ttttgtttgg   2880
ctatgttggc actccacaat ttgctttcag agaaacaaag taaaccaagg aggacttctg   2940
tttttcaagt ctgccctcgg gttctattct acgttaatta gatagttccc aggaggacta   3000
ggttagccta cctattgtct gagaaacttg gaactgtgag aaatggccag atagtgatat   3060
gaacttcacc ttccagtctt ccctgatgtt gaagattgag aaagtgttgt gaactttctg   3120
gtactgtaaa cagttcactg tccttgaagt ggtcctgggc agctcctgtt gtggaaagtg   3180
gacggtttag gatcctgctt ctctttgggc tgggagaaaa taaacagcat ggttacaagt   3240
attgagagcc aggttggaga aggtggctta cacctgtaat gccagagctt tgggaggcgg   3300
aggcaagagg atcacttgaa gccaggagtt caagctcaac ctgggcaacg tagaccctgt   3360
ctctacaaaa aattaaaaac ttagccgggc gtggtgatgt gcacctgtag tcctagctac   3420
ttgggaggct gaggcaggag ggtcatttga gcccaagagt ttgaagttac cgagagctat   3480
gatcctgcca gtgcattcca gcctggatga caaaacgaga ccctgtctct aaaaaacaag   3540
aagtgagggc tttatgattg tagaattttc actacaatag cagtggacca accacctttc   3600
taaataccaa tcagggaaga gatggttgat tttttaacag acgtttaaag aaaaagcaaa   3660
acctcaaact tagcactcta ctaacagttt tagcagatgt taattaatgt aatcatgtct   3720
gcatgtatgg gattatttcc agaaagtgta ttgggaaacc tctcatgaac cctgtgagca   3780
agccaccgtc tcactcaatt tgaatcttgg cttccctcaa aagactggct aatgtttggt   3840
aactctctgg agtagacagc actacatgta cgtaagatag gtacataaac aactattggt   3900
tttgagctga ttttttttcag ctgcatttgc atgtatggat tttctcacc aaagacgatg   3960
acttcaagta ttagtaaaat aattgtacag ctctcctgat tatacttctc tgtgacattt   4020
catttcccag gctatttctt ttggtaggat ttaaaactaa gcaattcagt atgatctttg   4080
tccttcattt tctttcttat tctttttgtt tgtttgtttg tttgtttttt tcttgaggca   4140
gagtctctct ctgtcgccca ggctggagtg cagtggcgcc atctcagctc attgcaacct   4200
ctgccacctc cgggttcaag agattctcct gcctcagcct cccgagtagc tgggattaca   4260
ggtgtccacc accacacccg gctaattttt tgtattttta gtagaggtgg ggtttcacca   4320
tgttggccag gctggtcttg agctcctgac ctcaggtgat ccacctgcct cggcctacca   4380
aagagctggg ataacaggtg tgacccacca tgcccggccc attttttttt tcttattctg   4440
ttaggagtga gagtgtaact agcagtataa tagttcaatt ttcacaacgt ggtaaaagtt   4500
tccctataat tcaatcagat tttgctccag ggttcagttc tgttttagga aatactttta   4560
ttttcagttt aatgatgaaa tattagagtt gtaatattgc ctttatgatt atccaccttt   4620
```

-continued

```
ttaacctaaa agaatgaaag aaaaatatgt ttgcaatata attttatggt tgtatgttaa   4680
cttaattcat tatgttggcc tccagtttgc tgttgttagt tatgacagca gtagtgtcat   4740
taccatttca attcagatta cattcctata tttgatcatt gtaaactgac tgcttacatt   4800
gtattaaaaa cagtggatat tttaaagaag ctgtacggct tatatctagt gctgtctctt   4860
aagactatta aattgataca acatatttaa aagtaaatat tacctaaatg aatttttgaa   4920
attacaaata cacgtgttaa aactgtcgtt gtgttcaacc atttctgtac atacttagag   4980
ttaactgttt tgccaggctc tgtatgccta ctcataatat gataaaagca ctcatctaat   5040
gctctgtaaa tagaagtcag tgctttccat cagactgaac tctcttgaca agatgtggat   5100
gaaattcttt aagtaaaatt gtttactttg tcatacattt acagatcaaa tgttagctcc   5160
caaagcaatc atatggcaaa gataggtata tcatagtttg cctattagct gctttgtatt   5220
gctattatta taaatagact tcacagtttt agacttgctt aggtgaaatt gcaattcttt   5280
ttactttcag tcttagataa caagtcttca attatagtac aatcacacat tgcttaggaa   5340
tgcatcatta ggcgattttg tcattatgca aacatcatag agtgtactta cacaaaccta   5400
gatagtatag cctttatgta cctaggccgt atggtatagt ctgttgctcc taggccacaa   5460
acctgtacaa ctgttactgt actgaatact atagacagtt gtaacacagt ggtaaatatt   5520
tatctaaata tatgcaaaca gagaaaaggt acagtaaaag tatggtataa aagataatgg   5580
tatacctgtg taggccactt accacgaatg gagcttgcag gactagaagt tgctctgggt   5640
gagtcagtga gtgagtggtg aattaatgtg aaggcctaga acactgtaca ccactgtaga   5700
ctataaacac agtacgctga agctacacca aatttatctt aacagttttt cttcaataaa   5760
aaattataac tttttaactt tgtaaacttt ttaatttttt aacttttaaa atacttagct   5820
tgaaacacaa atacattgta tagctataca aaaatatttt ttctttgtat ccttattcta   5880
gaagcttttt tctattttct attttaaatt ttttttttta cttgttagtc gtttttgtta   5940
aaaactaaaa cacacacact ttcacctagg catagacagg attaggatca tcagtatcac   6000
tcccttccac ctcactgcct tccacctcca catcttgtcc cactggaagg tttttagggg   6060
caataacaca catgtagctg tcacctatga taacagtgct ttctgttgaa tacctcctga   6120
aggacttgcc tgaggctgtt ttacatttaa cttaaaaaaa aaaaaagtag aaggagtgca   6180
ctctaaaata acaataaaag gcatagtata gtgaatacat aaaccagcaa tgtagtagtt   6240
tattatcaag tgttgtacac tgtaataatt gtatgtgcta tactttaaat aacttgcaaa   6300
atagtactaa gaccttatga tggttacagt gtcactaagg caatagcata ttttcaggtc   6360
cattgtaatc taatgggact accatcatat atgcagtcta ccattgactg aaacgttaca   6420
tggcacataa ctgtatttgc aagaatgatt tgttttacat taatatcaca taggatgtac   6480
ctttttagag tggtatgttt atgtggatta agatgtacaa gttgagcaag gggaccaaga   6540
gccctgggtt ctgtcttgga tgtgagcgtt tatgttcttc tcctcatgtc tgttttctca   6600
ttaaattcaa aggcttgaac gggccctatt tagcccttct gttttctacg tgttctaaat   6660
aactaaagct tttaaattct agccatttag tgtagaactc tctttgcagt gatgaaatgc   6720
tgtattggtt tcttggctag catattaaat atttttatct ttgtcttgat acttcaatgt   6780
cgttttaaac atcaggatcg ggcttcagta ttctcataac cagagagttc actgaggata   6840
caggactgtt tgcccatttt ttgttatggc tccagacttg tggtatttcc atgtcttttt   6900
tttttttttt ttttttgacc ttttagcggc tttaaagtat ttctgttgtt aggtgttgta   6960
ttacttttct aagattactt aacaaagcac cacaaactga gtggctttaa acaacagcaa   7020
```

```
tttattctct cacaattcta gaagctagaa gtccgaaatc aaagtgttga caggggcatg 7080
atcttcaaga gagaagactc tttccttgcc tcttcctggc ttctggtggt taccagcaat 7140
cctgagtgtt cctttcttgc cttgtagttt caacaatcca gtatctgcct tttgtcttca 7200
catggctgtc taccatttgt ctctgtgtct ccaaatctct ctccttataa acacagcagt 7260
tattggatta ggccccactc taatccagta tgaccccatt ttaacatgat tacacttatt 7320
tctagataag gtcacattca cgtacaccaa gggttaggaa ttgaacatat ctttttgggg 7380
gacacaattc aacccacaag tgtcagtctc tagctgagcc tttcccttcc tgtttttctc 7440
ctttttagtt gctatgggtt aggggccaaa tctccagtca tactagaatt gcacatggac 7500
tggatatttg ggaatactgc gggtctattc tatgagcttt agtatgtaac atttaatatc 7560
agtgtaaaga agcccttttt taagttattt ctttgaattt ctaaatgtat gccctgaata 7620
taagtaacaa gttaccatgt cttgtaaaat gatcatatca acaaacattt aatgtgcacc 7680
tactgtgcta gttgaatgtc tttatcctga taggagataa caggattcca catctttgac 7740
ttaagaggac aaaccaaata tgtctaaatc atttggggtt ttgatggata tctttaaatt 7800
gctgaaccta atcattggtt tcatatgtca ttgtttagat atctccggag catttggata 7860
atgtgacagt tggaatgcag tgatgtcgac tctttgccca ccgccatctc cagctgttgc 7920
caagacagag attgctttaa gtggcaaatc acctttatta gcagctactt ttgcttactg 7980
ggacaatatt cttggtccta gagtaaggca catttgggct ccaaagacag aacaggtact 8040
tctcagtgat ggagaaataa cttttcttgc caaccacact ctaaatggag aaatccttcg 8100
aaatgcagag agtggtgcta tagatgtaaa gttttttgtc ttgtctgaaa agggagtgat 8160
tattgtttca ttaatctttg atggaaactg gaatggggat cgcagcacat atggactatc 8220
aattatactt ccacagacag aacttagttt ctacctccca cttcatagag tgtgtgttga 8280
tagattaaca catataatcc ggaaaggaag aatatggatg cataaggtaa gtgatttttc 8340
agcttattaa tcatgttaac ctatctgttg aaagcttatt ttctggtaca tataaatctt 8400
attttttaa ttatatgcag tgaacatcaa acaataaatg ttatttattt tgcatttacc 8460
ctattagata caaatacatc tggtctgata cctgtcatct tcatattaac tgtggaaggt 8520
acgaaatggt agctccacat tatagatgaa aagctaaagc ttagacaaat aaagaaactt 8580
ttagaccctg gattcttctt gggagccttt gactctaata ccttttgttt ccctttcatt 8640
gcacaattct gtcttttgct tactactatg tgtaagtata acagttcaaa gtaatagttt 8700
cataagctgt tggtcatgta gcctttggtc tctttaacct ctttgccaag ttcccaggtt 8760
cataaaatga ggaggttgaa tggaatggtt cccaagagaa ttccttttaa tcttacagaa 8820
attattgttt tcctaaatcc tgtagttgaa tatataatgc tatttacatt tcagtatagt 8880
tttgatgtat ctaaagaaca cattgaattc tccttcctgt gttccagttt gatactaacc 8940
tgaaagtcca ttaagcatta ccagttttaa aaggcttttg cccaatagta aggaaaaata 9000
atatctttta aaagaataat tttttactat gtttgcaggc ttacttcctt ttttctcaca 9060
ttatgaaact cttaaaatca ggagaatctt ttaaacaaca tcataatgtt taatttgaaa 9120
agtgcaagtc attcttttcc tttttgaaac tatgcagatg ttacattgac tgttttctgt 9180
gaagttatct ttttttcact gcagaataaa ggttgttttg attttatttt gtattgttta 9240
tgagaacatg catttgttgg gttaatttcc tacccctgcc cccatttttt ccctaaagta 9300
gaaagtattt ttcttgtgaa ctaaattact acacaagaac atgtctattg aaaaataagc 9360
```

-continued

```
aagtatcaaa atgttgtggg ttgttttttt aaataaattt tctcttgctc aggaaagaca   9420
agaaaatgtc cagaagatta tcttagaagg cacagagaga atggaagatc aggtatatgc   9480
aaattgcata ctgtcaaatg tttttctcac agcatgtatc tgtataaggt tgatggctac   9540
atttgtcaag gccttggaga catacgaata agcctttaat ggagctttta tggaggtgta   9600
cagaataaac tggaggaaga tttccatatc ttaaacccaa agagttaaat cagtaaacaa   9660
aggaaaatag taattgcatc tacaaattaa tatttgctcc cttttttttt ctgtttgccc   9720
agaataaatt ttggataact tgttcatagt aaaaataaaa aaaattgtct ctgatatgtt   9780
ctttaaggta ctacttctcg aacctttccc tagaagtagc tgtaacagaa ggagagcata   9840
tgtacccctg aggtatctgt ctggggtgta ggcccaggtc cacacaatat ttcttctaag   9900
tcttatgttg tatcgttaag actcatgcaa tttacatttt attccataac tattttagta   9960
ttaaaatttg tcagtgatat ttcttaccct ctcctctagg aaaatgtgcc atgtttatcc  10020
cttggctttg aatgcccctc aggaacagac actaagagtt tgagaagcat ggttacaagg  10080
gtgtggcttc ccctgcggaa actaagtaca gactatttca ctgtaaagca gagaagttct  10140
tttgaaggag aatctccagt gaagaaagag ttcttcactt ttacttccat ttcctcttgt  10200
gggtgaccct caatgctcct tgtaaaactc caatatttta aacatggctg ttttgccttt  10260
ctttgcttct ttttagcatg aatgagacag atgatacttt aaaaaagtaa ttaaaaaaaa  10320
aaacttgtga aaatacatgg ccataataca gaacccaata caatgatctc ctttaccaaa  10380
ttgttatgtt tgtacttttg tagatagctt tccaattcag agacagttat tctgtgtaaa  10440
ggtctgactt aacaagaaaa gatttccctt tacccaaaga atcccagtcc ttatttgctg  10500
gtcaataagc agggtcccca ggaatggggt aactttcagc accctctaac ccactagtta  10560
ttagtagact aattaagtaa acttatcgca agttgaggaa acttagaacc aactaaaatt  10620
ctgcttttac tgggattttg ttttttcaaa ccagaaacct ttacttaagt tgactactat  10680
taatgaattt tggtctctct tttaagtgct cttcttaaaa atgttatctt actgctgaga  10740
agttcaagtt tgggaagtac aaggaggaat agaaacttaa gagattttct tttagagcct  10800
cttctgtatt tagccctgta ggattttttt tttttttttt ttttttggtg ttgttgagct  10860
tcagtgaggc tattcattca cttatactga taatgtctga gatactgtga atgaaatact  10920
atgtatgctt aaacctaaga ggaaatattt tcccaaaatt attcttcccg aaaaggagga  10980
gttgcctttt gattgagttc ttgcaaatct cacaacgact ttattttgaa caatactgtt  11040
tggggatgat gcattagttt gaaacaactt cagttgtagc tgtcatctga taaaattgct  11100
tcacagggaa ggaaatttaa cacggatcta gtcattattc ttgttagatt gaatgtgtga  11160
attgtaattg taaacaggca tgataattat tactttaaaa actaaaaaca gtgaatagtt  11220
agttgtggag gttactaaag gatggttttt ttttaaataa aactttcagc attatgcaaa  11280
tgggcatatg gcttaggata aaacttccag aagtagcatc acatttaaat tctcaagcaa  11340
cttaataata tggggctctg aaaaactggt taaggttact ccaaaaatgg ccctgggtct  11400
gacaaagatt ctaacttaaa gatgcttatg aagactttga gtaaaatcat ttcataaaat  11460
aagtgaggaa aaacaactag tattaaattc atcttaaata atgtatgatt taaaaaatat  11520
gtttagctaa aaatgcatag tcatttgaca atttcattta tatctcaaaa aatttactta  11580
accaagttgg tcacaaaact gatgagactg gtggtggtag tgaataaatg agggaccatc  11640
catatttgag acactttaca tttgtgatgt gttatactga attttcagtt tgattctata  11700
gactacaaat ttcaaaatta caatttcaag atgtaataag tagtaatatc ttgaaatagc  11760
```

```
tctaaaggga atttttctgt tttattgatt cttaaaatat atgtgctgat tttgatttgc  11820
atttgggtag attatacttt tatgagtatg gaggttaggt attgattcaa gttttcctta  11880
cctatttggt aaggatttca aagtcttttt gtgcttggtt ttcctcattt ttaaatatga  11940
aatatattga tgacctttaa caaatttttt ttatctcaaa ttttaaagga gatcttttct  12000
aaaagaggca tgatgactta atcattgcat gtaacagtaa acgataaacc aatgattcca  12060
tactctctaa agaataaaag tgagctttag ggccgggcat ggtcagaaat ttgacaccaa  12120
cctggccaac atggcgaaac cccgtctcta ctaaaaatac aaaaatcagc cgggcatggt  12180
ggcggcacct atagtcccag ctacttggga ggatgagaca ggagagtcac ttgaacctgg  12240
gaggagaggt tgcagtgagc tgagatcacg ccattgcact ccagcctgag caatgaaagc  12300
aaaactccat ctcaaaaaaa aaaaaagaaa agaaagaata aaagtgagct ttggattgca  12360
tataaatcct ttagacatgt agtagacttg tttgatactg tgtttgaaca aattacgaag  12420
tattttcatc aaagaatgtt attgtttgat gttattttta ttttttattg cccagcttct  12480
ctcatattac gtgattttct tcacttcatg tcactttatt gtgcagggtc agagtattat  12540
tccaatgctt actggagaag tgattcctgt aatggaactg ctttcatcta tgaaatcaca  12600
cagtgttcct gaagaaatag atgtaagttt aaatgagagc aattatacac tttatgagtt  12660
ttttggggtt atagtattat tatgtatatt attaatattc taattttaat agtaaggact  12720
ttgtcataca tactattcac atacagtatt agccacttta gcaaataagc acacacaaaa  12780
tcctggattt tatggcaaaa cagaggcatt tttgatcagt gatgacaaaa ttaaattcat  12840
tttgtttatt tcattacttt tataattcct aaaagtggga ggatcccagc tcttatagga  12900
gcaattaata tttaatgtag tgtcttttga aacaaaactg tgtgccaaag tagtaaccat  12960
taatggaagt ttacttgtag tcacaaattt agtttcctta atcatttgtt gaggacgttt  13020
tgaatcacac actatgagtg ttaagagata cctttaggaa actattcttg ttgttttctg  13080
attttgtcat ttaggttagt ctcctgattc tgacagctca gaagaggaag ttgttcttgt  13140
aaaaattgtt taacctgctt gaccagcttt cacatttgtt cttctgaagt ttatggtagt  13200
gcacagagat tgttttttgg ggagtcttga ttctcggaaa tgaaggcagt gtgttatatt  13260
gaatccagac ttccgaaaac ttgtatatta aaagtgttat ttcaacacta tgttacagcc  13320
agactaattt ttttattttt tgatgcattt tagatagctg atacagtact caatgatgat  13380
gatattggtg acagctgtca tgaaggcttt cttctcaagt aagaattttt cttttcataa  13440
aagctggatg aagcagatac catcttatgc tcacctatga caagatttgg aagaaagaaa  13500
ataacagact gtctacttag attgttctag ggacattacg tatttgaact gttgcttaaa  13560
tttgtgttat ttttcactca ttatatttct atatatattt ggtgttattc catttgctat  13620
ttaaagaaac cgagtttcca tcccagacaa gaaatcatgg ccccttgctt gattctggtt  13680
tcttgtttta cttctcatta aagctaacag aatcctttca tattaagttg tactgtagat  13740
gaacttaagt tatttaggcg tagaacaaaa ttattcatat ttatactgat ctttttccat  13800
ccagcagtgg agtttagtac ttaagagttt gtgcccttaa accagactcc ctggattaat  13860
gctgtgtacc cgtgggcaag gtgcctgaat tctctataca cctatttcct catctgtaaa  13920
atggcaataa tagtaatagt acctaatgtg tagggttgtt ataagcattg agtaagataa  13980
ataatataaa gcacttagaa cagtgcctgg aacataaaaa cacttaataa tagctcatag  14040
ctaacatttc ctatttacat ttcttctaga aatagccagt atttgttgag tgcctacatg  14100
```

-continued

```
ttagttcctt tactagttgc tttacatgta ttatcttata ttctgtttta aagtttcttc  14160
acagttacag attttcatga aattttactt ttaataaaag agaagtaaaa gtataaagta  14220
ttcactttta tgttcacagt cttttccttt aggctcatga tggagtatca gaggcatgag  14280
tgtgtttaac ctaagagcct taatggcttg aatcagaagc actttagtcc tgtatctgtt  14340
cagtgtcagc ctttcataca tcattttaaa tcccatttga ctttaagtaa gtcacttaat  14400
ctctctacat gtcaatttct tcagctataa aatgatggta tttcaataaa taaatacatt  14460
aattaaatga tattatactg actaattggg ctgttttaag gctcaataag aaaatttctg  14520
tgaaaggtct ctagaaaatg taggttccta tacaaataaa agataacatt gtgcttatag  14580
cttcggtgtt tatcatataa agctattctg agttatttga agagctcacc tacttttttt  14640
tgtttttagt ttgttaaatt gttttatagg caatgttttt aatctgtttt ctttaactta  14700
cagtgccatc agctcacact tgcaaacctg tggctgttcc gttgtagtag gtagcagtgc  14760
agagaaagta aataaggtag tttattttat aatctagcaa atgatttgac tctttaagac  14820
tgatgatata tcatggattg tcatttaaat ggtaggttgc aattaaaatg atctagtagt  14880
ataaggaggc aatgtaatct catcaaattg ctaagacacc ttgtggcaac agtgagtttg  14940
aaataaactg agtaagaatc atttatcagt ttattttgat agctcggaaa taccagtgtc  15000
agtagtgtat aaatggtttt gagaatatat taaaatcaga tatataaaaa aaattactct  15060
tctatttccc aatgttatct ttaacaaatc tgaagatagt catgtacttt tggtagtagt  15120
tccaaagaaa tgttatttgt ttattcatct tgatttcatt gtcttcgctt tccttctaaa  15180
tctgtccctt ctagggagct attgggatta agtggtcatt gattattata ctttattcag  15240
taatgtttct gaccctttcc ttcagtgcta cttgagttaa ttaaggatta atgaacagtt  15300
acatttccaa gcattagcta ataaactaaa ggattttgca cttttcttca ctgaccatta  15360
gttagaaaga gttcagagat aagtatgtgt atctttcaat ttcagcaaac ctaatttttt  15420
aaaaaaagtt ttacatagga aatatgttgg aaatgatact ttacaaagat attcataatt  15480
ttttttgta atcagctact ttgtatattt acatgagcct taatttatat ttctcatata  15540
accatttatg agagcttagt atacctgtgt cattatattg catctacgaa ctagtgacct  15600
tattccttct gttacctcaa acaggtggct ttccatctgt gatctccaaa gccttaggtt  15660
gcacagagtg actgccgagc tgctttatga agggagaaag gctccatagt tggagtgttt  15720
ttttttttt ttttaaacat ttttcccatc ctccatcctc ttgagggaga atagcttacc  15780
ttttatcttg ttttaatttg agaaagaagt tgccaccact ctaggttgaa aaccactcct  15840
ttaacataat aactgtggat atggtttgaa tttcaagata gttacatgcc tttttatttt  15900
tcctaataga gctgtaggtc aaatattatt agaatcagat ttctaaatcc cacccaatga  15960
cctgcttatt ttaaatcaaa ttcaataatt aattctcttc tttttggagg atctggacat  16020
tctttgatat ttcttacaac gaatttcatg tgtagaccca ctaaacagaa gctataaaag  16080
ttgcatggtc aaataagtct gagaaagtct gcagatgata taattcacct gaagagtcac  16140
agtatgtagc caaatgttaa aggttttgag atgccataca gtaaatttac caagcatttt  16200
ctaaatttat ttgaccacag aatccctatt ttaagcaaca actgttacat cccatggatt  16260
ccaggtgact aaagaatact tatttcttag gatatgtttt attgataata acaattaaaa  16320
tttcagatat ctttcataag caaatcagtg gtctttttac ttcatgtttt aatgctaaaa  16380
tattttcttt tatagatagt cagaacatta tgccttttc tgactccagc agagagaaaa  16440
tgctccaggt tatgtgaagc agaatcatca tttaaatatg agtcagggct ctttgtacaa  16500
```

-continued

```
ggcctgctaa aggtatagtt tctagttatc acaagtgaaa ccacttttct aaaatcattt  16560
ttgagactct ttatagacaa atcttaaata ttagcattta atgtatctca tattgacatg  16620
cccagagact gacttccttt acacagttct gcacatagac tatatgtctt atggatttat  16680
agttagtatc atcagtgaaa caccatagaa taccctttgt gttccaggtg ggtccctgtt  16740
cctacatgtc tagcctcagg actttttttt ttttaacaca tgcttaaatc aggttgcaca  16800
tcaaaaataa gatcatttct ttttaactaa atagatttga attttattga aaaaaaattt  16860
taaacatctt taagaagctt ataggattta agcaattcct atgtatgtgt actaaaatat  16920
atatatttct atatataata tatattagaa aaaaattgta tttttctttt atttgagtct  16980
actgtcaagg agcaaaacag agaaatgtaa attagcaatt atttataata cttaaaggga  17040
agaaagttgt tcaccttgtt gaatctatta ttgttatttc aattatagtc ccaagacgtg  17100
aagaaatagc tttcctaatg gttatgtgat tgtctcatag tgactacttt cttgaggatg  17160
tagccacggc aaaatgaaat aaaaaaattt aaaaattgtt gcaaatacaa gttatattag  17220
gcttttgtgc attttcaata atgtgctgct atgaactcag aatgatagta tttaaatata  17280
gaaactagtt aaaggaaacg tagtttctat ttgagttata catatctgta aattagaact  17340
tctcctgtta aaggcataat aaagtgctta atacttttgt ttcctcagca ccctctcatt  17400
taattatata attttagttc tgaaagggac ctataccaga tgcctagagg aaatttcaaa  17460
actatgatct aatgaaaaaa tatttaatag ttctccatgc aaatacaaat catatagttt  17520
tccagaaaat acctttgaca ttatacaaag atgattatca cagcattata atagtaaaaa  17580
aatggaaata gcctctttct tctgttctgt tcatagcaca gtgcctcata cgcagtaggt  17640
tattattaca tggtaactgg ctaccccaac tgattaggaa agaagtaaat ttgttttata  17700
aaaatacata ctcattgagg tgcatagaat aattaagaaa ttaaaagaca cttgtaattt  17760
tgaatccagt gaatacccac tgttaatatt tggtatatct ctttctagtc tttttttccc  17820
ttttgcatgt attttcttta agactcccac ccccactgga tcatctctgc atgttctaat  17880
ctgctttttt cacagcagat tctaagcctc tttgaatatc aacacaaact tcaacaactt  17940
catctataga tgccaaataa taaattcatt tttatttact taaccacttc ctttggatgc  18000
ttaggtcatt ctgatgtttt gctattgaaa ccaatgctat actgaacact tctgtcacta  18060
aaactttgca cacactcatg aatagcttct taggataaat ttttagagat ggatttgcta  18120
aatcagagac catttttttaa aattaaaaaa caattattca tatcgtttgg catgtaagac  18180
agtaaatttt ccttttattt tgacaggatt caactggaag ctttgtgctg cctttccggc  18240
aagtcatgta tgctccatat cccaccacac acatagatgt ggatgtcaat actgtgaagc  18300
agatgccacc ctgtcatgaa catatttata atcagcgtag atacatgaga tccgagctga  18360
cagccttctg gagagccact tcagaagaag acatggctca ggatacgatc atctacactg  18420
acgaaagctt tactcctgat ttgtacgtaa tgctctgcct gctggtactg tagtcaagca  18480
atatgaaatt gtgtctttta cgaataaaaa caaaacagaa gttgcattta aaaagaaaga  18540
aatattacca gcagaattat gcttgaagaa acatttaatc aagcattttt ttcttaaatg  18600
ttcttctttt tccatacaat tgtgtttacc ctaaaatagg taagattaac ccttaaagta  18660
aatatttaac tatttgttta ataaatatat attgagctcc taggcactgt tctaggtacc  18720
gggcttaata gtggccaacc agacagcccc agccccagcc cctacattgt gtatagtcta  18780
ttatgtaaca gttattgaat ggacttatta acaaaaccaa agaagtaatt ctaagtcttt  18840
```

-continued

```
tttttcttga catatgaata taaaatacag caaaactgtt aaaatatatt aatggaacat  18900
ttttttactt tgcattttat attgttattc acttcttatt ttttttaaa aaaaaaagcc  18960
tgaacagtaa attcaaaagg aaaagtaatg ataattaatt gttgagcatg gacccaactt  19020
gaaaaaaaaa atgatgatga taaatctata atcctaaaac cctaagtaaa cacttaaaag  19080
atgttctgaa atcaggaaaa gaattatagt atacttttgt gtttctcttt tatcagttga  19140
aaaaaggcac agtagctcat gcctgtaaga acagagcttt gggagtgcaa ggcaggcgga  19200
tcacttgagg ccaggagttc cagaccagcc tgggcaacat agtgaaaccc catctctaca  19260
aaaaataaaa aagaattatt ggaatgtgtt tctgtgtgcc tgtaatccta gctattccga  19320
aagctgaggc aggaggatct tttgagccca ggagtttgag gttacaggga gttatgatgt  19380
gccagtgtac tccagcctgg ggaacaccga gactctgtct tatttaaaaa aaaaaaaaaa  19440
aaaatgcttg caataatgcc tggcacatag aaggtaacag taagtgttaa ctgtaataac  19500
ccaggtctaa gtgtgtaagg caatagaaaa attggggcaa ataagcctga cctatgtatc  19560
tacagaatca gtttgagctt aggtaacaga cctgtggagc accagtaatt acacagtaag  19620
tgttaaccaa aagcatagaa taggaatatc ttgttcaagg gacccccagc cttatacatc  19680
tcaaggtgca gaaagatgac ttaatatagg acccattttt tcctagttct ccagagtttt  19740
tattggttct tgagaaagta gtaggggaat gttttagaaa atgaattggt ccaactgaaa  19800
ttacatgtca gtaagttttt atatattggt aaattttagt agacatgtag aagttttcta  19860
attaatctgt gccttgaaac attttctttt ttcctaaagt gcttagtatt ttttccgttt  19920
tttgattggt tacttgggag ctttttgag gaaatttagt gaactgcaga atgggtttgc  19980
aaccatttgg tatttttgtt ttgtttttta gaggatgtat gtgtatttta acatttctta  20040
atcattttta gccagctatg tttgttttgc tgatttgaca aactacagtt agacagctat  20100
tctcattttg ctgatcatga caaaataata tcctgaattt ttaaattttg catccagctc  20160
taaattttct aaacataaaa ttgtccaaaa aatagtattt tcagccacta gattgtgtgt  20220
taagtctatt gtcacagagt cattttactt ttaagtatat gtttttacat gttaattatg  20280
tttgttattt ttaattttaa ctttttaaaa taattccagt cactgccaat acatgaaaaa  20340
ttggtcactg gaattttttt tttgactttt attttaggtt catgtgtaca tgtgcaggtg  20400
tgttatacag gtaaattgcg tgtcatgagg gtttggtgta caggtgattt cattacccag  20460
gtaataagca tagtacccaa taggtagttt tttgatcctc acccttctcc caccctcaag  20520
taggccctgg tgttgctgtt tccttctttg tgtccatgta tactcagtgt ttagctccca  20580
cttagaagtg agaacatgcg gtagttggtt ttctgttcct ggattagttc acttaggata  20640
atgacctcta gctccatctg gtttttatgg ctgcatagta ttccatggtg tatatgtatc  20700
acattttctt tatccagtct accattgata ggcatttagg ttgattccct gtctttgtta  20760
tcatgaatag tgctgtgatg aacatacaca tgcatgtgtc tttatggtag aaaaatttgt  20820
attcctttag gtacatatag aataatgggg ttgctagggt gaatggtagt tctattttca  20880
gttatttgag aaatcttcaa actgcttttc ataatagcta aactaattta cagtcccgcc  20940
agcagtgtat aagtgttccc ttttctccac aaccttgcca acatctgtga ttttttgact  21000
ttttaataat agccattcct agagaattga tttgcaattc tctattagtg atattaagca  21060
ttttttcata tgctttttag ctgtctgtat atattcttct gaaaaatttt catgtccttt  21120
gcccagtttg tagtggggtg ggttgttttt tgcttgttaa ttagttttaa gttccttcca  21180
gattctgcat atccctttgt tggatacatg gtttgcagat atttttctcc cattgtgtag  21240
```

-continued

```
gttgtctttt actctgttga tagtttcttt tgccatgcag gagctcgtta ggtcccattt  21300
gtgtttgttt ttgttgcagt tgcttttggc gtcttcatca taaaatctgt gccagggcct  21360
atgtccagaa tggtatttcc taggttgtct tccagggttt ttacaatttt agattttacg  21420
tttatgtctt taatccatct tgagttgatt tttgtatatg gcacaaggaa ggggtccagt  21480
ttcactccaa ttcctatggc tagcaattat cccagcacca tttattgaat acggagtcct  21540
ttccccattg cttgtttttt gtcaactttg ttgaagatca gatggttgta agtgtgtggc  21600
tttatttctt ggctctctat tctccattgg tctatgtgtc tgtttttata acagtaccct  21660
gctgttcagg ttcctatagc cttttagtat aaaatcggct aatgtgatgc ctccagcttt  21720
gttctttttg cttaggattg ctttggctat ttgggctcct ttttgggtcc atattaattt  21780
taaaacagtt ttttctggtt ttgtgaagga tatcattggt agtttatagg aatagcattg  21840
aatctgtaga ttgctttggg cagtatggcc attttaacaa tattaattct tcctatctat  21900
gaatatggaa tgtttttcca tgtgtttgtg tcatctcttt atacctgatg tataaagaaa  21960
agctggtatt attcctactc aatctgttcc aaaaaattga ggaggaggaa ctcttcccta  22020
atgaggccag catcattctg ataccaaaac ctggcagaga cacaacagaa aaaagaaaac  22080
ttcaggccaa tatccttgat gaatatagat gcaaaaatcc tcaacaaaat actagcaaac  22140
caaatccagc agcacatcaa aaagctgatc tactttgatc aagtaggctt tatccctggg  22200
atgcaaggtt ggttcaacat acacaaatca ataagtgtga ttcatcacat aaacagagct  22260
aaaaacaaaa accacaagat tatctcaata ggtagagaaa aggttgtcaa taaaatttaa  22320
catcctccat gttaaaaacc ttcagtaggt caggtgtagt gactcacacc tgtaatccca  22380
gcactttggg aggccaaggc gggcatatct cttaagccca ggagttcaag acgagcctag  22440
gcagcatggt gaaaccccat ctctacaaaa aaaaaaaaaa aaaaaaatta gcttggtatg  22500
gtgacatgca cctatagtcc cagctattca ggaggttgag gtgggaggat tgtttgagcc  22560
cgggaggcag aggttggcag cgagctgaga tcatgccacc gcactccagc ctgggcaacg  22620
gagtgagacc ctgtctcaaa aaagaaaaat cacaaacaat cctaaacaaa ctaggcattg  22680
aaggaacatg cctcaaaaaa ataagaacca tctatgacag acccatagcc aatatcttac  22740
caaatgggca aaagctggaa gtattctcct tgagaaccgt aacaagacaa ggatgtccac  22800
tctcaccact ccttttcagc atagttctgg aagtcctagc cagagcaatc aggaaagaga  22860
aagaaagaaa gacattcaga taggaagaga agaagtcaaa ctatttctgt ttgcaggcag  22920
tataattctg tacctagaaa atctcatagt ctctgcccag aaactcctaa atctgttaaa  22980
aatttcagca aagttttggc attctctata ctccaacacc ttccaaagtg agagcaaaat  23040
caagaacaca gtcccattca caatagccgc aaaacgaata aaatacctag gaatccagct  23100
aaccagggag gtgaaagatc tctatgagaa ttacaaaaca ctgctgaaag aaatcagaga  23160
tgacacaaac aaatggaaat gttctttttt aacaccttgc tttatctaat tcacttatga  23220
tgaagatact cattcagtgg aacaggtata ataagtccac tcgattaaat ataagcctta  23280
ttctctttcc agagcccaag aaggggcact atcagtgccc agtcaataat gacgaaatgc  23340
taatattttt cccctttacg gtttctttct tctgtagtgt ggtacactcg tttcttaaga  23400
taaggaaact tgaactacct tcctgtttgc ttctacacat acccattctc ttttttttgcc  23460
actctggtca ggtataggat gatccctacc actttcagtt aaaaactcct cctcttacta  23520
aatgttctct taccctctgg cctgagtaga acctagggaa aatggaagag aaaaagatga  23580
```

-continued aagggaggtg gggcctggga agggaataag tagtcctgtt tgtttgtgtg tttgctttag 23640
cacctgctat atcctaggtg ctgtgttagg cacacattat tttaagtggc cattatatta 23700
ctactactca ctctggtcgt tgccaaggta ggtagtactt tcttggatag ttggttcatg 23760
ttacttacag atggtgggct tgttgaggca aacccagtgg ataatcatcg gagtgtgttc 23820
tctaatctca ctcaaatttt tcttcacatt ttttggtttg ttttggtttt tgatggtagt 23880
ggcttatttt tgttgctggt ttgtttttttg tttttttttg agatggcaag aattggtagt 23940
tttatttatt aattgcctaa gggtctctac ttttttttaaa agatgagagt agtaaaatag 24000
attgatagat acatacatac ccttactggg gactgcttat attctttaga gaaaaaatta 24060
catattagcc tgacaaacac cagtaaaatg taaatatatc cttgagtaaa taaatgaatg 24120
tatattttgt gtctccaaat atatatatct atattcttac aaatgtgttt atatgtaata 24180
tcaatttata agaacttaaa atgttggctc aagtgaggga ttgtggaagg tagcattata 24240
tggccatttc aacatttgaa ctttttttctt ttcttcattt tcttcttttc ttcaggaata 24300
tttttcaaga tgtcttacac agagacactc tagtgaaagc cttcctggat caggtaaatg 24360
ttgaacttga gattgtcaga gtgaatgata tgacatgttt tcttttttaa tatatcctac 24420
aatgcctgtt ctatatattt atattcccct ggatcatgcc ccagagttct gctcagcaat 24480
tgcagttaag ttagttacac tacagttctc agaagagtct gtgagggcat gtcaagtgca 24540
tcattacatt ggttgcctct tgtcctagat ttatgcttcg ggaattcaga cctttgttta 24600
caatataata aatattattg ctatctttta aagatataat aataagatat aaagttgacc 24660
acaactactg ttttttgaaa catagaattc ctggtttaca tgtatcaaag tgaaatctga 24720
cttagctttt acagatataa tatatacata tatatatcct gcaatgcttg tactatatat 24780
gtagtacaag tatatatata tgtttgtgtg tgtatatata tatagtacga gcatatatac 24840
atattaccag cattgtagga tatatatatg tttatatatt aaaaaaaagt tataaactta 24900
aaaccctatt atgttatgta gagtatatgt tatatatgat atgtaaaata tataacatat 24960
actctatgat agagtgtaat atattttttta tatatatttt aacatttata aaatgataga 25020
attaagaatt gagtcctaat ctgttttatt aggtgctttt tgtagtgtct ggtctttcta 25080
aagtgtctaa atgatttttc cttttgactt attaatgggg aagagcctgt atattaacaa 25140
ttaagagtgc agcattccat acgtcaaaca acaaacattt taattcaagc attaacctat 25200
aacaagtaag ttttttttttt ttttttgaga aagggaggtt gtttatttgc ctgaaatgac 25260
tcaaaaatat ttttgaaaca tagtgtactt atttaaataa catctttatt gtttcattct 25320
tttaaaaaat atctacttaa ttacacagtt gaaggaaatc gtagattata tggaacttat 25380
ttcttaatat attacagttt gttataataa cattctgggg atcaggccag gaaactgtgt 25440
catagataaa gctttgaaat aatgagatcc ttatgtttac tagaaatttt ggattgagat 25500
ctatgaggtc tgtgacatat tgcgaagttc aaggaaaatt cgtaggcctg gaatttcatg 25560
cttctcaagc tgacataaaa tccctcccac tctccacctc atcatatgca cacattctac 25620
tcctacccac ccactccacc ccctgcaaaa gtacaggtat atgaatgtct caaaaccata 25680
ggctcatctt ctaggagctt caatgttatt tgaagatttg ggcagaaaaa attaagtaat 25740
acgaaataac ttatgtatga gttttaaaag tgaagtaaac atggatgtat tctgaagtag 25800
aatgcaaaat ttgaatgcat ttttaaagat aaattagaaa acttctaaaa actgtcagat 25860
tgtctgggcc tggtggctta tgcctgtaat cccagcactt tgggagtccg aggtgggtgg 25920
atcacaaggt caggagatcg agaccatcct gccaacatgg tgaaaccccg tctctactaa 25980

-continued

```
gtatacaaaa attagctggg cgtggcagcg tgtgcctgta atcccagcta cctgggaggc  26040
tgaggcagga gaatcgcttg aacccaggag gtgtaggttg cagtgagtca agatcgcgcc  26100
actgcacttt agcctggtga cagagctaga ctccgtctca aaaaaaaaaa aaaatatcag  26160
attgttccta cacctagtgc ttctatacca cactcctgtt agggggcatc agtggaaatg  26220
gttaaggaga tgtttagtgt gtattgtctg ccaagcactg tcaacactgt catagaaact  26280
tctgtacgag tagaatgtga gcaaattatg tgttgaaatg gttcctctcc ctgcaggtct  26340
ttcagctgaa acctggctta tctctcagaa gtactttcct tgcacagttt ctacttgtcc  26400
ttcacagaaa agccttgaca ctaataaaat atatagaaga cgatacgtga gtaaaactcc  26460
tacacggaag aaaaaccttt gtacattgtt tttttgtttt gtttcctttg tacattttct  26520
atatcataat ttttgcgctt cttttttttt tttttttttt ttttttttcca ttatttttag  26580
gcagaaggga aaaaagccct ttaaatctct tcggaacctg aagatagacc ttgatttaac  26640
agcagagggc gatcttaaca taataatggc tctggctgag aaaattaaac caggcctaca  26700
ctcttttatc tttggaagac ctttctacac tagtgtgcaa gaacgagatg ttctaatgac  26760
tttttaaatg tgtaacttaa taagcctatt ccatcacaat catgatcgct ggtaaagtag  26820
ctcagtggtg tggggaaacg ttcccctgga tcatactcca gaattctgct ctcagcaatt  26880
gcagttaagt aagttacact acagttctca caagagcctg tgaggggatg tcaggtgcat  26940
cattacattg ggtgtctctt ttcctagatt tatgcttttg ggatacagac ctatgtttac  27000
aatataataa atattattgc tatcttttaa agatataata ataggatgta aacttgacca  27060
caactactgt ttttttgaaa tacatgattc atggtttaca tgtgtcaagg tgaaatctga  27120
gttggctttt acagatagtt gactttctat cttttggcat tctttggtgt gtagaattac  27180
tgtaatactt ctgcaatcaa ctgaaaacta gagcctttaa atgatttcaa ttccacagaa  27240
agaaagtgag cttgaacata ggatgagctt tagaaagaaa attgatcaag cagatgttta  27300
attggaattg attattagat cctactttgt ggatttagtc cctgggattc agtctgtaga  27360
aatgtctaat agttctctat agtccttgtt cctggtgaac cacagttagg gtgttttgtt  27420
tattttattg ttcttgctat tgttgatatt ctatgtagtt gagctctgta aaaggaaatt  27480
gtattttatg ttttagtaat tgttgccaac tttttaaatt aattttcatt atttttgagc  27540
caaattgaaa tgtgcacctc ctgtgccttt tttctcctta gaaaatctaa ttacttggaa  27600
caagttcaga tttcactggt cagtcatttt catcttgttt tcttcttgct aagtcttacc  27660
atgtacctgc tttggcaatc attgcaactc tgagattata aaatgcctta gagaatatac  27720
taactaataa gatctttttt tcagaaacag aaaatagttc cttgagtact tccttcttgc  27780
atttctgcct atgtttttga agttgttgct gtttgcctgc aataggctat aaggaatagc  27840
aggagaaatt ttactgaagt gctgttttcc taggtgctac tttggcagag ctaagttatc  27900
ttttgttttc ttaatgcgtt tggaccattt tgctggctat aaaataactg attaatataa  27960
ttctaacaca atgttgacat tgtagttaca caaacacaaa taaatatttt atttaaaatt  28020
ctggaagtaa tataaaaggg aaaatatatt tataagaaag ggataaaggt aatagagccc  28080
ttctgccccc cacccaccaa atttacacaa caaaatgaca tgttcgaatg tgaaaggtca  28140
taatagcttt cccatcatga atcagaaaga tgtggacagc ttgatgtttt agacaaccac  28200
tgaactagat gactgttgta ctgtagctca gtcatttaaa aaatatataa atactacctt  28260
gtagtgtccc atactgtgtt ttttacatgg tagattctta tttaagtgct aactggttat  28320
```

-continued

```
tttctttggc tggtttattg tactgttata cagaatgtaa gttgtacagt gaaataagtt  28380
attaaagcat gtgtaaacat tgttatatat cttttctcct aaatggagaa ttttgaataa  28440
aatatatttg aaattttgcc tctttcagtt gttcattcag aaaaaaatac tatgatattt  28500
gaagactgat cagcttctgt tcagctgaca gtcatgctgg atctaaactt tttttaaaat  28560
taattttgtc ttttcaaaga aaaaatattt aaagaagctt tataatataa tcttatgtta  28620
aaaaaacttt ctgcttaact ctctggattt catttttgatt tttcaaatta tatattaata  28680
tttcaaatgt aaaatactat ttagataaat tgtttttaaa cattcttatt attataatat  28740
taatataacc taaactgaag ttattcatcc caggtatcta atacatgtat ccaaagtaaa  28800
aatccaagga atctgaacac tttcatctgc aaagctagga ataggtttga cattttcact  28860
ccaagaaaaa gttttttttt gaaaatagaa tagttgggat gagaggtttc tttaaaagaa  28920
gactaactga tcacattact atgattctca aagaagaaac caaaacttca tataatacta  28980
taaagtaaat ataaaatagt tccttctata gtatatttct ataatgctac agtttaaaca  29040
gatcactctt atataatact attttgattt tgatgtagaa ttgcacaaat tgatatttct  29100
cctatgatct gcagggtata gcttaaagta acaaaaacag tcaaccacct ccatttaaca  29160
cacagtaaca ctatgggact agttttatta cttccatttt acaaatgagg aaactaaagc  29220
ttaaagatgt gtaatacacc gcccaaggtc acacagctgg taaaggtgga tttcatccca  29280
gacagttaca gtcattgcca tgggcacagc tcctaactta gtaactccat gtaactggta  29340
ctcagtgtag ctgaattgaa aggagagtaa ggaagcaggt tttacaggtc tacttgcact  29400
attcagagcc cgagtgtgaa tccctgctgt gctgcttgga gaagttactt aacctatgca  29460
aggttcattt tgtaaatatt ggaaatggag tgataatacg tacttcacca gaggatttaa  29520
tgagacctta tacgatcctt agttcagtac ctgactagtg cttcataaat gctttttcat  29580
ccaatctgac aatctccagc ttgtaattgg ggcatttaga acatttaata tgattattgg  29640
catggtaggt taaagctgtc atcttgctgt tttctatttg ttctttttgt tttctcctta  29700
cttttggatt tttttattct actatgtctt ttctattgtc ttattaacta tactctttga  29760
tttattttag tggttgtttt agggttatac ctctttctaa tttaccagtt tataaccagt  29820
ttatatacta cttgacatat agcttaagaa acttactgtt gttgtctttt tgctgttatg  29880
gtcttaacgt ttttatttct acaaacatta taaactccac actttattgt tttttaattt  29940
tacttataca gtcaattatc ttttaaagat atttaaatat aaacattcaa aacaccccaa  30000
t                                                                  30001
```

<210> SEQ ID NO 3
<211> LENGTH: 1031
<212> TYPE: DNA
<213> ORGANISM: homo sapiens

<400> SEQUENCE: 3

```
attcccggga tacgtaacct acggtgtccc gctaggaaag agaggtgcgt caaacagcga    60
caagttccgc ccacgtaaaa gatgacgctt ggtgtgtcag ccgtccctgc tgcccggttg   120
cttctctttt gggggcgggg tctagcaaga gcaggtgtgg gtttaggaga tatctccgga   180
gcatttggat aatgtgacag ttggaatgca gtgatgtcga ctctttgccc accgccatct   240
ccagctgttg ccaagacaga gattgcttta agtggcaaat cacctttatt agcagctact   300
tttgcttact gggacaatat tcttggtcct agagtaaggc acatttgggc tccaaagaca   360
gaacaggtac ttctcagtga tggagaaata acttttcttg ccaaccacac tctaaatgga   420
```

gaaatccttc gaaatgcaga gagtggtgct atagatgtaa agttttttgt cttgtctgaa 480
aagggagtga ttattgtttc attaatcttt gatggaaact ggaatgggga tcgcagcaca 540
tatggactat caattatact tccacagaca gaacttagtt tctacctccc acttcataga 600
gtgtgtgttg atagattaac acatataatc cggaaaggaa gaatatggat gcataaggaa 660
agacaagaaa aatgtccaga agattatctt agaaggcaca gagagaatgg aagatcaggg 720
tcagagtatt attccaatgc ttactggaga agtgattcct gtaatggaaa ctgctttcct 780
ctatgaaatt cccccgggtt cctggaggaa atagatatag gctgatacag ttacccaatg 840
atggatgaat attgggggac cgcctggtca ttgaaaggct ttcttttctc caggaaagaa 900
atttttttcc ttttccataa aaagcttggg aatggaagac aacaattccc attctttttt 960
tgcgttccac ccctatgtga caacagaaat ttttggggaa acaacaacga aaaaatttta 1020
tcccgcgcgc a 1031

<210> SEQ ID NO 4
<211> LENGTH: 3244
<212> TYPE: DNA
<213> ORGANISM: homo sapiens

<400> SEQUENCE: 4
gggcggggct gcggttgcgg tgcctgcgcc cgcggcggcg gaggcgcagg cggtggcgag 60
tggatatctc cggagcattt ggataatgtg acagttggaa tgcagtgatg tcgactcttt 120
gcccaccgcc atctccagct gttgccaaga cagagattgc tttaagtggc aaatcacctt 180
tattagcagc tacttttgct tactgggaca atattcttgg tcctagagta aggcacattt 240
gggctccaaa gacagaacag gtacttctca gtgatggaga aataactttt cttgccaacc 300
acactctaaa tggagaaatc cttcgaaatg cagagagtgg tgctatagat gtaaagtttt 360
ttgtcttgtc tgaaaaggga gtgattattg tttcattaat ctttgatgga aactggaatg 420
gggatcgcag cacatatgga ctatcaatta tacttccaca gacagaactt agtttctacc 480
tcccacttca tagagtgtgt gttgatagat taacacatat aatccggaaa ggaagaatat 540
ggatgcataa ggaaagacaa gaaaatgtcc agaagattat cttagaaggc acagagagaa 600
tggaagatca gggtcagagt attattccaa tgcttactgg agaagtgatt cctgtaatgg 660
aactgctttc atctatgaaa tcacacagtg ttcctgaaga aatagatata gctgatacag 720
tactcaatga tgatgatatt ggtgacagct gtcatgaagg ctttcttctc aatgccatca 780
gctcacactt gcaaacctgt ggctgttccg ttgtagtagg tagcagtgca gagaaagtaa 840
ataagatagt cagaacatta tgcctttttc tgactccagc agagagaaaa tgctccaggt 900
tatgtgaagc agaatcatca tttaaatatg agtcagggct ctttgtacaa ggcctgctaa 960
aggattcaac tggaagcttt gtgctgcctt tccggcaagt catgtatgct ccatatccca 1020
ccacacacat agatgtggat gtcaatactg tgaagcagat gccaccctgt catgaacata 1080
tttataatca gcgtagatac atgagatccg agctgacagc cttctggaga gccacttcag 1140
aagaagacat ggctcaggat acgatcatct acactgacga aagctttact cctgatttga 1200
atatttttca agatgtctta cacagagaca ctctagtgaa agccttcctg gatcaggtct 1260
ttcagctgaa acctggctta tctctcagaa gtactttcct tgcacagttt ctacttgtcc 1320
ttcacagaaa agccttgaca ctaataaaat atatagaaga cgatacgcag aagggaaaaa 1380
agccctttaa atctcttcgg aacctgaaga tagaccttga tttaacagca gagggcgatc 1440

-continued

```
ttaacataat aatggctctg gctgagaaaa ttaaaccagg cctacactct tttatctttg   1500

gaagaccttt ctacactagt gtgcaagaac gagatgttct aatgactttt taaatgtgta   1560

acttaataag cctattccat cacaatcatg atcgctggta aagtagctca gtggtgtggg   1620

gaaacgttcc cctggatcat actccagaat tctgctctca gcaattgcag ttaagtaagt   1680

tacactacag ttctcacaag agcctgtgag ggatgtcag gtgcatcatt acattgggtg    1740

tctcttttcc tagatttatg cttttgggat acagacctat gtttacaata taataaatat   1800

tattgctatc ttttaaagat ataataatag gatgtaaact tgaccacaac tactgttttt   1860

ttgaaataca tgattcatgg tttacatgtg tcaaggtgaa atctgagttg gcttttacag   1920

atagttgact ttctatcttt tggcattctt tggtgtgtag aattactgta atacttctgc   1980

aatcaactga aaactagagc ctttaaatga tttcaattcc acagaaagaa agtgagcttg   2040

aacataggat gagctttaga aagaaaattg atcaagcaga tgtttaattg gaattgatta   2100

ttagatccta ctttgtggat ttagtccctg ggattcagtc tgtagaaatg tctaatagtt   2160

ctctatagtc cttgttcctg gtgaaccaca gttagggtgt tttgtttatt ttattgttct   2220

tgctattgtt gatattctat gtagttgagc tctgtaaaag gaaattgtat tttatgtttt   2280

agtaattgtt gccaactttt taaattaatt ttcattattt ttgagccaaa ttgaaatgtg   2340

cacctcctgt gccttttttc tccttagaaa atctaattac ttggaacaag ttcagatttc   2400

actggtcagt cattttcatc ttgttttctt cttgctaagt cttaccatgt acctgctttg   2460

gcaatcattg caactctgag attataaaat gccttagaga atatactaac taataagatc   2520

tttttttcag aaacagaaaa tagttccttg agtacttcct tcttgcattt ctgcctatgt   2580

ttttgaagtt gttgctgttt gcctgcaata ggctataagg aatagcagga gaaattttac   2640

tgaagtgctg ttttcctagg tgctactttg gcagagctaa gttatctttt gttttcttaa   2700

tgcgtttgga ccattttgct ggctataaaa taactgatta atataattct aacacaatgt   2760

tgacattgta gttacacaaa cacaaataaa tattttattt aaaattctgg aagtaatata   2820

aaagggaaaa tatatttata agaaagggat aaaggtaata gagcccttct gccccccacc   2880

caccaaattt acacaacaaa atgacatgtt cgaatgtgaa aggtcataat agctttccca   2940

tcatgaatca gaaagatgtg gacagcttga tgttttagac aaccactgaa ctagatgact   3000

gttgtactgt agctcagtca tttaaaaaat atataaatac taccttgtag tgtcccatac   3060

tgtgtttttt acatggtaga ttcttattta agtgctaact ggttattttc tttggctggt   3120

ttattgtact gttatacaga atgtaagttg tacagtgaaa taagttatta aagcatgtgt   3180

aaacattgtt atatatcttt tctcctaaat ggagaatttt gaataaaata tatttgaaat   3240

tttg                                                                3244
```

<210> SEQ ID NO 5
<211> LENGTH: 761
<212> TYPE: DNA
<213> ORGANISM: homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5

```
cacgaggctt tgatatttct tacaacgaat ttcatgtgta gacccactaa acagaagcta     60
```

taaaagttgc atggtcaaat aagtctgaga aagtctgcag atgatataat tcacctgaag 120
agtcacagta tgtagccaaa tgttaaaggt tttgagatgc catacagtaa atttaccaag 180
cattttctaa atttatttga ccacagaatc cctattttaa gcaacaactg ttacatccca 240
tggattccag gtgactaaag aatacttatt tcttaggata tgttttattg ataataacaa 300
ttaaaatttc agatatcttt cataagcaaa tcagtggtct ttttacttca tgttttaatg 360
ctaaaatatt ttcttttata gatagtcaga acattatgcc tttttctgac tccagcagag 420
agaaaatgct ccaggttatg tgaagcagaa tcatcattta aatatgagtc agggctcttt 480
gtacaaggcc tgctaaagga ttcaactgga agctttgtgc tgcctttccg gcaagtcatg 540
tatgctccat atcccaccac acacatagat gtggatgtca atactgtgaa gcagatgcca 600
ccctgtcatg aacatattta taatcagcgt agatacatga gatccgagct gacagccttc 660
tggagagcca cttcagaaga agacatggct cangatacga tcatctacac tgacgaaagc 720
tntactcctg atttgaatat ttttcaagat gtcttacaca g 761

<210> SEQ ID NO 6
<211> LENGTH: 1901
<212> TYPE: DNA
<213> ORGANISM: homo sapiens

<400> SEQUENCE: 6
acgtaaccta cggtgtcccg ctaggaaaga gaggtgcgtc aaacagcgac aagttccgcc 60
cacgtaaaag atgacgcttg atatctccgg agcatttgga taatgtgaca gttggaatgc 120
agtgatgtcg actctttgcc caccgccatc tccagctgtt gccaagacag agattgcttt 180
aagtggcaaa tcacctttat tagcagctac ttttgcttac tgggacaata ttcttggtcc 240
tagagtaagg cacatttggg ctccaaagac agaacaggta cttctcagtg atggagaaat 300
aacttttctt gccaaccaca ctctaaatgg agaaatcctt cgaaatgcag agagtggtgc 360
tatagatgta aagtttttttg tcttgtctga aaagggagtg attattgttt cattaatctt 420
tgatggaaac tggaatgggg atcgcagcac atatggacta tcaattatac ttccacagac 480
agaacttagt ttctacctcc cacttcatag agtgtgtgtt gatagattaa cacatataat 540
ccggaaagga agaatatgga tgcataagga aagacaagaa aatgtccaga agattatctt 600
agaaggcaca gagagaatgg aagatcaggg tcagagtatt attccaatgc ttactggaga 660
agtgattcct gtaatggaac tgctttcatc tatgaaatca cacagtgttc ctgaagaaat 720
agatatagct gatacagtac tcaatgatga tgatattggt gacagctgtc atgaaggctt 780
tcttctcaag taagaatttt tcttttcata aaagctggat gaagcagata ccatcttatg 840
ctcacctatg acaagatttg gaagaaagaa aataacagac tgtctactta gattgttcta 900
gggacattac gtatttgaac tgttgcttaa atttgtgtta tttttcactc attatatttc 960
tatatatatt tggtgttatt ccatttgcta tttaaagaaa ccgagtttcc atcccagaca 1020
agaaatcatg gccccttgct tgattctggt ttcttgtttt acttctcatt aaagctaaca 1080
gaatcctttc atattaagtt gtactgtaga tgaacttaag ttatttaggc gtagaacaaa 1140
attattcata tttatactga tctttttcca tccagcagtg gagtttagta cttaagagtt 1200
tgtgccctta aaccagactc cctggattaa tgctgtgtac ccgtgggcaa ggtgcctgaa 1260
ttctctatac acctatttcc tcatctgtaa aatggcaata atagtaatag tacctaatgt 1320
gtagggttgt tataagcatt gagtaagata aataatataa agcacttaga acagtgcctg 1380

-continued

```
gaacataaaa acacttaata atagctcata gctaacattt cctatttaca tttcttctag   1440

aaatagccag tatttgttga gtgcctacat gttagttcct ttactagttg ctttacatgt   1500

attatcttat attctgtttt aaagtttctt cacagttaca gattttcatg aaattttact   1560

tttaataaaa gagaagtaaa agtataaagt attcactttt atgttcacag tcttttcctt   1620

taggctcatg atggagtatc agaggcatga gtgtgtttaa cctaagagcc ttaatggctt   1680

gaatcagaag cactttagtc ctgtatctgt tcagtgtcag cctttcatac atcattttaa   1740

atcccatttg actttaagta agtcacttaa tctctctaca tgtcaatttc ttcagctata   1800

aaatgatggt atttcaataa ataaatacat taattaaatg atattatact gactaattgg   1860

gctgttttaa ggcaaaaaaa aaaaaaaaaa aaaaaaaaaa a                        1901


<210> SEQ ID NO 7
<211> LENGTH: 562
<212> TYPE: DNA
<213> ORGANISM: homo sapiens
<220> FEATURE:
<221> NAME/KEY: misc_feature
<222> LOCATION: (166)..(166)
<223> OTHER INFORMATION: n is a, c, g, or t

<400> SEQUENCE: 7

agacgtaacc tacggtgtcc cgctaggaaa gagagatatc tccggagcat ttggataatg     60

tgacagttgg aatgcagtga tgtcgactct ttgcccaccg ccatctccag ctgttgccaa    120

gacagagatt gctttaagtg gcaaatcacc tttattagca gctacntttt gcttactggg    180

acaatattct tggtcctaga gtaaggcaca tttgggctcc aaagacagaa caggtacttc    240

tcagtgatgg agaaataact tttcttgcca accacactct aaatggagaa atccttcgaa    300

atgcagagag tggtgctata gatgtaaagt tttttgtctt gtctgaaaag ggagtgatta    360

ttgtttcatt aatctttgat ggaaactgga atggggatcg cagcacatat ggactatcaa    420

ttatacttcc acagacagaa cttagtttct acctcccact tcatagagtg tgtgttgata    480

gattaacaca tataatccgg aaaggaagaa tatggatgca taaggaaaga caagaaaatg    540

tccagaagat tatcttagaa gg                                             562


<210> SEQ ID NO 8
<211> LENGTH: 798
<212> TYPE: DNA
<213> ORGANISM: homo sapiens

<400> SEQUENCE: 8

gggctctctt ttgggggcgg ggtctagcaa gagcagatat ctccggagca tttggataat     60

gtgacagttg gaatgcagtg atgtcgactc tttgcccacc gccatctcca gctgttgcca    120

agacagagat tgctttaagt ggcaaatcac ctttattagc agctactttt gcttactggg    180

acaatattct tggtcctaga gtaaggcaca tttgggctcc aaagacagaa caggtacttc    240

tcagtgatgg agaaataact tttcttgcca accacactct aaatggagaa atccttcgaa    300

atgcagagag tggtgctata gatgtaaagt tttttgtctt gtctgaaaag ggagtgatta    360

ttgtttcatt aatctttgat ggaaactgga atggggatcg cagcacatat ggactatcaa    420

ttatacttcc acagacagaa cttagtttct acctcccact tcatagagtg tgtgttgata    480

gattaacaca tataatccgg aaaggaagaa tatggatgca taaggaaaga caagaaaatg    540

tccagaagat tatcttagaa ggcacagaga gaatggaaga tcagggtcag agtattattc    600

caatgcttac tggagaagtg attcctgtaa tgggactgct ttcatctatg aaatcacaca    660
```

-continued gtgttcctga agaaatagat atagctgata cagtactcca tgatgatgat atttggtgac 720
agctgtcatg aaaggctttc ttctcaagta ggaatttttt cttttcataa aagctgggat 780
gaagccagat tcccatct 798

<210> SEQ ID NO 9
<211> LENGTH: 169
<212> TYPE: DNA
<213> ORGANISM: homo sapiens

<400> SEQUENCE: 9
aaacagcgac aagttccgcc cacgtaaaag atgatgcttg gtgtgtcagc cgtccctgct 60
gcccggttgc ttctcttttg ggggcggggt ctagcaagag cagatatctc cggagcattt 120
ggataatgtg acagttggaa tgcggtgatg tcgactcttt gcccaccgc 169

<210> SEQ ID NO 10
<211> LENGTH: 176
<212> TYPE: DNA
<213> ORGANISM: homo sapiens

<400> SEQUENCE: 10
aaaacgtcat cgcacataga aaacagacag acgtaaccta cggtgtcccg ctaggaaaga 60
gaggtgcgtc aaacagcgac aagttccgcc cacgtaaaag atgacgcttg atatctccgg 120
agcatttgga taatgtgaca gttggaatgc agtgatgtcg actctttgcc caccgc 176

<210> SEQ ID NO 11
<211> LENGTH: 30001
<212> TYPE: DNA
<213> ORGANISM: macaca mulatta
<220> FEATURE:
<221> NAME/KEY: misc_feature
<222> LOCATION: (26113)..(26155)
<223> OTHER INFORMATION: n is a, c, g, or t
<220> FEATURE:
<221> NAME/KEY: misc_feature
<222> LOCATION: (28797)..(29186)
<223> OTHER INFORMATION: n is a, c, g, or t

<400> SEQUENCE: 11
aatctctaag caatttttttg gggaagaaag aattgcaatt agggcatacg tgtagatcag 60
atggtcttcg gtatatccaa cgacaaagaa aaggtgggag gtttcgttaa aaaagagaaa 120
tgttacatag tacttttaga gaaaattcac tggcactatt aagggtctga ggagctggta 180
agtttcaatt ggtgagtgat ggtggtagat aaaattagag ctgcagcagg tcatttcagc 240
aactatcaga taaaactggt ctcaggtcac aacgggcagt ttcagcagct agacttgaaa 300
gaattacact gcgggagcaa tgtcatttgt cctgcatgct tttctacccc ctacccccac 360
ttttttagtt gggtataaca agaacgaccc aaattgtatg atcaactttc acaaagcata 420
gaacagtagg aaaagggtct gtttctgcag aagatgtaga cgttgagagc cattttatgt 480
atttatttct ccctttcttc atcggtgaat gattaaaatg ttctgtatga tttttagtga 540
tgagaaaggt taaacgccac tcatctgtag taagtgtaat ctacacactt gcagaccaaa 600
aggcataagg tttaaaaaac ctttgttttt ttacacatca aacagagtgg tataaatgct 660
actcatctgt agtaagtgaa atctatacac ctgcagacca acgacgcaag gtttcaaaaa 720
tctttgtgtt ttttacacat caaacagaat ggtacatttt tcaaaagttt aaaaaaaaaa 780
aaaatccaca tatcacaact agcaaaaatg acattcccca gtgtgaaaat catgcttgag 840

-continued

```
agaattctta catgtaaagg caaaattgca gtgactttac aagggacctg gggattcccg    900
cccacagtgt ggagctgtcc cctaccaggg tttgcggcgg agttttgaat gtacttaaca    960
gtgtctcacg gtaaaaacaa aacttcatcc accaaatatt tgttgagcgc ccactgcctg   1020
ccaagcacaa acaaaaccat tcaaaaccac gaaatcgtct gcactttctc cggatccagc   1080
agcctctgcg attaaggttt gcacacgcta ttgcgccaac gctcctccag agcgcgtctt   1140
aagataaaag aatgggacaa gttgcccctc cccctttcac gggcctcgtg cgtcaacgtc   1200
atcgcatata gaaaacacac agacgtaacc tacggtgtcc cgctaggaaa gagaggcgcg   1260
tcaaacagcg acaagttccg cccacgtaaa agatgacgct tggtgcgtca gccgtccctg   1320
ctgcccggtt ccttctctct gggggcgggg cctggctaga gcaggtgtgg gtttaggagg   1380
tgtgtgtttt tgtttttcct accctctccc ctctacttgc tctcacagta ctcgctgagg   1440
gtgaacaaga aaagacctga taaagattaa ccagaagaaa acaaagaggg aaacaactgc   1500
agcctgtagc gggctctgga gcttaagaga ggcgcgctag gcgccgggcc gtgggcgtgg   1560
tcggggcggg gtcgggccag gggcggggct gcggttgcgg tccctgcgcc cgcggcggcg   1620
gcggcggcgg cagcggaggc gcaggcggtg gcgagtgggt gagtgaagag gcggcgtcct   1680
ggcgggtgtc tgtttggcgt ccggttgccg ggaagagacg cgggtagcag ccggggctct   1740
cctcagagct cgacacattt ttactttccc tctcgtttct ctgaccgaag tcgggtgtcc   1800
ggctttcgcc tctagcgact ggtggaattg cctgcatctg ggccccgggc ttcgcggcgg   1860
cgcagggacg agggatggga atctggcctc ttcctcgctt tcccgcccgc agtgcgctgc   1920
cccagctgtc tccttcccgg ggacctgctg ggagcgctgc cgctacagac tcgagagaaa   1980
ggagcctcgg gcactgagag gcctcgcccg ggggaaggcc ggagggcggg cggcgggcgg   2040
cgagcggctc ctgcggacca agtctgggtt ctctgggaac ccgagacggt ccctgatggc   2100
gaggagatca tgcggggtgc tatgggggtg tggagacgtc tgcagaattt tagcccaagc   2160
ttctaaggag tgctgatgac ttgcatatga gggcagcaat gccagtcggt gtactcccta   2220
ttctgtggga catgatgtgg ttgcttcaca gctccgagat gacacagact tgcttaaagg   2280
aagtgaccat tgtgacttgg gcatcacttg actgatggta atcagttgca gacagaagtg   2340
cacagattac atgtctgtgt ccacactgga tcagtctggc cacgaggaac accacaggct   2400
ttgtattgag aaacaggagg gaggtcctgc actttcccag gaggggtggc cctttcagat   2460
gcaatcgaga ttgttaggct ctggtagagt ggttgcctgg ttgtggcagt tggcaaattc   2520
ctattcaaac tgttgccgtg cgtcaccagt taacaacaag ggtacacgat ctgtctggca   2580
ttacttctac tttgtacaaa ggatcaaaaa tactgttaga tatgattttt ctcagacttt   2640
gggaaacttt taacgtaatc tgtgaatatc acagaagcaa gactgtcata tagaggatat   2700
taataacctg gagtcagaat acttgaaata tggtgtcatt tgacacgggc tctgttatca   2760
ccacctttgc caagcccttt cacttgagga aaccctcaa tcagttggaa actgcctcat   2820
gctgacagta catctgaaac aaaaacgaga gtagttacca cattccagat tgttcactaa   2880
ggcagcattt atctgctcca ggaaaacatt acaagcaact tatgaagttg ataaaatatt   2940
ttgtttggct atgttggtac tccaaaagtt gctttcagag aaacaaagta aaccaaggag   3000
gacttctgtt gttcacgtct gcccttgggc tctattctac gttaattagg tagttcccag   3060
gaggactaga ttagcctacc tattgtctga gaaacttgga tctgtgagaa atggccagat   3120
agtgatacga acttcacctc ccagtctttc ctgatgttta agattgagaa agtgttgtga   3180
actttctggt gctgtaagca gttcactgtc cttaaagtgg tcctgggcag ctcctgttgt   3240
```

-continued

```
ggaaagtgga ccgatttagg attctgcttg gctttggact gggagaaaat aaactgcatg   3300
gttacaagta ttgagagcca agttggagaa ggtggcttac acctataatg ccagagcctt   3360
aggaggcagg ggcaagagga tcactggaag tcaggagttc aagcccaacc tgggcagcct   3420
agaccctgtc tctacaaaaa attaaaaact tagccgggcg cggtggtgtg cacctgtagt   3480
cctagctact tgggaggctg aggcaggagg gtcttttgag cccaggagtt tgaagttaca   3540
gggagctatg atcctgccag tgcactccag cctggatggc aaaacgagac cctgtctcta   3600
aaaaacaaga agtgagggct ttatgatcgt agaaattttg cttacaatag cagtggacca   3660
accacctttc taaataccaa tcagggaaga catagttgat ttttaacaaa catttaaaga   3720
aaaagcaaaa cctcaaactt agcactctac taacagtttt agccgatgct aattaaggta   3780
atcatgtctg catatatggg attactttca gaaagtgtat tgggaaacct ctcatgaacc   3840
ctgtgcaacc ctgagcaagc caccgtctca ctcagtttga atcttggctt ccctcaaaag   3900
actctgtggc taatgtttgg taactctctg gagtagccag cactgcatgt acataggata   3960
ggtacataaa acaattattg gttttgagct gatttttttc agctgcattt gcgtgtatgg   4020
atttttctca ccaaagacaa tgacttcaag tgttaataaa ataattgtac agctctccta   4080
attatacttc tctgtaacat ttcatttctc agactatttc ttttggtagg atttaaaact   4140
aaacaattca gtatgatctt tgttcttcat tttctttctt attctttttt ttttcgagac   4200
agagtctccc tctgttgtgc catctcagcc cattgcaacc tccgccacct gggttcaagt   4260
gattctcctg cctcagcctc ctgagtagct gggattacag gtgcccgcca ccacacctac   4320
ctaatttttt gtatttttag tagaggcggg gtttcaccat gttggctagg ctggtcttaa   4380
actcctgacc tcagatgatc cacctgcctc ggcctcccaa agagctggga tgataggcgt   4440
gacccaccat gcccgcccca ttttttttct tattctgtta ggagtgagag tgtaactagc   4500
agtctataat agttcaattt tcacaacgtg gtaaaaattt tccctgtaat tcaacgagat   4560
tttgcttcag ggctcagttc tgttttagga aatactttta ttttcagttt gatgatgaaa   4620
tattagagtt gtgatattgc ctttatgatt acctaccttt ttaacctaaa agaatgaaag   4680
aaaaatatgt ttacagtata attgtatggt tgcgtgttaa cttaattcat tatgttggcc   4740
tccagtttgc tgttgttcgt tatgacagca gtagtgtcat taccatttca attcagatta   4800
cattcctgta tttgatcatt gtaaactgat tgcttaaatt gtattaaaaa cagtggatat   4860
tttaaacaag ctgtactgct tatatccagt gctgtctcct aagactatta aattgatata   4920
acatatttaa aagtaaatat ttcctaaatg aatttttgaa attaaaaata cacgtgttaa   4980
aactgtcttt gtgttcaacc atttctgtac gtacttagag ttaactgttt tgccaggctc   5040
tgtatgccta ctcataatgt gataaaagca ctcatctaat gctctataaa tagaagtcag   5100
tgctttccat cagactgaac actcttggca agatgtggat aaaattattt aagtaaaatt   5160
gtttactttg tcatacattt acagatcaaa tgttagctcc caaagcaatc atatggcaaa   5220
gataggcata tcataatttg cctattagct gctttgtatt gctattatga tagatttcac   5280
agttttagat ctgcttagat gaaaatgtaa ttctttttac tgtcagtctt agatataagt   5340
cttcaattat agtacagtca cacattgctt aggaatgcat cattaggcga ttttgtcatt   5400
atgcaaacat catagagtat acttacataa acctatatag tacagccttt acgtacgtag   5460
gccatatggt atagtctatt gctcctaggc tacaaatctg tacagctgtt actgtactga   5520
atactataga cagttgtaac acagtggtat ttatttatct aaatatatcc aaacatagaa   5580
```

-continued

```
aaggtacagt taaagtatgg tataaaaaat aatgatatac ctatataggc cacttaccgt   5640
gaatggagct tgcaggacta gaagttgctc tgggtgagtc agtaagtaag tggtgaatga   5700
atgtgaaggc ctagaacatt actgtacaca ctgtagactt tataaacaca gtatgcttaa   5760
gctacaccaa atttatcttt acagtttttc ttcaataaaa aattaatgtg aacctactat   5820
aactttttaa ctttgtaaac tttttaattt tttaactttt aaaatactta gcttgaaaca   5880
caaacacgca tagctataca aaaatatttt ttctttatat ccttattcta gaagcttttt   5940
cctattttta acttttttt ttttacttgt tagtcgtttt tgttaaaaac taaaacacac   6000
acactttcac ctaagcatag acaggattag gatcatcagt ttcactccct tccacctcac   6060
tgccttccac ctccacatct tgtcccactg gaacgttttt agggggaata acacacatgt   6120
agctgtcacc tgctatgata acagtgcttt ctgttgaata cctcctgaag gacctgcctg   6180
aggctgtttt acatttaact taaaaaaaaa aataagtaga aggagtacac tctaaaataa   6240
caataaaagg tatagtctag tgaatacata aaccagcaac atagtagttt attatcaagt   6300
gttgtatact gtaataattg tatgtgctat actttaaatg acttgaaaaa ttgtactaag   6360
accttatgat ggttacagtg tcactaaggc gatagcatat tttcaggtcc attgtaatct   6420
aatgggacca ccatcatata tgcagtccac cattgactga aatgttacat ggtacgtaac   6480
tgtatttgca agaatgattt gttttacatt aatatcacat aggatgtacc tttttagagt   6540
gatatgttta tgtggattaa gatgtacaag tggagcaagg ggacaagagc ccttggttct   6600
gtcttggatg tgagctttta tgctcttctc atcatgtctg ttttcttatt aaattcaaag   6660
gcttggacag gccctattta gcccttgttt tctatgtgtt ctaaataact aaagctttta   6720
aattctagcc atttagtgga gaactctctt tgcaatggta aaatgctgta ttggtttctt   6780
gactagcata ttaaatatat ttatctttgt cttgatattt caatgtcatt ttaaacatca   6840
ggattgggct ttagtattct catacccaga gagttcactg aggatacagg actgtttgcc   6900
catttttgt tatggctcca gacttgtggt atttcgatgt cttttttttt tttttttttt   6960
tttaaccttt tagcagcttt aaagtatttc tgttgttagg tgttgtatta cttttctaag   7020
attactgtaa caaagcacca caaactgagt ggctttaaac aacagcaatt tattctctca   7080
caattctaga agctagaagt ccgaaatgga agtgttgatg gggcatgatc ctcaaaagag   7140
agaagactct ttccttgcct cttcctggct tctggtggtt accagcaatc ctgagcgttc   7200
ctttcttgct tcgtagtttc agcagtccag tatctgcctt ttgtcttcac atggatgtct   7260
accccttgtc tctgtgtctc cagatctctc tccttataaa cacagaagtt actggattag   7320
gccccactct aatccagtat gaccccattt taacacgatt acacctattt ctaaataagg   7380
tcacattcac atataccaag ggttaggaat tgagcatatc ttttgcaggg acacaattca   7440
acccacaagt gtcagtctct agctgagcct ttcccttcct ggttttctcc tttttagttg   7500
ctgtgggtta ggggccaaat ctccagtcat actagacttg cacatggact ggagatttgg   7560
gaatactgcg ggtctattct atgagcttta gtatgtaaca tttaatatca gtgtaaagaa   7620
gccatttttt cagttcacta tttctttgaa tttcttaatg tatgccctga atataagtaa   7680
caagttacta tgtctcataa aatgatcata tcaacaaaca tttaatgtgc acctactgtg   7740
ctagttgaat gtctttatcc tgataggaga taacaggctt ccgcatcttt gacttaagag   7800
gacaaaccaa gtatgtctga atcatttggg gttttgatgg atatctttaa attgctgaac   7860
ctaatcattg gttttatatg tcattgttta gatatctcag gagcatttgg ataatgtgac   7920
agttggaatg cagtgatgtc gactctttgc ccaccgccat ctccagctgt tgccaagaca   7980
```

gagattgctt taagtggtga atcaccttta ttagcagcta cttttgctta ctgggacaat 8040
attcttggtc ctagagtaag gcacatttgg gctccaaaga cagaacaggt acttctcagt 8100
gatggagaaa taacttttct tgccaaccac actctaaatg gagaaatcct tcgaaatgca 8160
gagagtggtg ctatagatgt aaagtttttt gtcttgtctg aaaagggagt gattattgtt 8220
tcattaatct ttgatggaaa ctggaatggg gatcgcagca catacggact atcaattata 8280
cttccacaga cagaacttag tttctacctc ccacttcata gagtgtgtgt tgatagatta 8340
acacatataa tccggaaagg aagaatatgg atgcataagg taagtgattt ttcagcttat 8400
taatcatgtt aacctatctt ttgaaagctt attttctgat acatataaat cttattttta 8460
aattatatgc agtgaacatc aaacaataga tattatttat tttgcattta tcctgttaga 8520
tacaaataca tctggtctga tgcctgtcat cttcatatta actgtggaag gtaggaaatg 8580
gtagctccac attacagatg aaaagctaaa gcttaaacaa atgcagaaac ttttagatcc 8640
tggattcttc ttgggagcct ttgactctaa taccttttgt ttccctttca ttgcacaatc 8700
ctgtctttcg cttactacta tgtgtaagta taacagttca aaaaaatagt ttcataagct 8760
gttggttatg tagcctttgg tctctttaac ctctttgcca agttcccagg ttcataaaat 8820
gaggaggttg aaccgcatgg ttcccaagag aattcctttt aattttacag aaattattgt 8880
tttccccgaa gtcctatagt tcaatatata atgatattta catttcagta tagttttggc 8940
atatctaaag aacacattaa gttctccttc ctgtgttcca gtttgatact aacctggaag 9000
tccattaagc attaccaatt ttaaaaggct tttgcccaat agtaaggaaa aataatatct 9060
tttaaaagaa taatttttta ctatgtttgc aggcttactt cctttttttct cacattatga 9120
aactcttaaa atcaggagaa tcttttaaac atcataatgt ttaatttgaa aagtgcaagt 9180
cattcttttc ctttttgaaa ctatgcagat gttacattga ctattttctg tgaagttatc 9240
tttttttttcc ctgcagaata aagggtgttt tgattttatt ttgtgttgtt tataagaaca 9300
tacattcgtt gggttaattt cctgcccctg cccccgtttt ttccctaaag tagaaagtat 9360
ttttcttgtg aactaaatta ctacacaaga acatgtctat tgaaaaataa gtatcaaaat 9420
gttgtgggtt gtttttttaa ataaattctt tcttgctcag gaaagacaag aaaatgtcca 9480
gaagattatc ttagaaggca cagagagaat ggaagatcag gtatatgcag attgcatact 9540
gtcaaatatt attctcatgg catgtatctg tgtaaagttg atggctacat ttgtgaaggc 9600
cttggggaca tacagagtaa gccttaatgg agcttttatg gaggtgtaca gaataaacta 9660
gaggaagatt tccatatctt agacctgaag agttaaatca gtaaacaaag gaaaatagta 9720
attgcatcta caaattaata tttgctccct ttttttttct gtttgaacag aataaatttt 9780
ggataacttg ttactagtaa aaaatttaaa aattgtctgt gatatgttct ttaaggtact 9840
acttctcgaa ctttttccta gaagtagctg taacaggagg agagcatatg taccccctaag 9900
gtatctgggg tataggccca tgtccaaaca atatttcttt taagtcttgt gttgtatctt 9960
taagactcat gcaatttaca ttttattcca tgatataact attttaatat taaaatttgt 10020
cagtgatatt tcttaccctc tcctctagga aaatgtgcca tgtttatact ttggctttga 10080
gtgcccctga ggaacagaca ctagagtttg agaagcatgg ttacacaggc gtggcttccc 10140
ctgcagaaat taagtacaga ctatttcagt gtaaagcaga gaagttcttt tgaaggggaa 10200
tctccagtga agaaagggtt cttcactttt acttccattt cctcttgagg gtgaccctca 10260
ttgctccttg taaaactccg atattttaaa catggctgtt ttgctttcct ctggttcttt 10320

-continued

```
ttaacatgag tgagacagat gatactttaa aaagtaattt taaaaaaaag tgttaaaata  10380
tatggccata atgcagaacc ctatgctgtg atctccttta ccaaattgtt gtgtttgtac  10440
ttttgtagat agctttccag tccagagaca gttattctgt gtaaaggtct gactcaacaa  10500
gaaaagattt ccctttaccc aaagaatgcc agtctttatt tgctggtcaa taagcagggt  10560
ccccaggaaa ggggtaactt tcaccaccct ctaacccact ggttattagt aaactaatta  10620
agtagactta tctcaagatg aggaaactta aaaccaagta aaattctgct tttactggga  10680
ttttattttt tgaaaccaga aacgtttact taagttgact actattaatg aattttggtc  10740
tctcttttaa gtactcttct taaaaatgtt atcctactgc tgagaagttc aagtttgaga  10800
agtacaagga ggaatagaaa cttgagagat tttctttttc ttttagagcc tcttctgtat  10860
ttagccctgt aggaattttt tttttccccc aagattcttc ttcgtgaaaa ggaggagttg  10920
ccttttgatt gagttcttgc aaatctcaca acgactttat tttgaacaat actgtttggg  10980
gatgatgcat gagtctgaaa caacttcagt tgtagctgtc atctgataaa attgcttcac  11040
agggaaggaa atttagcacg gatctagtca ttattcttgt tagattgaat gtgttaatca  11100
taattgtaaa caggcatgat aattattact ttaaaaactg aaaacagtga atagttagtt  11160
gtggaggtta ctaaagcatg attttttaa aataaaactt tcagcatttt gcaaatatgc  11220
atatggttta ggatagaact tccagaggta gcatcacatt taaattctca agcaacttag  11280
taatacgagg ctctgaaaaa ctggttaaag ttactccaga aatggccctg ggtctgacag  11340
acattctaac ttaaagatgc atatgaagac tttgaataaa atcatttcat atgaagacat  11400
tgaataaaat catttcataa aataagtgag gaaaaacaac tactattgaa ttcatcttaa  11460
tgtatgattt taaaaatatg tttagctaaa aattcataga catttgacaa tttcgtttat  11520
atctcaaaaa gttgacttac ccaagttgat cacaaaactg atgagactgg tggtggtagt  11580
gaataaatga gggaccaccc atatttgaga cactttacat ttgtgatgtg ttatactgaa  11640
ttttcagttt gattctataa actaccaatt tcaaaattac aatttcaagg tgtaataagt  11700
agtggtatta tcttgaaata ggtctaaagg gaacttttct gttttaaaat attcttaaac  11760
tatatgtgct gattttgatt tgcatttggg tagattatac tcttatgaat cggggggctg  11820
ggtattgatt caggttttcc ttacctattt ggtaaggatt tcaaagtctt tttgtgcttg  11880
atttcctcg tttttaaata tgaaacatat tgatgacttt taattaacaa atgtttttat  11940
ctcgaataaa ttttaaagga gatcttttct aaaagaggta tgatgactta attattgcat  12000
ataacaataa atgagaaacc agtgattcca tactctctaa agaataaaag tgagctttag  12060
gcccaggcat ggtggctcat gcctgtaatc ccagcacttt ggaaggccga ggcaggcgga  12120
tcacctgagg tcaggaattc gacaccagcc tggccaaatg gcaaaaccct gtctctacta  12180
caaatacaaa aattagctgg gcatggtggc agcccctata gtcccagcta cttggaagac  12240
tgagacagga gagtcactcg aacccgagag gcagaggttg cagtaagctg aaatcacacc  12300
attgcactcc agcctgggca acaagagcaa aactccgtct caaaaaaaaa aaaaaaaaaa  12360
aaaaagaata aaagtgagct ttggattgcg tataaatcct ttagacaagt agtagacttg  12420
tttgatactg tgtttgaaca aattacaaag tattttcatc aaagaatgtt attgtttgct  12480
gttattttta ttttttattg cccagcttct ctcatattca ttatgtgatt ttcttcactt  12540
catgttactt tattgtgcag ggtcagagta ttattccaat gcttactgga gaagtgattc  12600
ctgtaatgga actgctttca tctatgaaat cacacagtgt tcctgaagaa atagatgtaa  12660
gtttttatat ttttaaatga gagcaattat accctttatc agtttttttgg ggttatatta  12720
```

-continued ttattatgta tattattaat attctaattt taatactaag cacttcgtcg tacgtactat 12780
ccacatgcag tattagccac ttgaacagat aagcacacac aaaatcctgg attttatggc 12840
ataacagagg catttttgat cagtgatgac aaaactaaat ttatttttgtt tatttcacta 12900
cttttataat tcctaaaagt gggaggatcc cagctcttat aggagcaatt aatatttaat 12960
gcagtacctt ttgaaacaaa actgtgtgcc aaagcagtaa ccattaatgg aagttgactt 13020
atagtcacaa atttagtttc cttaatcatt tgttgaggat gttttgaatc acacactatg 13080
agtgttaaga gatatcttta ggacactatt cttgttgttt tattgtcatt taggttagtc 13140
tcctgtctga cagctcagaa gaggaagttg ttcttgtaaa aattgtttac acaacctgat 13200
tgaccagctt tcacatttgt tcttctgaaa gctgatggta gtgcacagat tgttttatgg 13260
ggagtcttga ttctcagaaa tgaaggcagt gtgttatatt gaatccagac ttcagaaaac 13320
ttgtatatta aaagtgtttt ttcaacacta tgttatagcc agactaattt ttttattttt 13380
ttgatgcatt ttagatagct gatacagtac tcaatgatga tgatattggt gacagttgtc 13440
atgaaggctt tcttctcaag taagaatttt tcttttcata aaacctggat gaagcatatg 13500
ttcacctatg acaagatttg gaaggaagaa aataacagac tgtctactta gattgttcta 13560
gggacaacat tgcatatttg aattgttgct taaatttgtg ttatttttca ttcgttatat 13620
ttctataata tatttgatgt tattccattt gctatttaaa gaaactgagt ttccatattt 13680
cccagacaag aaatcatggc cccttgcttg attctggttt cttgttttac ttctcattaa 13740
agctaaaaga accctttcaa attaagttgt actgtagatg aacttaagtt atttaggcct 13800
agaaaaaaaa aattcatatt tatactgatc tttttccatc cagcagtgga gtttagtact 13860
taagagtttg tgcccttaaa ccagactccc tgggttaatg ctgtgtacct gtgggcaagg 13920
tccctgaatt ctctatacac ctatttcctc atctgtaaaa tggcaataat aataatagta 13980
cctaatgtat agagttgtta taagcattga gtaagataaa taatataaag cacttagaac 14040
agtgcctgga acataagaac acttaataat agctaacatt ttctatttac atttcttcta 14100
aggaaaaggt taacagaaat agccaatatt tgttcagtgc ctacatgtta gttcctatac 14160
taagtgcttt acatgtatta tcttatattc tattttaatg tttcttcaca gttgcagatt 14220
atcatgaaat tttatttttt aaaaaagaga agtaaaagga taaagtattc acttttatgt 14280
ccacagtctt ttcctttagg ctcatgatgg agtatcagag gcatgaatgt gtttaaccta 14340
agagccttaa tggcttgaat cagaagcact ttagtcctgt atctgttcag tgtcagcctt 14400
tcaaacatca ttttaaatcc catttgactt taagtaaatc acttaatctc tctacatgtc 14460
aatttcttca gctataaaat gatggtattt caataaataa atacattaat taaatgatat 14520
tttacaaact aattgggctg ttttaaggct caataagaaa atttctgtga aaggtctcta 14580
gcaaatgtag ggttctatac aaataaaaga taacattatg cttatatctt cggtgtttat 14640
catgcaaagc tcttctgagt tttttgaaga gctcacctac tattttttgt ttttagtttg 14700
ttaaattgtt ttataggcaa tgtttttaat ctgttttctt taacttacag tgccatcagc 14760
tcacacttgc aaacctgtgg ctgttccgtt gtagtaggta gcagtgcaga gaaagtaaat 14820
aaggtagttt attttataat ctagcaaatg atttgactct ttaagactga tgatatatca 14880
tggattgtca tttaaatggt aggttgcaat taaaatgatc taatagtata aggaggcaat 14940
gtaatctcat cgaattgctg agacaacttg tggcaacagt gagtttgaaa taaagtgaat 15000
aggagtcatt tatcagttta ttttgataac ttgtaaatac cagtgtcaga tgtgtataaa 15060

-continued

```
tggttttgag aatatattaa aatcaggtat ttaaaaaaac actattcttc tatttcccaa  15120
tgtaatcttt aacaaatctg aaggtagtca tgtactttcg gtactagttc tgaagaaatg  15180
ttatttgttt attcatcttg atttcattgt cttggctttc cttctaaatc tatcccttct  15240
tgggagctat tgggattaag tggtcattga tgattatact ttattcagta atgtttctga  15300
ccctttcctt cagtgctact tgagttaata aaggattaat gaacagttac atttccaagc  15360
attagctaat aaactaaagg attttgcact tttcttcact gaccattagt taaaaacagt  15420
tcagagataa gtacatgtat ctttcaattc tagcaaacct aattttttaa aagaagtttt  15480
acataggaaa tatgttggaa atgattattt actttacaaa gatattcata atttattttt  15540
tctgtaacta gctactttgt atatttacat gagccttaat ttatcaaaat tatatttctc  15600
atataaccat ttatgagagc ttagtattcc tctgtcatta tattgcgtct acggactagt  15660
gatcttacta cttctgttac ctcgaacaag tggcttcccg tctgtgacct ccaaagccgt  15720
aggttccaca gagtgactgc tgagctgctt tatgaaggga gaaaggctcc atagttgggt  15780
ttttggtttt gcttttgttt ttgtttttaa catttttcct atcctccatc ctcttgaggc  15840
agagtagctt accttttatc ttgttttaat ttgagaaaga agttgccact gctctagatt  15900
gaaaaccact gctttaacat aataactctg aatatggttt gaatttcaag atagtgacat  15960
gccttttat ttttactaat agagctgtag gtcgaatatt attagatttc taaaccccac  16020
ccaatgacct ccttatttta aatcaaattt aataattaat tatcttctta ttggaggatc  16080
tggacattct ttgatgtttc ttacaatgaa tttcacatgt agacccacta aacagaagtt  16140
ataaaggttc catggtcaaa taagtctgag aaagtctgca tattatataa ttcacctaaa  16200
gagtcacagt atgtacccaa atgttaaagg ttttgagatg ccatacagta aatttaccaa  16260
gcattttcta aatttatttg accacagaat ccctatttta agcaacaact gttatatccc  16320
ataggttcca ggtgactaaa gaatacttat tgcttaggat atgttttatt gataataaca  16380
attaaaatgt cagatatctt tcataagcag atcagtggtc tttttaaaac tttgtatttt  16440
aatgctaaaa tcttttcttt tgtagatagt cagaacatta tgccttttc tgactgcagc  16500
agagagaaaa tgctccaggt tatgtgaagc agaatcatca tttaaatatg agtcagggct  16560
ctttgtacag ggcctgctaa aggtatagtt tctacttatc acaagggaaa ccaattttct  16620
aaaatcattt ttgagactct ttgtagacaa atattaaata ttagcattta atgtatctca  16680
tattgacatg cccagtgact gacttccttt gcacagttct gcgcatagac tatatgtctt  16740
atggatttat agttagtatc atcagtgtaa caccatagaa taccctttgt tttccaggtg  16800
ggtccctgta cctacatgtc tagcatcagg tgttgttttt tttttttttt tttaaaacat  16860
atgcttaaat caggttgcac atctaaaata agatcatttc tttttaacta aatagatttg  16920
aattttattg aaaaaaattt taaaacatct ttaagaagca tataggattt aagcagttac  16980
tatgtatgtg tactaaaata tatatatatt cctaaatata tattcctata tataatatat  17040
gtatttctat atataatata tattagaaaa aacttagagt tttctttcat ttgagtctac  17100
tgttcaagga gcaaaacaga gaaatgtaaa ttagcaatta tttacaataa ttaaagggaa  17160
gaaagttgtt caccttgttg gatctattat tgttgtttta attatagtcc caagacgtga  17220
agaaatagct ttcctaatgg ttatgtgatt gtctcatagt gactactttc ttgaggatgt  17280
agccacagca aaatgaaatt taaaaaattt aaaaattgtt gcaaataaaa gttatattag  17340
gcttttgtgc aatttcaata atgtgctgct atgaactcag aatgatagta tttaaatata  17400
gaaactagtt aaaggaaaca cagtttctat ttgagttata caaatctgta aattagaact  17460
```

-continued

```
tctcctgtta aggcattata aagtgcttaa tacttttgtt tcctcagcac cctctcattt  17520
aattatataa ttttagctct gaaagggacc tataccagat gtgtagagga aatttcaaaa  17580
ctatgatcta atgaaaaaat atttaatagt tctccatgca aatacaaatt atatagtttt  17640
ctggaaaata cctttgacat tatacaaaga tgattatcac agcattataa tagtgaaaaa  17700
atggaaatag cctctttctt ctgttctgtt cacagcatat ggcacagtac ctcatatgca  17760
gtaggttatt atgacctggt aactggctcc cccaactgat taggaaagaa gtaaatttgt  17820
tatttataaa aatacgtgtt cattgagatg catagaataa ttaagaaatt aaaagacact  17880
tgtaatttca aatccagtga atacccactg ttaatatttg gcatatctct ttctagtctt  17940
tttttccctt ttgcatgtat tttctttaag actcccaccc ccactggatc atctctgcat  18000
attctaatct gctttttca cagcagattc taagcctttt tgcatatcaa cacaaacttc  18060
aacaacttca tctttagatg ctaaataatg aattcatttt tatttactta accactttct  18120
ttggatgctc aggttattct gatgttttgc cattaaaacc aatgctatac tgaacacttc  18180
tgtcactaaa acttgaacac actcatgaat aatttcttag gataaatttt tagagatgga  18240
tttgctaaat caaagaccat tttttaaaaa ttgaaaaaca attatatcgt ttggcatgta  18300
agacagtaca ttttcctttt attttgacag gattcaactg gaagctttgt gctgcctttc  18360
cggcaagtca tgtatgctcc atatcccacc acacacatag atgtggatgt caatactgtg  18420
aagcagatgc caccctgtca tgaacatatt tataatcagc gtagatacat gagatccgag  18480
ctgacagcct tctggagagc cacttcagaa gaagacatgg ctcaggatac gatcatctac  18540
actgacgaaa gctttactcc tgatttgtac gtaatgctct gcgtgctggt actgtagtca  18600
agcaatatga aactgtgtct tttatgaata aaaacaaaac agaagttgca ttcaaaaaga  18660
aagaaatatt actagcagaa ttatgcttga agaaacattt aatcaagcat tttttcttta  18720
aatgttcttc tttttccata cgattgtgtt taccctaaaa taagtaagat taacccttaa  18780
agtgaatatt taactatttg tttaataaat atatattgag ctcctaagca ctgttctagg  18840
tactgggctt aatagtggct aaccacacag ctccagcccc tacattgcat atagtctatt  18900
gtataagtta ctgaatggac ttactaacaa aaccagagaa gtaattctaa gtcttttttt  18960
tcttgacata tgaatataaa atacaacaaa actggtaaaa tatattaata gagcattctt  19020
ttactttgca ttttatattg ttactcactt cgtatttaag aaaaacagtc tgatcaggaa  19080
attcaaaagg aaaagtaatg ataattaatt gagcatagac ccaacttgaa aagaaaaaaa  19140
aggatgatga taaatctata atcctaaaac cctaagtaaa cacttaaatg atgttctgaa  19200
atcaggaaaa gaattatagt atatttttgt ggttctcttt tattagttga aaaaaggcac  19260
agtagctcat gcctataaga acagagcttt gggattccaa ggcaggcaga tcacttgagg  19320
ccaggagttc cagaccagcc tgggcaacat agtgaaaccc catctctaca aaaataaaaa  19380
agaattagtt gaatgtgttt ctgtgtgcct ataatcctag ctattcagaa agctgaggca  19440
ggaggatctc ttgagcccag gagtttgagg ttacatggag ttatgatgtg ccagtgtact  19500
ccagcctgcg ggacaatgag actctgtctt gttaaaaaaa aaagtgcttg gaataatgtt  19560
tggcatatag aaggtaacaa cagtaaatgt taactgtaat aacccaggta taagtgtgta  19620
aggtgataga aaaattgggg caaacaaccc tgacctgtgt ctctacagaa taagtttgag  19680
ttgaggcaac agacatgtgg agcaccagta attacacact aaatgttaac caaaagcgtt  19740
gaatagtaac atcttattca agggaccccc agccttatat atctcaaggt gcagaaagat  19800
```

-continued gacttaatat aggacccatt ttttccgagt tctccagagt ttttattggt tcttgagaaa 19860
gtagtggggg aattgtttta gaaaatgaat tggtcaaact gaaattccat gtcagtaagt 19920
ttttacatat tggtaaattt tgatagacat gtagaagttt tctaattaat ctgcgccttg 19980
aaacattttc ctttttccta aagtgcttag tattttttcc ctttttgat tggttgcttg 20040
ggagcttttt tgaggaaatt tagtgaactg cagaatgagt ttgcaaccat ttagtatttt 20100
tgttttgtgt tttagaggag gtatgtgtat tttaacattt cttaatcatt tttagccagc 20160
tatgtttgtt ttgctgattg acaaactata attaaacagc tattctcatt ttgctgatca 20220
tgacaaagta atatcctgaa tttttaaatt ttgcatccag ctctaaattt tctaaatttt 20280
ctaaacataa aattgttcaa aaaatagtat ttttagccac tagattgtgt gttgttaagt 20340
ctgttgtcac agactcattt tacttttcag tgtgtgtttt tacatgttaa ttatgtttgt 20400
catttttaat tttaactttt taaaataatt ccagtcactg ccaaaacatg aaaaattggt 20460
cactggaaat ttttttttta acttttattt taggttcatg tgtacatgtg caggtttgtt 20520
atacaggtaa attgcgtgtc gtgagggttt ggtgtaccca ggtaataagg gtagtaccca 20580
ataggtagtt ttttgatcct tacccttctc ccacccttct ttcaccctcg agtaggcctt 20640
ggtgttgctg tttccttctt tgtgtccatg tgtactcaat ggttagctcc tacttagaag 20700
tgagaacatg cggtatttgg ttttctgttc ctggattagt tcactcagga taatggcctc 20760
tagctccatc tgttttttat ggctgcatag tattccatgg tgtatatgta tcatgttttc 20820
tttatccagt ctaccattga tagacattta ggttgattct ctgtctttac tatcatgaat 20880
agcgctgtga tgaacatata cacatgcatg tgtccttatg gtggaacaat ttgtattcct 20940
ttaagtatat acagaataat ggggttgcta gggtgaatgg tagttctatt gtaagttatt 21000
tgtgaaatct tcaaactgct tttcacaata gctaaactaa tttacagtcc caccagcagt 21060
gtataagtgt tccctttttct ccacaacctt gccaacatgt tattttttta cttttcaata 21120
ataggcattc ctagagaatt gatttgcaat tctctaatga ttagtgatat tgagcatttt 21180
ttcgtatgct ttttagctgt gtgtatatat tcttttgaaa aatgttaatg tcctttgccc 21240
agtttgtaat ggggttgttt gtttttgctt gttaattaaa gttccttcca gattctggat 21300
atccctttgt cagatgcgtg gtttgcagat atttttctcc ccttgtgtag gttgtctttt 21360
tactctgttg atagtttctt ttgccgggca ggagctcatt aggtctcatt tgtgtttgtt 21420
tttgttgcag ttgcttttgg cgtcttcatc ataaaatctg tgccagggcc tatgtccaga 21480
atggtatttc ctagtttgtc ttccagggtt tttacaattt tagattttac gtttatgtct 21540
ttaatccgtc ttgagttgat taaggaaggg gtccagtttc actctaattc ctatggctaa 21600
caattatccc agcaccattt attgaatacg gagtcctttc cccattgctt gtttttgtca 21660
attttgttga agatctgatg gttgtaggtg ctatgtggct ttatttcttg gctctctatt 21720
ctccactggt ctgtctgttt ttataccagt accctgctgt taaggttcct atagcctttt 21780
agtataaggt cggctaatgt gatgcctcca gctttgttct ttttgcttag gattgctttg 21840
gctatttggg ctcctttttg gttccatatt aattttaaaa tagtttttttc tagttttgtg 21900
aagaatgtca ttgatagttt agaggaatag cgttgaatct gtagattgct ttgggcaaat 21960
ggccatttta acaatattga ttcttcctat ctatgaacat ggaatgtttt tccatgtgtt 22020
tgtgtcatct ctttatacct gatgtataaa gaaaaaccag tattattgct actcaatctg 22080
ttccaaaaaa ttgaggagga ggaactcttc cctaatgaga ccggcttcct tctgatacca 22140
aaacctggca gagatacaac agaaaaaaga aaacttcagg ccaatatcct tgatgaatat 22200
agatgcaaaa atcctcaaca aaatactagc aaccaaatcc agcagtacgt caaaaagcta 22260
atctacttta agtaggcttt atccctggga tgcaaggttg gttcaacata cacaaatcaa 22320
taagtgtgat tcatcacata aacagagcta aaaacaaaaa ccacaagatt atctcaatag 22380
gtgcagaaaa ggctttcaat acaatttaac atccttcatg ttaaaaacct tcagtaggtc 22440
aggtgcagtg actcacacct gtaatcccag cactttggga ggccaaggcg gacgtatatc 22500
ttaagcccag gagttcaaga ccagcctagg cagcatggtg aaaccccatc tctacaggaa 22560
aaaaaaaaaa aaaaaaaaaa aaaaaaaaaa agcttaatat ggcggcatgc acctatagtc 22620
ccagctactc aggaggttga ggtgggagga ttgcttgagc ccaggaggca gaggttgcag 22680
cgagctgaga tcgtgccact gcactccaac ctgggcaata aagtgagacc ctgtctcaaa 22740
aagaaaaaca aaaataatcc taaaccaact aggcattgaa ggaatatgcc tcaaaaaaat 22800
aagaaccatc tatgacagac ccacagccaa tatcttacca aatgggcaaa agctggaagt 22860
attctccttg agaaccgtaa caagacaagg atacacactc tcatccctcc ttttcagcat 22920
agttctggaa gtcctcgcca gagcagtcag gaaagagaaa gaaagaaaag gcattcagat 22980
aggaagagaa gaagtcaaac tatttctgtt tgcaggcagt ataattctat acctagaaaa 23040
tgccatagtt tctgcccaga agctcctaca tctgttaaaa atttcagcaa agttttagca 23100
ttgtctgtat tccaacagct tccagggtga gagtgaaatc aggaacacag tcccgttcac 23160
aatagccgca aaaagaataa aataccttgg aatccagcta accagggagg tgaaacatct 23220
ctacgagaat tacaaaacgc tgctgaaaga aatcagagat gacacaaaca aatggaaatg 23280
ttgtttttaa caccttgctt tatctaattc acttataact aagatattca ttcagtggaa 23340
caggtataat aagaccactc gacttaaata taagccttat tctctttcca gagcccaaga 23400
aggggcacta tcagtgccca gtcaataatg ataaaatgct gatatttttc ccctttactg 23460
tttctttctt ctgtagtgtg gtacactcat ttcttaagat tagaaaactt gacctacctt 23520
cctgtttgct tctacacacc cccattctct ttttttgcca ctccggtcag gtataggatg 23580
atccctacca cttttagtta aaacctcctt cccttattaa atgttctctt accactctgg 23640
cctgagtaga acctagggaa aatggaagag aaaagatgaa agggaggtgg gggctgggaa 23700
gggaatagtc ttgtttgtgt gtttgcttta gcacctacta tatcctaggt gctgtgttag 23760
gcacacatta ttttaagtgg ccattatatt gctacatctc actctggtca ttgccaaggt 23820
aggtagtact ttcttggata gttggttcat gttacttata ggtggtggac ttgttgaggc 23880
aaccccaatg gataatcatc tgagtgtgtt ctctaatctc agatttttct tcatattttt 23940
tggtttgttt tggtttttga tggtggtggt tgtgtgctta tttttgttgc tggcttgttt 24000
ttttgttttg tttttgatat ggcaagaatt ggtagtttta tttattaatt gcctaagggt 24060
ctctactttt tttaaaagat gagagtacta aaatagattg ataggtacat acataccttt 24120
atgggggact gcttatattc cttagagaaa aaaattactt attagcctga caaacaccag 24180
taaaatgtaa atatatccgt gagtaaataa atgaatgtat gctttgtatc tccaaatata 24240
tacatctata ttcttacaaa tatgttttta tgtaatacca atttataaga acttaaaatg 24300
ttggctcaag tgagggatgg tggaaagtag cattatatag ccatttcaac atttgaactt 24360
ttttcttcat tttcttcttt tcttcaggaa tatttttcaa gatgtcttac acagagacac 24420
tctagtgaaa gccttcctgg atcaggtaaa tgttgaactt gagattgtca gagtgaatga 24480
tatgacatgt tttcttttt aatatatctt acaatgcctg ttctctctct ctatatatat 24540

-continued

```
atatttatat atttccctgg atcatgcccc agagttctgc tgagcaattg cagttaagtt  24600
agttacacta cagttctcac aagagtctgt gaggggatgt caggtgcatc attacattgg  24660
atgcctcttg tcctagattt atgtttcggg aattcagacc tatgtttaca atataataaa  24720
tattgttgct gccttttaca gataaaataa taagatataa acttgaccac aactactgtt  24780
ttttgaaaca tagagttcat ggtttacatg tatcaaagtg aaatctgagt tagcttttac  24840
agatataata tatacatata tatatcctac aatgcttgta ctatatatgt agtacaagta  24900
tatatatgtg tgtgtgtgtg tgtatatata ttatggcact gtagtatata tatgtttata  24960
tgttaaaaaa tatataaata tatgttacat atttaacata aacatatata catatatgtt  25020
aaatatataa catatactct atatatgaca aatagagtat aatatatatt tttatttttt  25080
atatatatat aaaacatgat agaattaaga attaagtcct aatctgtttt attaggtgct  25140
ttttgtagtg ttcagtcttt ctaaagtgtc taaatgattt ttccttttga cttattaatg  25200
gggaagagcc tctatattaa caattaaggc tgcagcattg attacttcaa acaacaaaca  25260
ttttaattca agcattaacc tataactcaa gtaagttttt tttttttttt ttttgagaaa  25320
gggaggttgt ttatttgcct gaattgagtc aaaaatattt ttgaaacatc atgtactcat  25380
ttaaatgata acatctttat tgtttcattc ttttaaaaaa tatctactta attacacagt  25440
tgaaggaaat tgtagattat atggaactta tttcttaata tattacagtt ttgttataat  25500
aacattctgg ggatcaggcc aggaaactgt gtcatagata aagctttgaa ataatgagat  25560
ccttatgttt actagaaatt ttggattgag atctatgtgg tctgtgacat attgcaaagt  25620
tcaaggaaaa ttcgtaggca tggaatttct caaactgaaa atccctccca ctgtccacct  25680
catcacatgc acacattcta ctcttaccca cccactccac cccttgcaaa agtacagata  25740
tatgaatgtc tcaaaaccat gggctcatct tctagaagct tcaatgttat ttgaagattt  25800
gggcagagga agttaagaaa tatgaaatag cttacatatg agttttaata gtgaaacaaa  25860
catggatgta ttctgaagta gaatgcaaaa tttgagtgca tttttttttt tttgagactg  25920
agtctggctc tgtcgcccag gctggagtgc agtggccgga tctcagctca ctgcaagctc  25980
cacctcccgg gtttacgcca ttctcctgcc tcagcctccc gagtagctgg gaccacaggc  26040
gcccgccact tcgcccggct agtttgtttg tattttttag tagagatggg gtttcaccgt  26100
gttagccagg gannnnnnnn nnnnnnnnnn nnnnnnnnnn nnnnnnnnnn nnnnnccatt  26160
gagtgcattt ttaaagataa atcagaaaac ttcgaaaaac tatcagattg gccggacatg  26220
gtggcttatg cctgtaatcc tagcactttg ggaggctgag gtgggtggat cacgaggtca  26280
ggagatcgag accatcctgc caacatggtg aaaccccatc tctactaagt atacaaaaat  26340
tagctgggcg tgacagcacg tgcctgtaat cccagctact tgggaggctg aggcaggaga  26400
atcgcttgaa cccgggaggt ggaggttgca gtgagtcaag atcacaccac tgcacttcag  26460
cttggtgaca gagctagact ccatatcaaa aaaaaaaaaa aaaaaaagaa gtcagattgt  26520
tcctacaccc agtgcttcta taccacactc ctactagggg gcatcagtgg aaatggttaa  26580
ggagatgttt agtgtgtatt gtctgccaag cactgttaac actgtcctag aaacattgct  26640
gtacaagtag aatgtgagca aattatgtat tgaaatggtt cctctccctg caggtctttc  26700
agctgaaacc tggcttatct ctcaggagta ctttccttgc acagttttta cttgtccttc  26760
acagaaaagc cttgacacta ataaaatata tagaagatga tacgtgagta caactcctac  26820
atggaggaaa aacctttgt acgttgtttt ttgttttatt tcctttgtac attttctgta  26880
tcataatttt tgcttttttt tttttttttt ttttctccat tactttcagg cagaagggaa  26940
```

aaaagccctt taaatctctt cggaacctga agatagacct tgatttaaca gcagagggcg 27000
atcttaacat aataatggct ctggctgaga aaattaaacc aggcctacac tcttttatct 27060
ttggaagacc tttctacact agtgtacaag aacgagatgt tctaatgact ttttaaatgt 27120
gtaacttaat aagcctattc catcacaatc gtgatcgctg ctaaagtagc tcggtggtgt 27180
ggggaaacat tcccctggat catactccag agctctgctc ggcagttgca gttaagttag 27240
ttacactaca gttctcacaa gagtctgtga ggggatgtca ggtgcatcat tacattggat 27300
gtctcttttc ctagatttat gcttttggga tacagaccta tgtttacaat ataataggta 27360
ttattgctgt cttttaaata tataataata ggatataaac ttgaccacaa ctgctgtttt 27420
tttgaaatat atgattcatg gtttacatgt attaaggtga aatccgagtt cgcttttaca 27480
gatattagtt gactttctat cttttggcat tctttggtgt gtggaattac tgtaatactt 27540
ctgcaatcaa ctgaaaatta gagcctttaa atgatttcag ttccacagaa agaaagtgag 27600
cttcaacata ggataagctt tagaaagaga attgatcaag cagatgttta attggaattg 27660
attattagat cctgctttgt ggatttagcc ctcgggattc agtctgtaga aatgtctgat 27720
agttctctat agtccctgct catggtgaac cacagttagg atgttttgtt tgttttattg 27780
ttgttgctat tgttgatgtt ctatatagtt gagctctata aaaggaaatt gtattttatg 27840
ttttagtagt tgttgccaac tttttaaatt aattttcatt atttttgagc caaattgaaa 27900
tgtgcacctc ctgtgccttt tttttccttg gaaaatcgaa ttacttggaa gaagttcaga 27960
tttcactggt cagtcgtttt catcttgttt tcttcttgca gagtcttacc atgtacctgc 28020
tttggcaatc attgtaactc tgagattata aaatgcatta gagaatatat taactaataa 28080
gatctttttt ttcaggaaca gaaaatagtt ccttgagtac ttccttctta catttctgcc 28140
catgtttttg aagttgttgc catttgcctg caataggcta taaggaatag caggagaaat 28200
tttactgaag tgctattttt ctaggtgcta ctttggcaga gctaagtggt ctgtttcttt 28260
tgtttcctta atgcgtttgg accattttgc tggctgtaaa ataactgatt aatataattc 28320
taacacaata ttgacattgt agtgtacaca aacacaaata ttttatttaa aactggaagt 28380
aacataaaag ggaaaatata tttataagaa aggaataaag gtaatagagc tcttctgtcc 28440
cccagccacc aaatttacac aacaaaatca tatgttctaa tgtgaaaggt cataatagct 28500
ttcccatcat taatcagaaa gatgtggcag cttgattttt tagacaaccc ctgaactaga 28560
tgactgttgt actgtagctc agtcatttaa aaaatatata aatactatct cgtagtgtcc 28620
catactatgt tttttacatg atagattctt atttaagtgc taactggtta ttttctttgg 28680
ctggtttatt gtactgttat atagaatgta agttgtacag tgaaataagt tattaaagca 28740
tgtgtaaaca ttgttatata tcttttctcc tagatggaga attttgaata aaatatnnnn 28800
nnnnnnnnnn nnnnnnnnnn nnnnnnnnnn nnnnnnnnnn nnnnnnnnnn nnnnnnnnnn 28860
nnnnnnnnnn nnnnnnnnnn nnnnnnnnnn nnnnnnnnnn nnnnnnnnnn nnnnnnnnnn 28920
nnnnnnnnnn nnnnnnnnnn nnnnnnnnnn nnnnnnnnnn nnnnnnnnnn nnnnnnnnnn 28980
nnnnnnnnnn nnnnnnnnnn nnnnnnnnnn nnnnnnnnnn nnnnnnnnnn nnnnnnnnnn 29040
nnnnnnnnnn nnnnnnnnnn nnnnnnnnnn nnnnnnnnnn nnnnnnnnnn nnnnnnnnnn 29100
nnnnnnnnnn nnnnnnnnnn nnnnnnnnnn nnnnnnnnnn nnnnnnnnnn nnnnnnnnnn 29160
nnnnnnnnnn nnnnnnnnnn nnnnnnagaa gactaattga tcatatcact atgattctca 29220
aagaagaacc aaaacttcat ataatactac aaatatgaga tagttacttc tgtagtatat 29280

```
ttctgtaatg ctacaggtta aacaggtcac tcttatataa cactattttg attttgatgt  29340

agaattgcac aaattgatat ttcttctatg atctgtaggg tatagcttaa agtagcaaaa  29400

acagtccacc acctccagtt aacacacagt aacactatgg gactagtatt attatttcca  29460

ttttacaaag gaggaaacta aagcttaaag atgtgtaata tacagcccaa ggtcacacag  29520

ctggtaaagg tagatttcat cccagacagt tacagtcatt gccgtgggca cagctcctaa  29580

cttattaact ccatgtaact ggtactcagt ttagttgaat tgaaaggaga gtagggaagc  29640

aggtctgttt gcactattca gagcccaagt gtgaatccct gctgtgctgc ttggagaagt  29700

tacttaacct atgcaaggtt catttttaa atatttgaaa cggaatgata atacatactt  29760

caccagtggg tttaatgaga ccttataaga tcgttagttc agtacctgac cagtgcttca  29820

taaatgcttt ttcatccaat ctgacaatct ctagcttgta attggggcat ttagaacatt  29880

taatatgatt attggcatgg taggttaaag ttgtcatctt gctgttttct ctttgttctt  29940

ttttctcctt tcttttggat tttttttaa ttttactgtg tcttctctgt tgtcttatta  30000

a                                                                  30001


<210> SEQ ID NO 12
<211> LENGTH: 20
<212> TYPE: DNA
<213> ORGANISM: Artificial sequence
<220> FEATURE:
<223> OTHER INFORMATION: Primer

<400> SEQUENCE: 12

gggtctagca agagcaggtg                                                20


<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13

gtcttggcaa cagctggaga t                                              21


<210> SEQ ID NO 14
<211> LENGTH: 24
<212> TYPE: DNA
<213> ORGANISM: Artificial sequence
<220> FEATURE:
<223> OTHER INFORMATION: Probe

<400> SEQUENCE: 14

tgatgtcgac tctttgccca ccgc                                           24


<210> SEQ ID NO 15
<211> LENGTH: 22
<212> TYPE: DNA
<213> ORGANISM: Artificial sequence
<220> FEATURE:
<223> OTHER INFORMATION: Primer

<400> SEQUENCE: 15

tgtgacagtt ggaatgcagt ga                                             22


<210> SEQ ID NO 16
<211> LENGTH: 25
<212> TYPE: DNA
<213> ORGANISM: Artificial sequence
```

<220> FEATURE:
<223> OTHER INFORMATION: Primer

<400> SEQUENCE: 16
gccacttaaa gcaatctctg tcttg 25

<210> SEQ ID NO 17
<211> LENGTH: 21
<212> TYPE: DNA
<213> ORGANISM: Artificial sequence
<220> FEATURE:
<223> OTHER INFORMATION: Probe

<400> SEQUENCE: 17
tcgactcttt gcccaccgcc a 21

<210> SEQ ID NO 18
<211> LENGTH: 783
<212> TYPE: DNA
<213> ORGANISM: Homo sapiens

<400> SEQUENCE: 18
gcctctcagt acccgaggct cccttttctc gagcccgcag cggcagcgct cccagcgggt 60
ccccgggaag gagacagctc gggtactgag ggcgggaaag caaggaagag gccagatccc 120
catcccttgt ccctgcgccg ccgccgccgc cgccgccgcc gggaagcccg gggcccggat 180
gcaggcaatt ccaccagtcg ctagaggcga aagcccgaca cccagcttcg gtcagagaaa 240
tgagagggaa agtaaaaatg cgtcgagctc tgaggagagc ccccgcttct acccgcgcct 300
cttcccggca gccgaacccc aaacagccac ccgccaggat gccgcctcct cactcaccca 360
ctcgccaccg cctgcgcctc cgccgccgcg ggcgcaggca ccgcaaccgc agccccgccc 420
cgggcccgcc cccgggcccg ccccgaccac gccccggccc cggccccggc cccggccccg 480
gcccctagcg cgcgactcct gagttccaga gcttgctaca ggctgcggtt gtttccctcc 540
ttgttttctt ctggttaatc tttatcaggt cttttcttgt tcaccctcag cgagtactgt 600
gagagcaagt agtggggaga gagggtggga aaaacaaaaa cacacacctc ctaaacccac 660
acctgctctt gctagacccc gcccccaaaa gagaagcaac cgggcagcag ggacggctga 720
cacaccaagc gtcatctttt acgtgggcgg aacttgtcgc tgtttgacgc acctctcttt 780
cct 783

<210> SEQ ID NO 19

<400> SEQUENCE: 19

000

<210> SEQ ID NO 20

<400> SEQUENCE: 20

000

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 21

-continued

```
gccttactct aggaccaaga                                                    20


<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22

ccggccccta gcgcgcgact                                                    20


<210> SEQ ID NO 23
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 23

cggcccctag cgcgcgact                                                     19


<210> SEQ ID NO 24
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 24

ccggccccta gcgcgcgac                                                     19


<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25

ccctagcgcg cgactcctga                                                    20


<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26

cccctagcgc gcgactcctg                                                    20


<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27

gcccctagcg cgcgactcct                                                    20


<210> SEQ ID NO 28
<211> LENGTH: 20
<212> TYPE: DNA
<213> ORGANISM: Artificial sequence
```

<220> FEATURE:
<223> OTHER INFORMATION: Synthetic oligonucleotide

<400> SEQUENCE: 28
ggcccctagc gcgcgactcc 20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
cggcccctag cgcgcgactc 20

<210> SEQ ID NO 30
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 30
cctagcgcgc gactcctg 18

<210> SEQ ID NO 31
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 31
ccctagcgcg cgactcct 18

<210> SEQ ID NO 32
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 32
cccctagcgc gcgactcc 18

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
gcccctagcg cgcgactc 18

<210> SEQ ID NO 34
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 34
ggcccctagc gcgcgact 18

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
cggcccctag cgcgcgac 18

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
aggctgcggt tgtttccctc 20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
caggctgcgg ttgtttccct 20

<210> SEQ ID NO 38
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 38
ggctgcggtt gtttccctc 19

<210> SEQ ID NO 39
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 39
aggctgcggt tgtttccct 19

<210> SEQ ID NO 40
<211> LENGTH: 19
<212> TYPE: DNA
<213> ORGANISM: Artificial sequence
<220> FEATURE:
<223> OTHER INFORMATION: Synthetic oligonucleotide

<400> SEQUENCE: 40
caggctgcgg ttgtttccc 19

<210> SEQ ID NO 41
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 41
gctgcggttg tttccctc 18

<210> SEQ ID NO 42
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 42
ggctgcggtt gtttccct 18

<210> SEQ ID NO 43
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 43
aggctgcggt tgtttccc 18

<210> SEQ ID NO 44
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 44
caggctgcgg ttgtttcc 18

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
tctgtctttg gagcccaaat 20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
ctgcgatccc cattccagtt 20

<210> SEQ ID NO 47
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 47
gccttactct aggaccaa 18

<210> SEQ ID NO 48

-continued

<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 48
tctgtctttg gagcccaa 18

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
ggttaatctt tatcaggtct 20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
tggttaatct ttatcaggtc 20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
ctggttaatc tttatcaggt 20

<210> SEQ ID NO 52
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 52
gttaatcttt atcaggtc 18

<210> SEQ ID NO 53
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 53
ggttaatctt tatcaggt 18

<210> SEQ ID NO 54
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 54

-continued tggttaatct ttatcagg 18

<210> SEQ ID NO 55
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 55
ctagcgcgcg actcctga 18

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
gggacactac aaggtagtat 20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
tacaggctgc ggttgtttcc 20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
cccggcccct agcgcgcgac 20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
ggtaacttca aactcttggg 20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
aatctttatc aggtcttttc 20